United States Patent
Bio et al.

(10) Patent No.: US 9,643,984 B2
(45) Date of Patent: May 9, 2017

(54) METHOD FOR THE PREPARATION OF [1,2,4]-TRIAZOLO[4,3-A]PYRIDINES

(71) Applicant: AMGEN, INC., Thousand Oaks, CA (US)

(72) Inventors: Matthew Bio, Santa Barbara, CA (US); Eric Fang, Somerville, MA (US); Jacqueline E. Milne, Simi Valley, CA (US); Sean Wiedemann, Cambridge, MA (US); Ash Wilsily, Somerville, MA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/900,976

(22) PCT Filed: Jun. 24, 2014

(86) PCT No.: PCT/US2014/043925
§ 371 (c)(1),
(2) Date: Dec. 22, 2015

(87) PCT Pub. No.: WO2014/210042
PCT Pub. Date: Dec. 31, 2014

(65) Prior Publication Data
US 2016/0347769 A1    Dec. 1, 2016

Related U.S. Application Data

(60) Provisional application No. 61/838,856, filed on Jun. 24, 2013.

(51) Int. Cl.
C07D 471/04    (2006.01)
C07D 519/00    (2006.01)

(52) U.S. Cl.
CPC .......... *C07D 519/00* (2013.01); *C07D 471/04* (2013.01)

(58) Field of Classification Search
CPC ................................................. C07D 471/04
USPC ........................................................ 546/122
See application file for complete search history.

(56) References Cited

U.S. PATENT DOCUMENTS 8,198,448 B2 *   6/2012   Albrecht ............. C07D 471/04
                                                               546/119
8,217,177 B2 *   7/2012   Albrecht ............. C07D 471/04
                                                               546/119

FOREIGN PATENT DOCUMENTS

WO    2008/008539 A2    1/2008
WO    2009/091374 A2    7/2009

OTHER PUBLICATIONS

Fang et al., "Magnesium coordination-directed N-selective stereospecific alkylation of 2-pyridones, carbamates, and amides using alpha-halocarboxylic acids," Journal of the American Chemical Society, vol. 132, No. 44, 2010, pp. 15525-15527, XP002729489.
PCT International Search Report and Written Opinion issued for a related PCT application No. PCT/US2014/043925 on Jan. 5, 2015 (16 pages).
Moulin et al., "Convenient two-step preparation of [1,2,4]triazolo[4,3-α]pyridines from 2-hydrazinopyridine and carboxylic acids," Tetrahedron Letters, vol. 47, 2006, pp. 7591-7594.

* cited by examiner

*Primary Examiner* — Niloofar Rahmani
(74) *Attorney, Agent, or Firm* — Lucas & Mercanti LLP

(57) ABSTRACT

Disclosed herein are methods for preparing [1,2,4]triazolo[4,3-a]pyridines, particularly (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one, and precursors thereof, such as a method comprising reacting (R)—N-(3-fluoro-5-(1methyl-1H-pyrazol-4-yl) pyridin-2-yl)-2-(3-(2-methoxyethoxy)-5-oxo-1,6-naphthyridin-6 (5H)yl) propanehydrazide ("HYDZ"): (HYDZ) under conditions sufficient to form (R)-6-(1-(8-fluoro-6-(1-methyl-IH-pyrazol-4-yl)-[1,2,4]triazolo[4,3-a]pyridin-3-yl)ethyl)-3-(2-methoxyethoxy)-1,6-naphthyridin-5(6H)-one ("A"): (A)

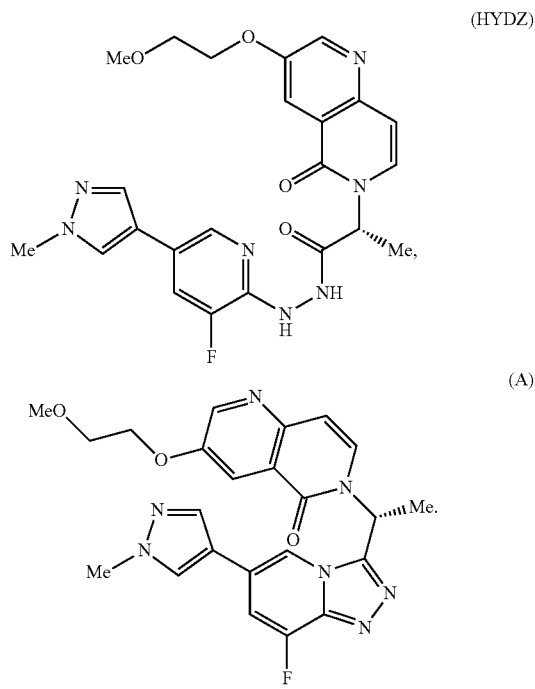

32 Claims, No Drawings

METHOD FOR THE PREPARATION OF [1,2,4]-TRIAZOLO[4,3-A]PYRIDINES

CROSS-REFERENCE TO RELATED APPLICATION

This application is a 371 of PCT/US2014/043925, filed Jun. 24, 2014, which claims the benefit under 35 U.S.C. §119(e) of U.S. Provisional Patent Application Ser. No. 61/838,856 filed Jun. 24, 2013, and the disclosure of each of which is incorporated herein by reference.

BACKGROUND OF THE INVENTION

Field of the Invention

The present disclosure relates to methods and processes for preparing [1,2,4]triazolo[4,3-a]pyridines, including those useful as cancer treatment agents and compositions, and for preparing precursors thereof. The disclosure includes stereospecific methods and processes.

Description of Related Technology

Some [1,2,4]triazolo[4,3-a]pyridines are useful in treatment of diseases such as cancer, in particular gastric, esophageal, NSCLC, melanoma and pancreatic cancer.

PCT publications WO08/008539 and WO09/091374, each of which is incorporated herein by reference, describe triazolopyridines and some processes of preparing them.

SUMMARY OF THE INVENTION

One aspect of the disclosure is a method of reacting (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ"):

(HYDZ)

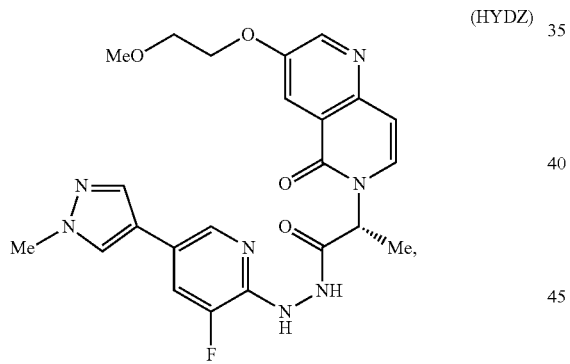

under conditions sufficient to form (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

(A)

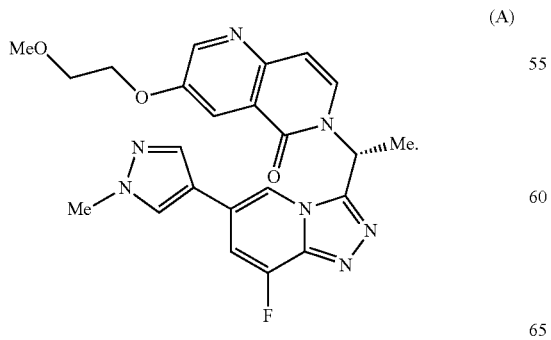

Optionally, the reacting comprises contacting the HYDZ with a thiophosphetane compound. Alternatively, the reacting optionally comprises contacting the HYDZ with a phosphorus (V) dehydrating agent. When the reacting comprises contacting the HYDZ with a dehydrating agent, the reacting can optionally be done in the presence of a base. Further, Compound A can optionally be contacted with an acid under conditions sufficient to form a salt of Compound A. Alternatively, Compound A can optionally be contacted with a water-rich solvent having a pH of at least 7 under conditions sufficient to form the monohydrate form of Compound A.

Another aspect of the disclosure is a method of forming HYDZ by reacting (R)-2-(3-(2-methoxyethoxy)-5-oxo-1,6-naphthyridin-6(5H)-yl)propanoic acid ("NAPA"):

(NAPA)

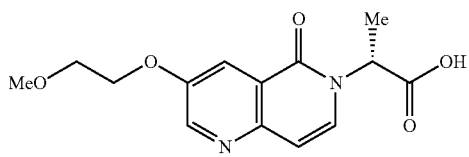

with 3-fluoro-2-hydrazinyl-5-(1-methyl-1H-pyrazl-4-yl)pyridine ("PYRH"):

(PYRH)

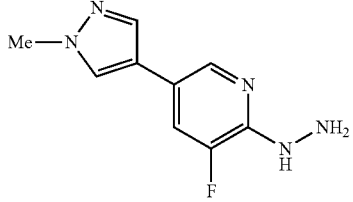

and a coupling reagent, and under conditions sufficient to form HYDZ:

(HYDZ)

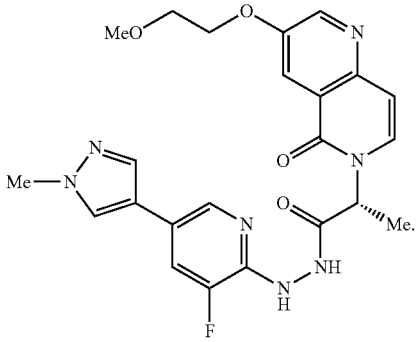

NAPA can be a salt, including, for example, HCl, HBr, sulfonic acid, diisopropylamine, or potassium.

Still another aspect of the disclosure is a method of forming NAPA by admixing 3-(2-methoxyethoxy)-1,6-naphthyridin-5(6H)-one ("NAPH"):

(NAPH)

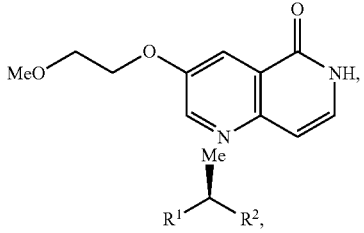

and a base, under conditions sufficient to form NAPA:

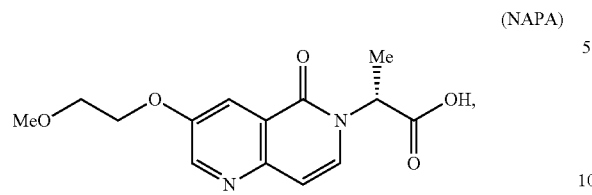
(NAPA)

wherein $R^1$ is Br, Cl, I, or OTf and $R^2$ is COOH or $C_{1-3}$alkyl ester, and when $R^2$ is $C_{1-3}$alkyl ester the method of forming the NAPA further comprises hydrolyzing the $C_{1-3}$alkyl ester to form an acid.

A related aspect of the disclosure is a method of forming NAPH by (i) admixing a methylnicotinate of Formula (I):

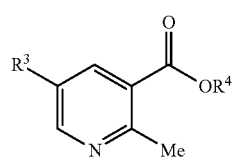
(I)

wherein $R^3$ is Cl, Br, or I, and $R^4$ is alkyl with 1,3,5-triazine, and a base, under conditions sufficient to form a naphthyridinone of Formula (II):

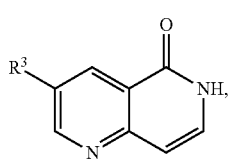
(II)

and
(ii) admixing the naphthyridinone of Formula (II) with methoxyethanol, a base, and a copper (I) catalyst, under conditions sufficient to form NAPH:

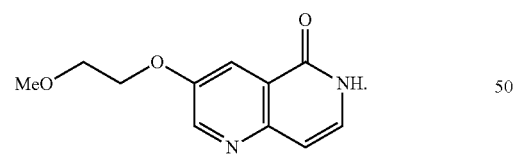

In still another related aspect, the disclosure is directed to a method of forming NAPH by (i) admixing protected N-(3-formyl-4-amino-2-alkoxy)pyridine:

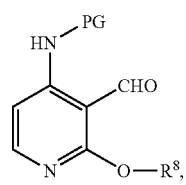

wherein PG is a protecting group and $R^8$ is alkyl, with 1-hydroxy-2-(2-methoxyethoxy)ethane-1-sulfonate:

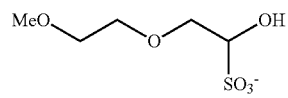

and base, under conditions sufficient to form a naphthyridine of Formula (III):

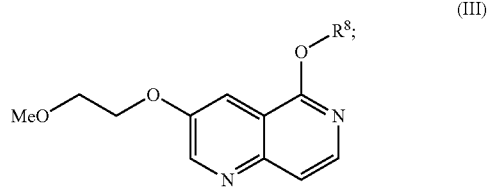
(III)

and
(ii) acidifying the naphthyridine of Formula (III), under conditions sufficient to form NAPH:

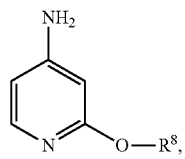

Still another aspect of the disclosure is a method including (i) admixing 4-amino-2-alkoxypyridine:

wherein $R^8$ is an alkyl group, with a pivaloyl compound of Formula (IV):

(IV)
$$R^5 \overset{O}{\underset{}{\cdot}} tBu,$$

wherein $R^5$ is Cl, Br, or OC(O)alkyl, and base, under conditions sufficient to form N-(2-alkoxypyridin-4-yl)pivalamide:

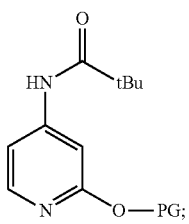

(ii) admixing N-(2-alkoxypyridin-4-yl)pivalamide with a lithium reagent, under conditions sufficient to form the protected N-(3-formyl-4-amino-2-alkoxy)pyridine:

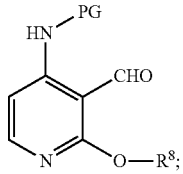

(iii) admixing the protected N-(3-formyl-4-amino-2-alkoxy)pyridine with 1-hydroxy-2-(2-methoxyethoxy)ethane-1-sulfonate:

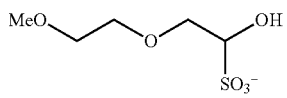

and base, under conditions sufficient to form a naphthyridine of Formula (III):

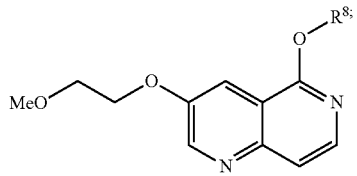
(III)

and (iv) acidifying the naphthyridine of Formula (III), under conditions sufficient to form 3-(2-methoxyethoxy)-1,6-naphthyridin-5(6H)-one ("NAPH"):

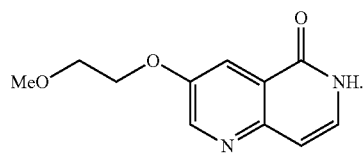 [SMILES: COCCOc1cnc2cc[nH]c(=O)c2c1]
(NAPH)

Still another aspect of the disclosure is a method including (i) admixing 3-(2-methoxyethoxy)-1,6-naphthyridin-5(6H)-one ("NAPH"):

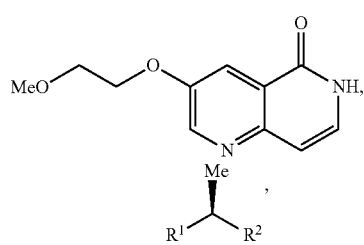
(NAPH)

and a base, under conditions sufficient to form NAPA:

(NAPA)

wherein $R^1$ is Br, Cl, I, or OTf, and $R^2$ is COOH or $C_{1-3}$alkyl ester, and when $R^2$ is $C_{1-3}$alkyl ester the method of forming the NAPA further comprises hydrolyzing the $C_{1-3}$alkyl ester to form an acid;

(ii) admixing the NAPA with 3-fluoro-2-hydrazinyl-5-(1-methyl-1H-pyrazl-4-yl)pyridine ("PYRH"):

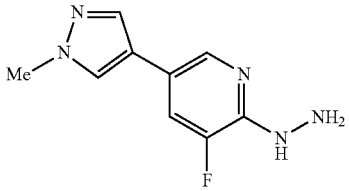
(PYRH)

and a coupling reagent, and under conditions sufficient to form (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ"):

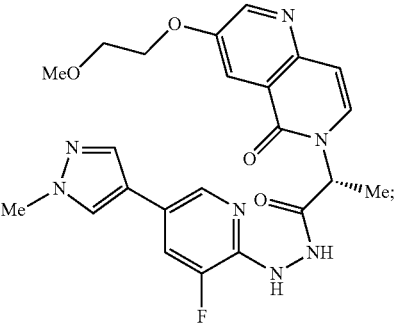
(HYDZ)

and (iii) reacting the HYDZ under conditions sufficient to form (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

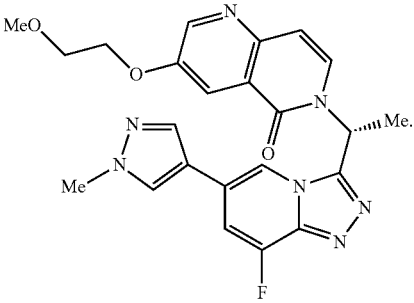
(A)

Further aspects and advantages will be apparent to those of ordinary skill in the art from a review of the following detailed description. While the methods disclosed herein are susceptible of embodiments in various forms, the description hereafter includes specific embodiments with the understanding that the disclosure is illustrative, and is not intended to limit the invention to the specific embodiments described herein. For the compositions and methods described herein, optional features, including but not limited to components, compositional ranges thereof, substituents, conditions, and steps, are contemplated to be selected from the various aspects, embodiments, and Examples provided herein.

DETAILED DESCRIPTION OF THE INVENTION

Disclosed herein is the preparation of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (Compound A), or a salt thereof (e.g., the HCl salt):

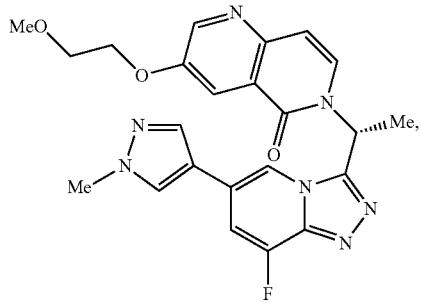

and the monohydrate form thereof:

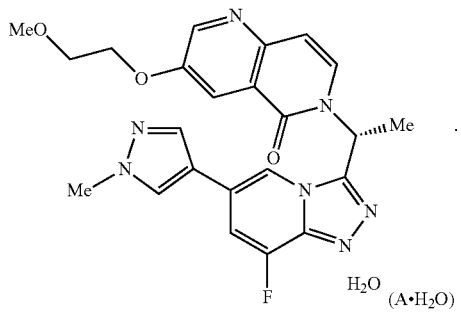

Compound A is advantageously prepared through the convergent synthesis of three active pharmaceutical ingredient (API) starting materials: 3-(2-methoxyethoxy)-1,6-naphthyridin-5(6H)-one ("NAPH"), 3-fluoro-2-hydrazinyl-5-(1-methyl-1H-pyrazol-4-yl)pyridine ("PYRH"), and an S-propionic acid or ester.

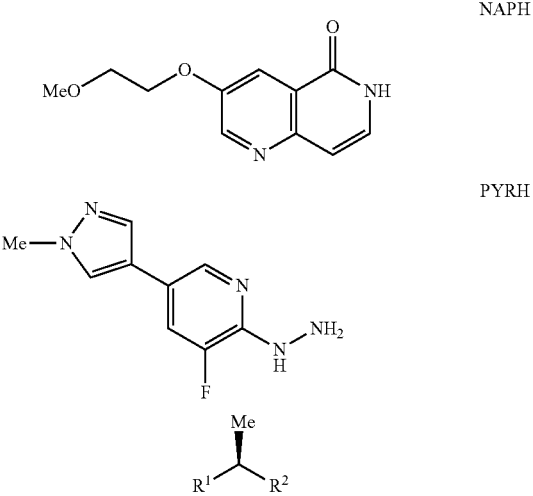

(S)-propionic acid/ester,
wherein
$R^1$ is Br, Cl, or I, and
$R^2$ is COOH or $C_{1-3}$alkyl ester The overall scheme for the preparation of Compound A is shown below. The optical purity of Compound A is controlled during the synthetic process by both the quality of the incoming starting materials and the specific reagents used for the transformations. Chiral purity is preserved during both the coupling reaction (the second step) and the dehydration reaction (the third step).

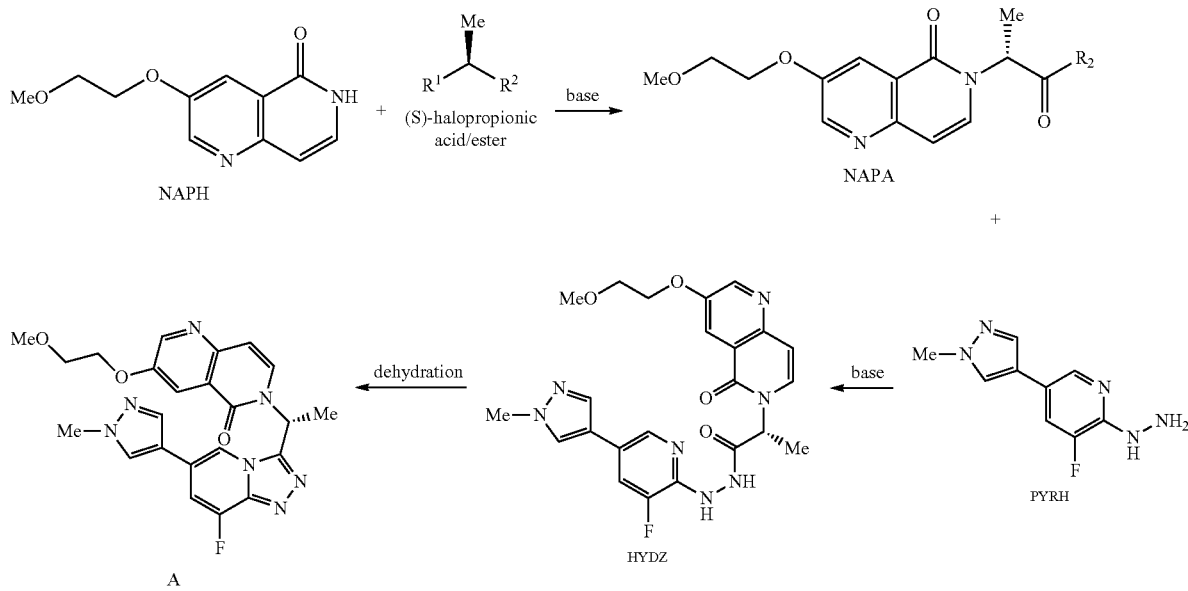

The method of preparing Compound A that is disclosed herein advantageously results in a robust, scalable, efficient process.

DEFINITIONS

Compounds may be identified either by their chemical structure and/or chemical name herein. When the chemical structure and chemical name conflict, the chemical structure is determinative of the identity of the compound herein. The compounds described herein may contain one or more chiral centers and/or double bonds and therefore may exist as stereoisomers such as double bond isomers isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

For the purposes of the present disclosure, "chiral compounds" are compounds having at least one center of chirality (i.e. at least one asymmetric atom, in particular at least one asymmetric C atom), having an axis of chirality, a plane of chirality or a screw structure.

It is believed the chemical formulas and names used herein correctly and accurately reflect the underlying chemical compounds. The present disclosure, however, provides more than the particular compounds, methods, or embodiments used by way of illustration. Thus it is understood that the formulae used herein, as well as the chemical names attributed to the correspondingly indicated compounds, illustrate embodiments and do not necessarily limit what is provided by the disclosure to any specific tautomeric form or to any specific optical or geometric isomer, unless specifically stated.

Unless otherwise indicated, terms and abbreviations used in this specification include the normal and customary meaning to those in the relevant field.

Particular abbreviations, as used in the specification, correspond to units of measure, techniques, properties, or compounds as follows:

DIPEA di-isopropylethylamine
DMAC N,N-dimethylacetamide
h hour(s)
HCl hydrochloric acid
$H_2O$ water
$HSO_3^-$ bisulfite
IPA isopropyl alcohol
Kg and/or kg kilogram
$K_2CO_3$ potassium carbonate
L and/or l liter
MeTHF 2-methyl tetrahydrofuran
M molar
MeCN acetonitrile
MeOH methanol
Min and/or min minutes
mL milliliter(s)
mM millimolar
mmol millimole(s)
$N_2$ nitrogen
$NaHCO_3$ sodium bicarbonate
$Na_2CO_3$ sodium carbonate
OTf Trifluoromethanesulfonate (triflate)
RT and/or rt room temperature
THF tetrahydrofuran
μm micrometer(s)

Where the term "alkyl" embraces linear or branched radicals having one to about twelve carbon atoms. Alkyl radicals include "lower alkyl" radicals having one to about six carbon atoms. Examples of such radicals include methyl, ethyl, n-propyl, isopropyl, n-butyl, isobutyl, sec-butyl, tert-butyl, pentyl, isoamyl, hexyl and the like. Also included are lower alkyl radicals having one or two carbon atoms. The term $C_n$ means the alkyl group has "n" carbon atoms. For example, $C_4$ alkyl refers to an alkyl group that has 4 carbon atoms. $C_{1-7}$alkyl refers to an alkyl group having a number of carbon atoms selected from any one within the entire range (i.e., 1 to 7 carbon atoms), as well as all subgroups (e.g., 1-6, 2-7, 1-5, 3-6, 1, 2, 3, 4, 5, 6, and 7 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group.

The term "aryl", alone or in combination, means a carbocyclic aromatic system containing one or two rings wherein such rings may be attached together in a fused manner. The term "aryl" embraces aromatic radicals, including, but not limited to, phenyl, naphthyl, indenyl, tetrahydronaphthyl, and indanyl. In certain embodiments, aryl is phenyl. Said "aryl" group may have 1 to 3 substituents such as lower alkyl, hydroxyl, halo, haloalkyl, nitro, cyano, alkoxy and lower alkylamino. Phenyl substituted with —O—$CH_2$—O— forms the aryl benzodioxolyl substituent. Unless otherwise indicated, an aryl group can be an unsubstituted aryl group or a substituted aryl group.

The term "heteroaryl" as used herein refers to monocyclic or polycyclic (e.g., fused bicyclic and fused tricyclic) aromatic ring systems, wherein one to four-ring atoms are selected from oxygen, nitrogen, or sulfur, and the remaining ring atoms are carbon, said ring system being joined to the remainder of the molecule by any of the ring atoms. Non-limiting examples of heteroaryl groups include, but are not limited to, pyridyl, pyrazinyl, pyrimidinyl, pyrrolyl, pyrazolyl, imidazolyl, thiazolyl, tetrazolyl, oxazolyl, isooxazolyl, thiadiazolyl, oxadiazolyl, furanyl, quinolinyl, isoquinolinyl, benzoxazolyl, benzimidazolyl, and benzothiazolyl. Unless otherwise indicated, a heteroaryl group can be an unsubstituted heteroaryl group or a substituted heteroaryl group.

The term "alkoxy" embrace linear or branched oxy-containing radicals each having alkyl portions of one to about ten carbon atoms. In certain embodiments, alkoxy radicals are "lower alkoxy" radicals having one to six carbon atoms. Examples of such radicals include methoxy, ethoxy, propoxy, butoxy and tert-butoxy. In certain embodiments, they are lower alkoxy radicals having one to three carbon atoms. Alkoxy radicals may be further substituted with one or more halo atoms, such as fluoro, chloro or bromo, to provide "haloalkoxy" radicals. In certain embodiments, they are lower haloalkoxy radicals having one to three carbon atoms. Examples of such radicals include fluoromethoxy, chloromethoxy, trifluoromethoxy, trifluoroethoxy, fluoroethoxy and fluoropropoxy.

The term "alkyl ester" as used herein refers to a group of the general Formula:

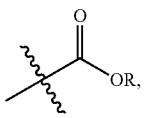

wherein R is an alkyl group.

The terms "enantiomeric excess" or "ee" refer to a measurement of purity used for chiral substances, and reflect the degree to which a sample contains one enantiomer in greater amounts than the other. A racemic composition (i.e., a composition having equal amounts of right- and left-handed enantiomers) has an ee of 0%, while a composition comprising pure enantiomer has an ee of 100%. A composition comprising 70% of one enantiomer and 30% of the other has an ee of 40%.

The term "ee erosion" refers to a decrease in the ee of a solution or composition.

The term "NAPA" refers to: (i) (R)-2-(3-(2-methoxyethoxy)-5-oxo-1,6-naphthyridin-6(5H)-yl)propanoic acid, (ii) a salt of (R)-2-(3-(2-methoxyethoxy)-5-oxo-1,6-naphthyridin-6(5H)-yl)propanoic acid, or (iii) both (i) and (ii) together.

The term "(S)-propionic acid/ester" refers to (i) a propionic acid with S stereochemistry, (i) a propionic ester with S stereochemistry, or (iii) both (i) and (ii) together.

Additional embodiments are disclosed herein. Disclosed embodiments illustrate various aspects that can be included in particular embodiments. It should be understood that examples, while indicating particular embodiments, are given by way of illustration only. Compounds which may be obtained by the novel methods described herein will be apparent to those of ordinary skill in the art, suitable procedures being described, for example, to provide a disclosed compound also describes how to obtain other triazolopyridines.

As the present disclosure's contribution is not limited to particular embodiments or aspects disclosed herein, the disclosure provides to one of ordinary skill in the art additional embodiments including changes and modifications to adapt to various usages and conditions. For example, changes and modifications to materials, methods of synthesis, or procedures described herein will be apparent to one of ordinary skill As used herein and in the appended claims, the singular forms "a," "an," and "the" include the plural reference unless the context clearly indicates otherwise. Thus, for example, a reference to "a compound" is a reference to one or more compounds and equivalents thereof known to those skilled in the art, and so forth. The term "comprising" is meant to be open ended, including the indicated element (e.g., component or step) but not excluding other elements.

When ranges are used herein for physical properties, such as molecular weight, or chemical properties, such as chemical formulae, all combinations and subcombinations of ranges and specific embodiments therein are intended to be included.

While the disclosure and description of embodiments illustrates the contribution over the prior art, it is not intended to restrict or in any way limit the scope of the appended claims to such detail(s). Additional advantages and modifications will readily appear to those skilled in the art. Therefore, the invention in its broader aspects is not limited to the specific details, representative apparatus and methods, and illustrative examples shown and described. Accordingly, departures may be made from such details without departure from the spirit or scope of the general inventive concept. Those skilled in the art will appreciate that numerous changes and modifications can be made to disclosed embodiments and that such changes and modifications are within the scope of the present disclosure.

Preparation of Compound A

In one aspect, provided herein is a method for preparing Compound A, salts of Compound A, and the monohydrate form of Compound A. Compound A can be prepared from the NAPH, PYRH, and S-propionic acid/ester starting materials in three steps. First, NAPH and S-propionic acid/ester undergo an $S_N2$ alkylation reaction to result in (R)-2-(3-(2-methoxyethoxy)-5-oxo-1,6-naphthyridin-6(5H)-yl)propanoic acid/ester. The S-propionic acid starting material produces (R)-2-(3-(2-methoxyethoxy)-5-oxo-1,6-naphthyridin-6(5H)-yl)propanoic acid ("NAPA") in one step. The S-propionic ester starting material first produces the ester analog of NAPA, and is subsequently hydrolyzed to form NAPA. During workup, the acid can optionally form a salt (e.g., HCl or 2-naphthalenesulfonic acid).

Step 1

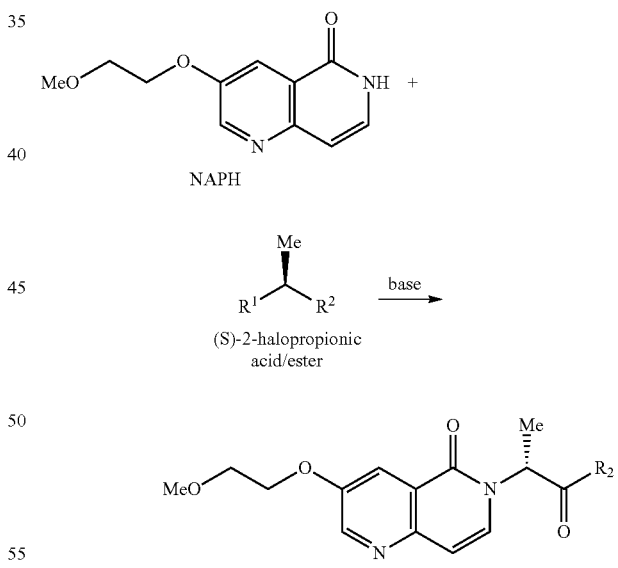

wherein $R^1$ is Br, Cl, I, or OTf; and $R^2$ is COOH or $C_{1-3}$alkyl ester, and when $R^2$ is $C_{1-3}$alkyl ester, the method of forming the NAPA or salt thereof further comprises hydrolyzing the $C_{1-3}$alkyl ester to form an acid.

Second, NAPA and PYRH are coupled together to form (R)—N'-(3-fluoro-5-(1methyl-1H-pyrazol-4-yl)pyridin-2-yl)-2-(3-(2-methoxyethoxy)-5-oxo-1,6-naphthyridin-6(5H) yl)propanehydrazide ("HYDZ").

Step 2

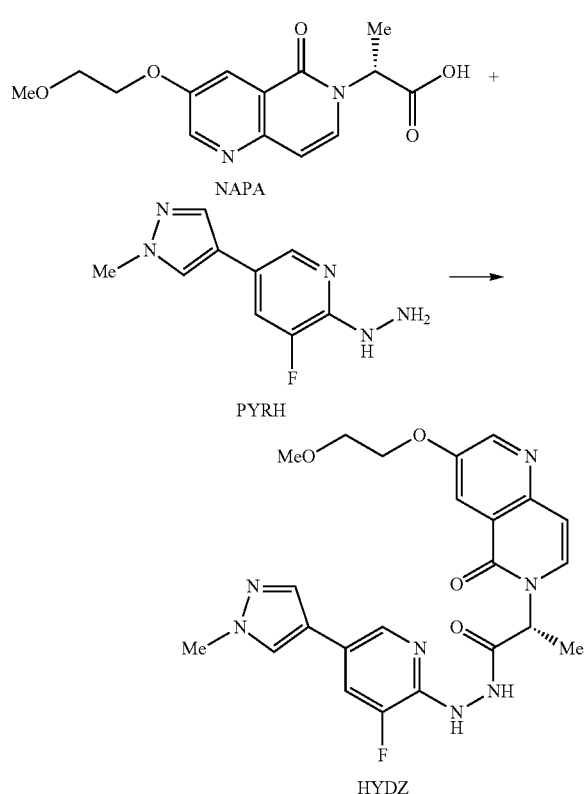

Third, HYDZ is dehydrated to form Compound A.

Step 3

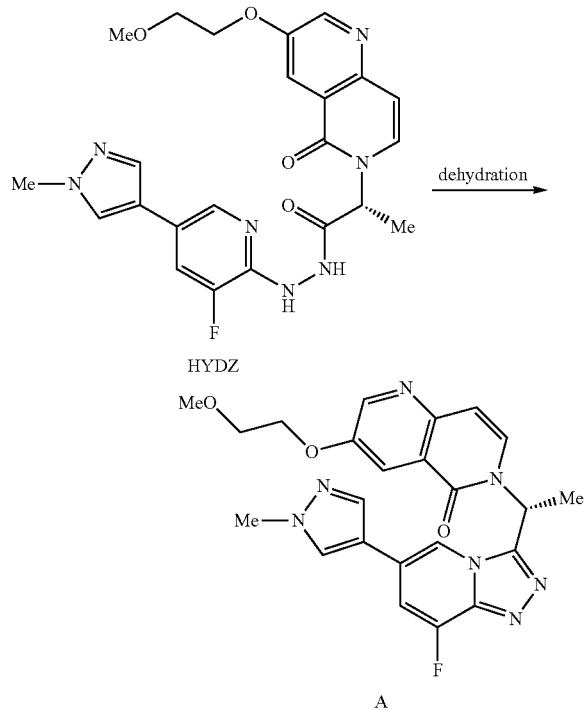

The free base form of Compound A can be crystallized as a salt or a monohydrate.

Step 1: Alkylation of NAPH to Form NAPA

The first step in the preparation of Compound A is the alkylation of NAPH to form NAPA. The NAPA product of the alkylation reaction is produced as a free base and is advantageously stable.

Thus, one aspect of the disclosure provides a method for preparing NAPA comprising admixing 3-(2-methoxyethoxy)-1,6-naphthyridin-5(6H)-one ("NAPH"):

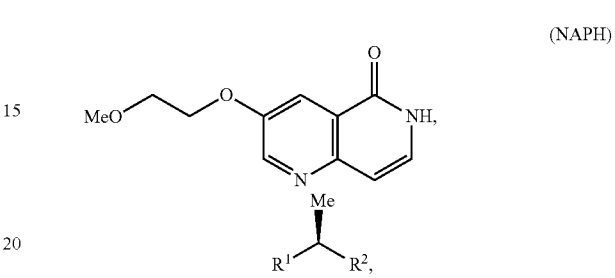

and a base, under conditions sufficient to form NAPA:

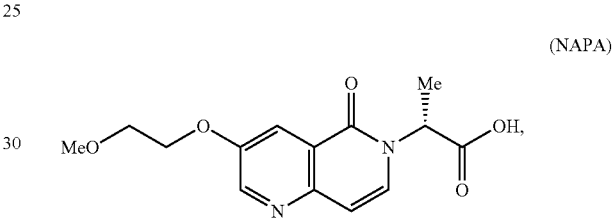

wherein $R^1$ is Br, Cl, I, or OTf; and
$R^2$ is COOH or $C_{1-3}$alkyl ester;
and when $R^2$ is $C_{1-3}$alkyl ester, the method of forming the NAPA or salt thereof further comprises hydrolyzing the $C_{1-3}$alkyl ester to form an acid.

The compound,

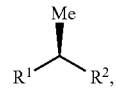

represents an (S)-propionic acid and/or (S)-propionic ester ("(S)-propionic acid/ester"). When

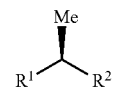

is an acid (i.e., $R^2$ is COOH), NAPA is formed in one step:

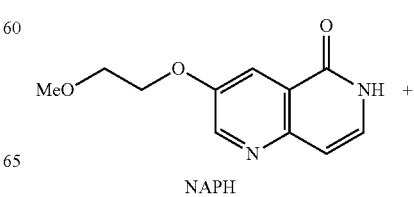

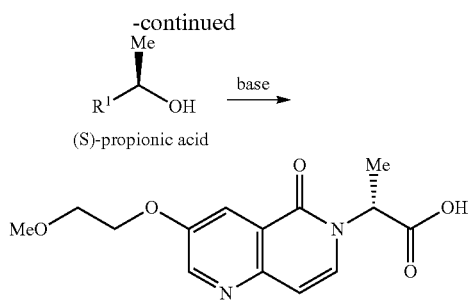

When

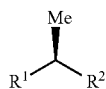

is an ester (i.e., $R^2$ is $C_{1-3}$ alkyl ester), then the NAPA ester analog is formed, which can be hydrolyzed to form NAPA.

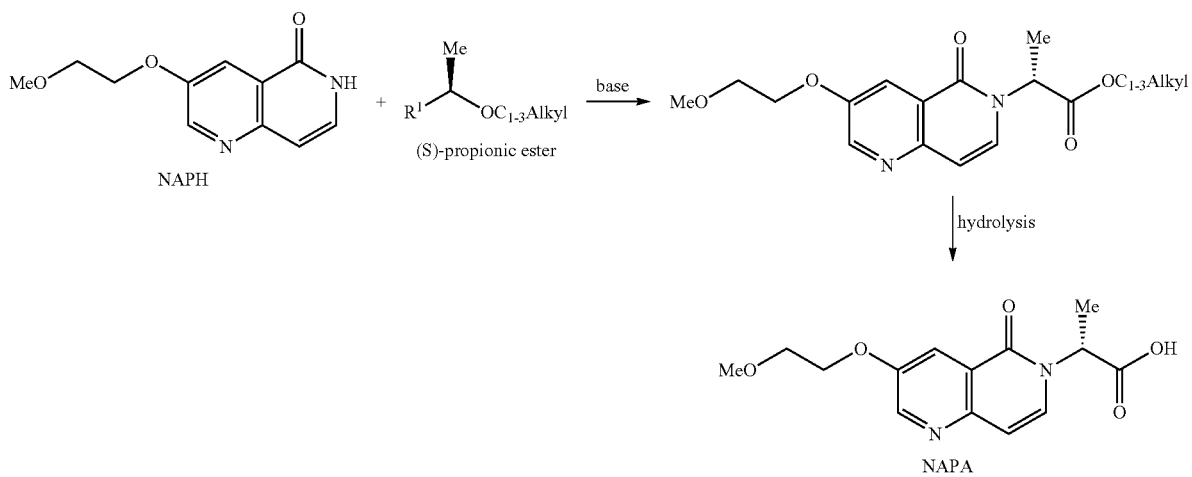

The $S_N2$ alkylation of NAPH to form NAPA occurs with an inversion of stereochemistry of the (S)-propionic acid/ester starting material to form the R enantiomer of NAPA. Therefore, the synthesis of NAPA disclosed herein is advantageously stereoselective. The stereospecific alkylation of naphthyridinones, such as NAPH, however, is challenging because naphthyridinones are sterically hindered, they have reduced nucelophilicity, the starting material and the product are both sensitive to epimerization, and they have two nucleophiles (the nitrogen and oxygen atoms of the amide; therefore, either O-alkylation or N-alkylation could potentially occur). Therefore, disclosed herein is a method for stereospecifically alkylating a NAPH in good yield and with high optical purity.

The degree of alkylation of a napthyridinone, as well as the N/O alkylation selectivity (N-alkylation versus O-alkylation), can depend on the base used in the reaction. The base used for the alkylation reaction disclosed herein can be a strong, inorganic base, for example a metal tert-butoxide with a Lewis acid cation. As specific examples, the base can be KOtBu, NaOtBu, LiOtBu, Mg(OtBu)$_2$, Al(OtBu)$_3$, NaOSiMe$_3$, Cs$_2$CO$_3$, potassium bis(trimethylsilyl)amide ("KHMDS"), sodium bis(trimethylsilyl)amide ("NaHMDS"), lithium bis(trimethylsilyl)amide ("LiHMDS"), or combinations thereof. In one aspect, the base can be selected from KOtBu, NaOtBu, NaOSiMe$_3$, Cs$_2$CO$_3$, LiOtBu, Mg(OtBu)$_2$, Al(OtBu)$_3$, or combinations thereof; in another aspect the base can be Cs$_2$CO$_3$.

The base can include magnesium. Use of a base that includes Mg advantageously results in higher reactivity and lower ee erosion. Without being bound by any particular theory, magnesium is oxophilic and selectively binds to the oxygen atom of the amide on NAPA (instead of to the nitrogen atom of the amide). As a result, the nitrogen atom on the amide of NAPA is more reactive in the alkylation reaction, and the reaction is able to achieve high N-alkylation selectivity. Also without being bound by any particular theory, the magnesium interacts with the carboxylate of the starting material. Therefore, a (S)-propionic acid starting material reacts more quickly than a (S)-propionic ester starting material.

The base can be a combination of NaOtBu and Mg(OtBu)$_2$ and/or KOtBu and Mg(OtBu)$_2$. These combinations, particularly KOtBu and Mg(OtBu)$_2$, result in excellent N/O selectivity and high optical purity for the $S_N2$ alkylation reaction. Certain weak bases have been found to be inactive, including iPr$_2$NEt. Certain metal oxide bases have been found to result in incomplete conversion, variable optical purity of product, and low N/O selectivity.

In regard to the (S)-propionic acid/ester starting material, $R^1$ can be Br, Cl, I, or OTf. In one aspect, $R^1$ can be Br or Cl. For example the (S)-propionic acid/ester can include

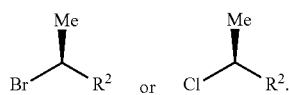

In another aspect, $R^1$ is I or OTf.

$R^2$ of the (S)-propionic acid/ester starting material can be COOH. In these embodiments the (S)-propionic acid/ester can be

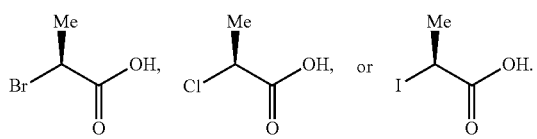

For example the (S)-propionic acid can be

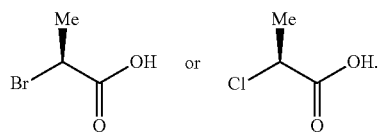

The acid form of the (S)-propionic acid/ester starting material is advantageous because formation of NAPA can be performed in one step, and because the carboxyl group of the starting material can interact with a magnesium base.

R² of the (S)-propionic acid/ester can be $C_{1-3}$ alkyl ester, such as OMe, OEt, OPr, or OiPr. In these embodiments, the (S)-propionic acid/ester can be

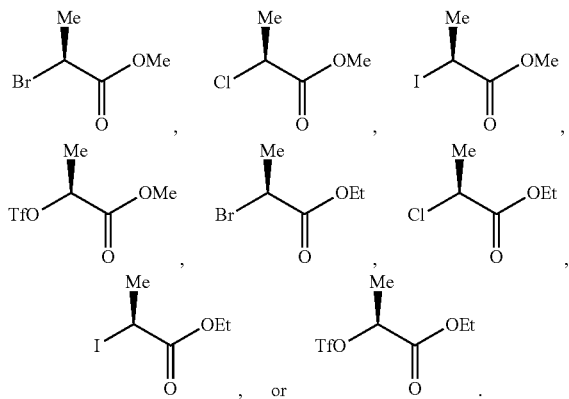

For example the (S)-propionic acid can be

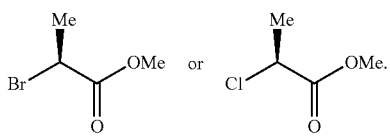

When (S)-propionic ester is used as the starting material, the resulting ester product is hydrolyzed to produce NAPA (the acid) in a second step. The hydrolysis can occur in acidic conditions, such as in the presence of HCl, AcOH, or a combination thereof. Alkyl acetate can form in situ during the hydrolysis process, but can be removed to achieve good conversion (e.g., greater than about 90%).

The alkylation reaction can occur in any suitable solvent. The solvent can be, e.g., an ether solvent (e.g., tetrahydrofuran ("THF"), 2-methyltetrahydrofuran, tetrahydropyran), toluene, or acetonitrile.

The reaction to form NAPA can occur at any suitable temperature. For example, the reaction can occur at a temperature in a range of 20° C. to 80° C., or 25° C. to 60° C., or 25° C. to 45° C., or 25° C. to 35° C. A lower temperature is more optimal for decreasing ee erosion.

Generally, the alkylation reaction can include the alkylation of NAPH with (S)-2-bromopropionic acid or (S)-2-chloropropionic acid in THF, using NaOtBu/Mg(OtBu)₂ or KOtBu/Mg(OtBu)₂ as base. In these embodiments, the alkylation reaction can occur within the ranges described above, or at a temperature of about 25 to 35° C. The ratio of magnesium base to the sodium or potassium base can be in a range of about 1.5:1 to 2.5:1, for example about 2:1. In one class of embodiments, the ratio of NAPH to (S)-2-chloropropionic acid is about 1:1 to about 1:2.5, or about 1:1.5.

The free base NAPA product can be contacted with a suitable acid or a base to form a salt. For example, the free base can be contacted with an acid selected from HCl, HBr, a sulfonic acid, a diisopropylamine, or a potassium cation. The sulfonic acid can be, e.g., 2-naphthalenesulfonic acid ("NSA"), 1-naphthalenesulfonic acid, or m-xylenesulfonic acid, p-toluene sulfonic acid, benzene sulfonic acid, 2-nitrobenzenesulfonic acid, 2,5-dichlorobenzene sulfonic acid, (−)-10-camphorsulfonic acid, (+)-camphor-10-sulfonic acid, p-chlorobenzene sulfonic acid, methanesulfonic acid, or combinations thereof. For example, NAPA can be contacted with aqueous 2-naphthalenesulfonic acid to form the salt.

The (S)-propionic acid/ester starting materials are well known in the art, and are commercially available in high enantiomeric purity from a number of vendors (e.g., from SigmaAldrich). The triflate starting material can be prepared by reaction of methyl lactate with Tf₂O pyridine in dichloromethane. The pyridinium triflate salt by-product crystallizes from the reaction solution upon addition of methyl tert-butyl ether, and can be removed by filtration. The resulting filtrate has a purity suitable for use in the alkylation reaction. The optical purity of the triflate product is high (e.g., greater than 98% ee), but can decrease over time.

The resulting NAPA salt can be purified by any suitable purification method, for example by crystallization, as described in further detail in the Examples section.

In view of the teachings herein, the alkylation of NAPH can be high yielding (e.g., 95-97% crude and 80-90% isolated), and the NAPA product can have excellent purity (e.g., greater than 98%). For example, the alkylation of NAPH to form NAPA, can have a yield of at least about 80%, at least about 90%, at least about 95%, or at least about 97%. The purity the NAPA product can be at least about 95%, at least about 97%, at least about 99% or at least about 99.5%. Further, the reaction can result in a NAPA product having high optical purity (e.g., 90-97% ee). The optical purity of NAPA can be at least about 90%, at least about 95%, at least about 97%, at least about 99%, or at least about 99.5% ee.

Step 2: Coupling of NAPA and PYRH to Form HYDZ

The second step of the preparation of Compound A is the coupling of NAPA with PYRH to form HYDZ.

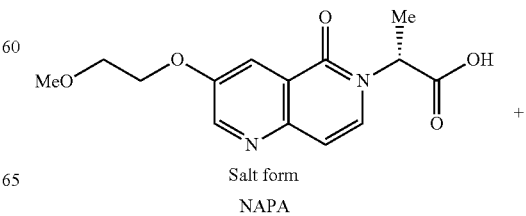

Salt form
NAPA

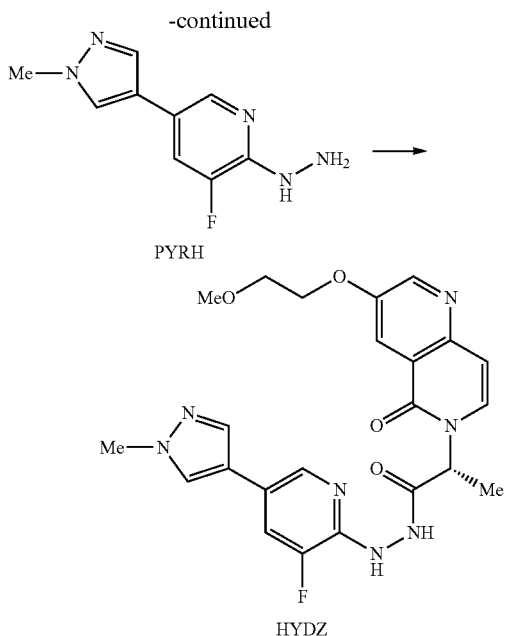

The coupling of NAPA and PYRH to form HYDZ occurs by reacting the carboxyl group on NAPA with the amino group on PYRH via a coupling agent to form an amide bond. Methods of coupling a carboxyl group and an amino group to form an amide bond are well known to those skilled in the art. See, e.g., Hermanson, Bioconjugate Techniques, 2$^{nd}$ ed, (2008).

Thus, another aspect provided herein is a method comprising reacting (R)-2-(3-(2-methoxyethoxy)-5-oxo-1,6-naphthyridin-6(5H)-yl)propanoic acid or a salt thereof ("NAPA") with 3-fluoro-2-hydrazinyl-5-(1-methyl-1H-pyrazl-4-yl)pyridine ("PYRH") and a coupling reagent, and under conditions sufficient to form HYDZ.

NAPA can be used in its free base (i.e., zwitterionic form) for the coupling reaction.

NAPA can be used in a salt form for the coupling reaction. The salt form of NAPA can include HCl, HBr, a sulfonic acid, a diisopropylamine, or a potassium cation. The sulfonic acid can be e.g., 2-naphthalenesulfonic acid ("NSA"), 1-naphthalenesulfonic acid, or m-xylenesulfonic acid, p-toluene sulfonic acid, benzene sulfonic acid, 2-nitrobenzenesulfonic acid, 2,5-dichlorobenzene sulfonic acid, (−)-10-camphorsulfonic acid, (+)-camphor-10-sulfonic acid, p-chlorobenzene sulfonic acid, methanesulfonic acid, or combinations thereof.

Generally, in the coupling reaction NAPA can include HCl or a sulfonic acid (e.g., NAPA/HCl or NAPA/2-naphthalenesulfonic acid). The sulfonic acids (e.g., 2-naphthalenesulfonic acid) unexpectedly resulted in an ee upgrade during isolation of the HYDZ.

The coupling reaction can proceed using any suitable amide coupling reagent. For example, the coupling reagent can be a carbodiimide reagent, a phosphonium reagent, a uronium reagent, an immonium reagent, an imidazolium reagent, an organophosphorus reagent, an acid chloride reagent, a chloroformate reagent, or a pyridinium reagent. See, e.g., Han & Kim, Tetrahedron Report 60:2447-2467 (2004); Montalbetti andn Falque, Tetrahedron 61:10827-10852 (2005).

The carbodiimide can be N,N'dicyclohexylcarbodiimide ("DCC"), 1,3-diisopropylcarbodiimide ("DIC"), 1-ethyl-3-(3-dimethylaminopropyl)carbodiimide ("EDC"), or and isopropylcarbodimide ("CIC"), for example.

The phosphonium reagent can be (benzotriazol-1-yloxy)tris(dimethylamino)phosphonium hexafluorophosphate ("BOP") or benzotriazol-1-yl-oxytripyrrolidinophosphonium hexafluorophosphate ("PyBOP"), for example.

The uronium reagent can be 1-[Bis(dimethylamino)methylene]-1H-1,2,3-triazolo[4,5-b]pyridinium 3-oxid hexafluorophosphate ("HATU") or O-(Benzotriazol-1-yl)-N,N,N',N'-tetramethyluronium hexafluorophosphate ("HBTU"), for example.

The imidazolium reagent can be 1,1'-carbonyldiimidazole ("CDI"), for example.

The acid chloride reagent can be pivaloyl chloride or 2, 4, 6-trimethylbenzoyl chloride, for example.

The chloroformate reagent can be ethyl chloroformate or isobutyl chloroformate, for example.

In one aspect, the coupling reagent can be selected from HATU and/or EDC. Use of EDC is advantageous because it does not have racemization or yield problems. For example, CDI can result in high levels of epimerization in the hydrazide product; ethyl and chloroformate, iso-butylchloroformate, pivaloyl chloride, and 2, 4, 6-trimethylbenzoylchloride each can result in racemization and decreased yield. In another aspect, the coupling reagent can be selected from HBTU, BOP and/or DCC.

The coupling reagent can be present in an amount in a range of about 1.0 equivalent to about 1.8 equivalents, or about 1.0 equivalents to about 1.5 equivalents (e.g., 1.1, or 1.2, or 1.3, or 1.4, or 1.5 equivalents). In one aspect, the coupling reagent is present in an amount of about 1.2 equivalents. In another aspect, the coupling reagent is present in an amount of about 1.3 equivalents.

The coupling reaction can be performed in the presence of a coupling additive. Coupling additives are known in the art and any suitable one can be used for the formation of HYDZ. For example, the coupling additive can be a benzotriazole. Examples of coupling additives include benzotriazoles, dicarboximides, and succinimides. In one aspect the coupling additives include one or more of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), or 1-hydroxy-7-azabenzotriazole ("HOAt"). In another aspect the coupling additive comprises HOBt; in still another aspect, the coupling additive comprises HOSu.

The coupling reaction can optionally occur in the presence of a base, for example, a tertiary amine base. Suitable bases for coupling reactions are well known in the art. In one aspect, the base is selected from N,N-diisopropylethylamine ("DIEA") triethylamine ("TEA"), N-methylmorpholine ("NMM"), and combinations thereof. In one class of embodiments, for example when NAPA is used in its zwitterionic form, base can be absent from the coupling reaction. In other classes of embodiments, a base can be included in the coupling reaction.

The base can be present in an amount of at least about 1 equivalent, for example. Advantageously, when the base is present in an amount of greater than 1 equivalent, the racemization can be minimized to less than 1% ee. When the base is present in an amount of less than 1 equivalent, racemization of greater than 2% ee was observed.

The coupling reaction can occur in an aprotic solvent, for example acetonitrile, dichloromethane, tetrahydrofuran, dimethylacetamide ("DMAc"), or a combination thereof. In one aspect the aprotic solvent comprises DMAc. DMAc also is advantageously a good solvent for recrystallization and isolation of the HYDZ product. In another aspect, the aprotic solvent comprises acetonitrile.

The coupling reaction can occur at any temperature that allows the reaction to proceed with good conversion. For example, the coupling reaction can occur at a temperature in a range of 10° C. to 30° C., or 15° C. to 25° C., or 20° C. The coupling reaction also can occur at a temperature in a range of about 0° C. to 10° C., or 2° C. to 8° C., or 5° C.

In one type of embodiment, the coupling reaction can be performed using EDC as the coupling reagent, HOBt as the coupling additive, DIEA as the base, and DMAc as the solvent. The order of addition of the reagents can affect product yield, purity, and optical purity. Thus, the order of addition can be: (1) NAPA/2-naphthalenesulfonic acid, DMAc, HOBt; (2) DIEA, (3) PYRH, (4) EDC. In experiments, when NAPA was added last, poor conversion was shown to result due to reaction of EDC and PYRH. In experiments, when PYRH was added last, significant racemization was observed. In experiments, when DIEA was added after PYRH, a thick reaction mixture resulted. No coupling reaction occurred in the absence of EDC. Therefore, EDC can be added last to start the reaction. In these embodiments, the NAPA/2-naphthalenesulfonic acid, HOBt, and DMAc can be present in an amount of about 1.0 equivalent, about 1.0 equivalent, and about 4.6 volumes, respectively, for example. The DIEA can be present in an amount of about 1.0 equivalent to about 1.2 equivalents (e.g., 1.05 equivalents), for example. The PYRH can be present in an amount of about 1.1 equivalents, for example. The EDC can be present in an amount of about 1.0, or 1.1, or 1.2, or 1.3, or 1.4, or 1.5 equivalents, for example (e.g., 1.2 or 1.3 equivalents). The EDC can be added slowly to the reaction mixture (e.g., 4 portions over 1 hour).

HYDZ can advantageously crystallize directly from the reaction solution upon addition of water in high optical purity.

Further, the HYDZ product can be purified by any suitable method known in the art. For example, the HYDZ product can be crystallized in water and DMAc, as further described in the Examples section.

In view of the teachings herein, the coupling reaction can be made to result in a stable HYDZ product in good yield (e.g., greater than 95% crude, and about 78%-84% isolated). For example, formation of HYDZ from NAPA and PYRH can result in a yield of at least about 75%, at least about 85%, at least about 90%, or at least about 95%. The loss from crude yield to isolated yield is due to a built-in crystallization that allows an upgrade in ee from greater than 99% to about 100%. Therefore, the optical purity of HYDZ can advantageously be at least about 99%, at least about 99.5%, at least about 99.7%, at least about 99.9%, or about 100% ee. The purity of HYDZ that results from coupling NAPA and PYRH can be excellent (e.g., at least about 95%, at least about 97%, at least about 99% at least about 99.5%, or about 100%).

Step 3: Dehydration of HYDZ to Form Compound A

The third step of the preparation of Compound A is the dehydration of HYDZ to form Compound A:

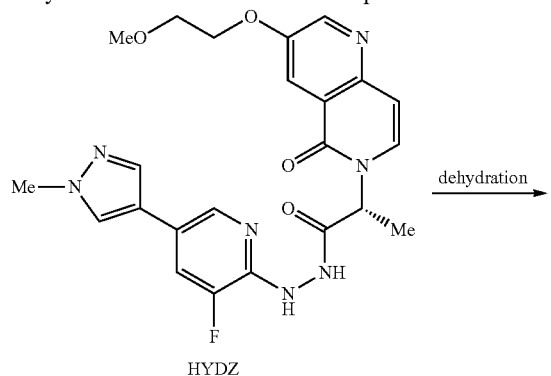

HYDZ dehydration →

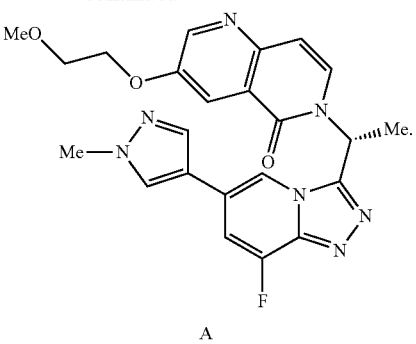

A

In particular, the third step of the preparation of Compound A is the dehydration of the hydrazine on HYDZ to form Compound A, a compound having a pyrazolopyridine bicycle core. Compound A can be isolated as a salt form (e.g., HCl salt) or in a monohydrate form, and is stable to air, moisture, and elevated temperature.

Thus, another aspect provided herein is a method that includes reacting (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ") under conditions sufficient to form (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A").

A number of reagents can be used for the dehydration reaction. However, HYDZ has a chiral center adjacent to the carbonyl carbon, which is particularly susceptible to epimerization. Therefore, retaining the chiral center of HYDZ during the dehydration can be a challenge. Disclosed herein are methods for performing the dehydration of HYDZ to form Compound A, while retaining the chiral center of HYDZ.

Route 1: Thiophosphetane Mediated Dehydration

HYDZ can be dehydrated by contacting it with a thiophosphetane compound. The thiophosphetane compound can be a 2,4-bis(aryl)-1,3-dithia-2,4-diphosphetane 2,4-disulfide compound, for example. With heating, the thiophosphetane compound can undergo a ring opening reaction to form two reactive dithiophosphine ylides, as shown by the partial structures below. See Lawson et al., Tet. Lett 41:4533-4536 (2000) and Fehrentz et al, Tet Lett 47:7591-7594 (2006)).

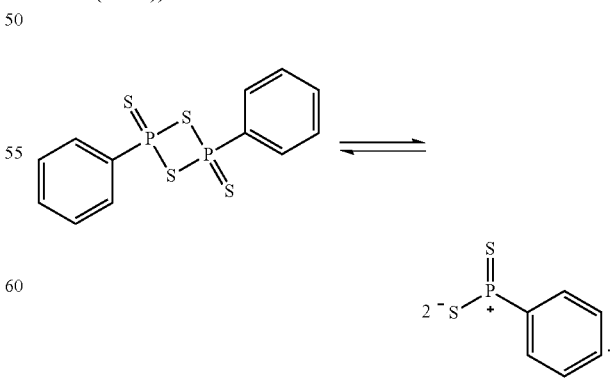

The 2,4-bis(aryl)-1,3-dithia-2,4-diphosphetane 2,4-disulfide compound can be Lawesson's reagent or Belleau's reagent:

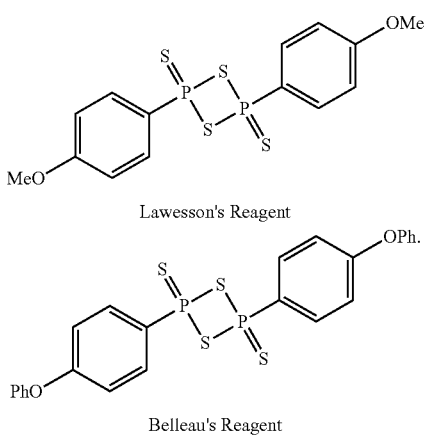

Lawesson's Reagent

Belleau's Reagent

In one aspect, Lawesson's reagent can be used; in another aspect, Belleau's reagent can be used.

The formation of Compound A by contacting HYDZ with a thiophosphetane compound can have several advantages. The dehydration can occur quickly, with selectivity for the desired product. The selectivity is due to the reactive, oxophilic 3-coordinate P(III) reagent that forms in solution. The pH of the reaction solution is low; therefore, the dehydration occurs with minimal erosion of optical purity. Further, the dehydration by-products can be easily removed, and the dehydration can advantageously result in a high yield.

Several reaction conditions can affect the conversion of the dehydration reaction and the optical purity of Compound A, e.g., the temperature of the reaction, the order of addition of the reagents, the method of addition, and the equivalents of the thiophosphetane compound.

For example, the temperature of the dehydration reaction can be in a range of 35° C. to 70° C., or 40° C. to 60° C., or 45° C. to 55° C. When the temperature of the dehydration reaction is 45° C. to 55° C. (e.g., 50° C.), no gummy slurry exists, and good optical purity results. Therefore, the dehydration reaction can be allowed to age at about 45° C. to 55° C., until the reactive intermediates are consumed, which is typically several hours (e.g., at least 2 hours, at least 3 hours, or at least 4 hours). When the reactive intermediates are not sufficiently consumed, they can persist into the isolation step and trigger decomposition of Compound A (e.g, HCl decomposition) via removal of the methoxyethyl side chain.

The dehydration reaction can be performed by making a slurry of the thiophosphetane compound (e.g., in acetonitrile), and adding the HYDZ to the slurry. When the HYDZ is added to a slurry of thiophosphetane compound, no or little loss of optical purity of the resulting Compound A results. Alternatively the thiophosphetane compound can be added to a slurry of HYDZ. In an example of this type of embodiment, however, the optical purity of Compound A was found to be lower.

The HYDZ can be added to the thiophosphetane slurry in portions or as a slurry itself.

The thiophosphetane compound can be present in the dehydration reaction in an amount of at least about 0.4 equivalents, or at least about 0.45 equivalents, or at least about 0.5 equivalents, for example, or an amount in a range of about 0.4 equivalents to about 0.65 equivalents, or about 0.45 equivalents to about 0.65 equivalents, or about 0.5 equivalents to about 0.55 equivalents. For example, the thiophosphetane can be present in an amount of at least about 0.5 equivalents, or a range of about 0.5 equivalents to about 0.55 equivalents.

For example, the dehydration reaction can be performed by making a slurry of about 0.5 to about 0.6 equivalents of the thiophosphetane compound (e.g., 0.52 equivalents) in acetonitrile at about 20° C., adding HYDZ in portions to the slurry over one or two hours, and heating the resulting composition to about 50° C. until about 99% consumption of the HYDZ occurs. Therefore, in one aspect, the dehydragtion reaction is performed by making a slurry of the thiophosphetane compound and adding HYDZ to it.

In another aspect, the dehydration reaction can be performed by mixing the thiophosphetane compound, HYDZ, and solvent together, and then heating the resulting composition, without using a slurry.

The crystalline free base monohydrate form of Compound A can be isolated directly from the dehydration reaction solution. A water-rich crystallization solvent with pH 7 or greater (e.g., an acetonitrile/water solution having about 80% to about 90% water) can quench any residual thiophosphetane compound, facilitate removal of thiophosphonic acid by-products as a salt, and facilitate removal of the minor enantiomer.

For example, the free base monohydrate form of Compound A can be isolated by concentrating the reaction solution (e.g., to about three volumes or less), and then adding to the reaction solution $K_2CO_3$ (e.g., about 1.1 equivalents of a 10 wt. % solution) along with water (e.g., about four volumes). The resulting solution can be seeded with the monohydrate form of Compound A (e.g., about 1 mol %), aged (e.g., for about 1 hour), introduced to additional water (e.g., about four volumes), and aged (e.g., until a supernatant concentration of less than about 8 mg/mL is obtained). The resulting crystals of the free base monohydrate form of Compound A advantageously meet the requisite purity requirements for pre-clinical and clinical use (e.g., greater than about 99.5% purity and greater than about 99.9% ee). For example, the purity can be at least about 99.5%, or at least about 99.7%, or at least about 99.9%, or about 100%; and the optical purity can be at least about 99.9% or about 100%. Therefore, they do not need to be recrystallized. However, the crystals can be recrystallized to further improve purity. Formation of the monohydrate form of Compound A is further described in the Examples section.

In other embodiments, Compound A can be isolated as a salt, e.g. a pharmaceutically-acceptable salt. Thus, provided herein is a method for preparing a salt of Compound A comprising contacting Compound A with an acid under conditions sufficient to form the salt of Compound A. The acid can be any suitable acid. For example, the acid can be selected from the group consisting of hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, and maleic acid. The salt of Compound A can be prepared by subjecting the reaction solution to a workup, and adding concentrated acid to the resulting solution, optionally seeding the solution with a salt of Compound A, and adding antisolvent to the optionally seeded solution.

The HCl salt of Compound A, for example, can be prepared by subjecting the reaction solution to a workup (e.g., a $K_2CO_3$, as described above), and then adding concentrated HCl to the quenched solution. The resulting solution can optionally be seeded with the HCl salt of Compound A, and antisolvent can be added to the solution to initiate the crystallization. In particular, the seeded solution can be aged at elevated temperature (e.g., 70° C.) for a period of time (e.g., at least about 15 minutes) to ensure the seed takes effect, and then cooled (e.g., to about 20° C.) over a period of about an hour, before antisolvent (e.g., heptane) is added to the cooled solution for aging at the cooled temperature. The resulting crystals of the HCl salt of compound A can be isolated and dried. Formation of the HCl salt of Compound A is further described in the Examples section.

The dehydration reaction of HYDZ using a thiophosphetane compound can result in a high yield of Compound A or a salt thereof (e.g., greater than 99% crude, and about 88% isolated). For example, the yield can be at least about 80%, at least about 90%, at least about 95%, or at least about 99%. Further, the purity of Compound A or a salt can be at least about 99%, at least about 99.5%, or at least about 99.7%. Although HYDZ has a chiral center adjacent to its reactive carbonyl carbon, dehydration of HYDZ using a thiophosphetane compound produces Compound A, or a salt thereof, in high optical purity. For example, the optical purity of Compound A, or a salt thereof, can be at least about 98%, at least about 99%, at least about 99.5%, or at least about 99.9% ee.

The thiophosphetane dehydration of HYDZ to form Compound A, a salt thereof, or the monohydrate form is further described in the Examples section.

Route 2: Phosphorous (V)-Mediated Dehydration

HYDZ can be dehydrated by contacting it with a phosphorus (V) dehydrating agent.

The dehydrating agent can be, e.g., a phosphinyl halide or a phosphoryl halide compound. The dehydrating agent can have a structure:

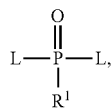

wherein each L independently is $C_{1-6}$alkyl, O—$C_{1-6}$alkyl, aryl, O-aryl, Cl, Br, or I; and $R^1$ is Cl, Br, or I.

For example, each L of the dehydrating agent can independently be a $C_{1-4}$alkyl group (e.g., Me, Et, Pr, iPr, n-Bu, s-Bu, i-Bu, or t-Bu), or a O—$C_{1-4}$alkyl group (e.g., OMe, OEt, OPr, OiPr, O-n-Bu, O-s-Bu, O-i-Bu, or O-t-Bu). Each L also can be an aryl group, for example phenyl, or an O-aryl group, for example O-phenyl. Each L also can be a halogen (e.g., Br, Cl, or I). In embodiments, one L can be a $C_{1-4}$alkyl group, and the other L can be an aryl group. In other embodiments, each L is phenyl. $R^1$ can be Cl, Br, or I. In one aspect, $R^1$ is Cl. In another aspect, $R^1$ is Br. For example, the dehydrating agent can be diphenylphosphinyl chloride ($Ph_2P(O)Cl$); in another example the dehydrating agent can be $POCl_3$.

The dehydrating agent can be present in an amount of about 1.5 equivalents to about 3.5 equivalents, or about 2.0 equivalents to about 3.0 equivalents (e.g., 2.5 equivalents).

The base can be any base capable of effecting the desired dehydration reaction. Pyridine bases can be used. For example, the base can be selected from 2,4-lutidine, 2,4,6-collidine, or a combination thereof. The base can be present in the reaction mixture in an excess. For example, the base can be present in an amount that is at least about 0.2 equivalents greater than the amount of the dehydrating agent. The base can be present in an amount of about 2.5 to about 4.0 equivalents, or about 2.5 to about 3.5 equivalents, for example.

The solvent can be any solvent in which the dehydration reaction can occur with good conversion and optical purity. For example, the solvent can be an amide, sulfolane, or nitrile solvent. The solvent can be, e.g., N-methyl-2-pyrrolidone ("NMP"), dimethylacetamide ("DMAc"), acetonitrile, propionitrile, and combinations thereof.

The dehydration reaction can occur at an elevated temperature, such as greater than about 60° C., greater than about 70° C., or greater than about 80° C., up to about 90° C. The reaction can occur at the reflux temperature of the reaction solution, e.g. about 83° C. to about 86° C. in some embodiments.

Upon completion of the reaction, it can be quenched (e.g., with $K_2CO_3/KCl$), as further described in the examples section.

Compound A can be isolated from the quenched solution as a salt, as described in the previous section. The salt can be the hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, or maleic acid salt, and combinations thereof, for example. In one aspect, the salt is the hydrochloric acid salt. Generally, concentrated HCl can be added to the quenched solution containing Compound A, the resulting solution can be seeded with the HCl salt of Compound A, and antisolvent can be added to the solution to initiate the crystallization. In particular, the seeded solution can be aged at elevated temperature (e.g., 70° C.) for a period of time (e.g., at least about 15 minutes) to ensure the seed takes effect, and then cooled (e.g., to about 20° C.) over a period of about an hour, before antisolvent (e.g., heptane) is added to the cooled solution for aging at the cooled temperature. The resulting crystals of the HCl salt of compound A can be isolated and dried. Formation of the HCl salt of Compound A is further described in the Examples section.

In view of the teachings herein, the dehydration reaction of HYDZ using a phosphorous (V) dehydrating agent to form Compound A can occur with good yield, as well as subsequent isolation of a salt of Compound A, as described herein. For example, the yield of the salt of Compound A can be at least about 85%, at least about 90%, at least about 95%, or at least about 99%. Further, the purity of the salt of Compound A can be at least about 88%, at least about 90%, or at least about 95%. Using a phosphinyl halide compound can produce the a salt of Compound A in high optical purity (e.g., greater than 99.5% ee). For example, the optical purity of a salt of Compound A can be at least about 99%, at least about 99.5%, at least about 99.8%, or at least about 99.9% ee.

The phosphinyl halide dehydration of HYDZ to form a salt (e.g., the HCl salt) of Compound A is further described in the Examples section.

Route 3: Mitsunobu-Mediated Dehydration

HYDZ can be dehydrated by subjecting it to Mitsunobu conditions. For example, HYDZ can be dehydrated by contacting it with a phosphine

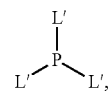

wherein each L' independently is an alkyl, aryl, or heteroaryl group; and an oxidant.

For example, each L' of the phosphine independently can be a $C_{1-6}$alkyl group, or a $C_{1-4}$alkyl group (e.g., Me, Et, Pr, iPr, n-Bu, s-Bu, i-Bu, or t-Bu). Each L' also independently can be an aryl group, for example phenyl, or a heteroaryl group (e.g., pyridine). In embodiments, one L' can be a $C_{1-4}$alkyl group, and the other L' can be an aryl group. In other embodiments, each L' is phenyl. In other embodiments, each L' can either be an aryl or a heteroaryl group. For example, the phosphine can be triphenyl phosphine, trimethyl phosphine, or diphenyl-2-pyridylphosphine. In one aspect the phosphine is triphenyl phosphine. In another aspect, the phosphine is trimethyl phosphine. In another aspect, the phosphine is diphenyl-2-pyridylphosphine.

The phosphine can be present in any suitable amount to effect the dehydration reaction. For example, the phosphine can be present in a range of about 1 equivalent to about 2 equivalents, e.g., about 1.1 equivalents, or about 1.2 equivalents, or about 1.3 equivalents, or about 1.4 equivalents, or about 1.5 equivalents, or about 1.6 equivalents, or about 1.7 equivalents, or about 1.8 equivalents, or about 1.9 equivalents. In one aspect, the phosphine is present in a range of about 1.0 equivalents to about 1.5 equivalents (e.g., about 1.2 equivalents to about 1.4 equivalents). In another aspect, the phosphine is present in a range of about 1.5 equivalents to 2.0 equivalents (e.g., about 1.6 equivalent to about 1.8 equivalents).

The oxidant can be any agent capable of serving as a repository for two hydrogen atoms. Examples of the oxidant can include a benzoquinone (e.g., 2,3-dichloro-5,6-dicyanobenzoquinone ("DDQ")), azodicarboxylates, aryl and/or heteroaryl disulfides, aryl and heteroaryl hypochlorothioites, and combinations thereof. In one aspect the oxidant is DDQ. In another aspect, the oxidant is an azodicarboxylate (e.g., diethyl azodicarboxylate ("DEAD"), diisopropyl azodicarboxylate ("DIAD"), di-(4-chlorobenzyl)azodicarboxylate). In another aspect, the oxidant is an aryl or heteroaryl hypochlorothioite. In another aspect, the oxidant is an aryl or heteroaryl disulfide. For example, the oxidant can be benzothiazyl disulfide.

The oxidant can be present in any suitable amount to effect the dehydration reaction. For example, the oxidant can be present in a range of about 1 equivalent to about 2 equivalents, e.g., about 1.1 equivalents, or about 1.2 equivalents, or about 1.3 equivalents, or about 1.4 equivalents, or about 1.5 equivalents, or about 1.6 equivalents, or about 1.7 equivalents, or about 1.8 equivalents, or about 1.9 equivalents. In one aspect, the oxidant is present in a range of about 1.0 equivalents to about 1.5 equivalents (e.g., about 1.2 equivalents to about 1.4 equivalents). In another aspect, the oxidant is present in a range of about 1.5 equivalents to 2.0 equivalents (e.g., about 1.6 equivalent to about 1.8 equivalents) In another aspect, the oxidant is present in a range of about 1.4 to about 1.7 equivalents.

The dehydrating can further include an azide. The azide can be present in any suitable amount to effect the dehydration reaction. For example, the azide can be present in a range of about 1 equivalent to about 2 equivalents, e.g., about 1.4 to about 1.7 equivalents. In one aspect, the azide is trimethylsilyl azide ("TMS azide"). In one aspect, the dehydration reaction includes an azide. In another aspect, the dehydration reaction does not include an azide.

The solvent can be any suitable solvent, and can be selected to provide good conversion and optical purity in the dehydration reaction. For example, the solvent can be a chlorinated solvent, an ether solvent (e.g., tetrahydrofuran, diethyl ether), and/or acetonitrile.

The dehydration reaction can occur at a temperature less than 40° C., for example. For example, the dehydration reaction can occur at a temperature in a range of 15° C. to 35° C., or 20° C. to 30° C., e.g., 25° C. In another aspect, the dehydration reaction can occur at a temperature in a range of 30° C. to 70° C. For example, the dehydration reaction can occur at a temperature in a range of about 40° C. to about 60° C. In one aspect, the temperature is about 50° C.

Upon completion of the reaction, the reaction can be subjected to reaction workup and purified by, e.g., flash chromatography or medium pressure liquid chromatography, to result in Compound A.

In view of the teachings herein, the dehydration reaction of HYDZ using Mitsunobu conditions can result in excellent conversion (e.g., greater than 99%) and selectivity of the desired Compound A over the benzothiazole-2-thiol ("BtSH") adduct (e.g., about 94:6, or about 95:5, or about 96:4).

In view of the teachings herein, the dehydration reaction of HYDZ using a Mitsunobu conditions to form Compound A can occur with good yield. For example, the yield of Compound A can be at least about 40%, or at least about 50%, or at least about 60%, or at least about 70%, or at least about 80%, at least about 85%, at least about 90%, at least about 95%, or at least about 99%. Further, the purity of Compound A can be at least about 97%, at least about 99%, or about 100%. Using Mitsunobu conditions to dehydrate HYDZ to form Compound A can occur with high optical purity (e.g., greater than 95%, or greater than 97%, greater than 99%, or greater than 99.5%, or greater than 99.6%, or greater than 99.9% ee).

Compound A that results from dehydration of HYDZ using the Mitsunobu conditions can be converted to a salt. For example Compound A can be converted to a hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, or maleic acid, or combinations thereof. In one aspect, Compound A that results from dehydration of HYDZ using the Mitsunobu conditions can be converted to its HCl salt by contacting it with a solution of concentrated HCl at elevated temperature, seeded with Compound A-HCl, and crystallized The Mitsunobu dehydration of HYDZ to form Compound A is further described in the Examples section.

Route 4: Acetic Acid-Mediated Dehydration

HYDZ can be dehydrated to Compound A by contacting it with acetic acid at an elevated temperature, e.g., at least 100° C., or at least 110° C., or at least 120° C., or at least 130° C., or higher. For example, HYDZ can be dehydrated to Compound A by contacting it with acetic acid for three days at 110° C. or higher, e.g., 120° C. The dehydration reaction results in racemic material. Other acids, such as trifluoroacetic acid, acetic acid, methansulfonic acid, polyphosphoric acid, and toluenesulfonic acid, can be used for the dehydration reaction. However, these acids did not result in as good of a conversion of HYDZ to Compound A as acetic acid, in experiments. Contacting HYDZ with acetic acid produced two impurities, in experiments. The optical purity of Compound A as a result of acetic acid-mediated dehydration can be about 80% ee, which is about a 15% decrease in optical purity from the starting material. The decrease in optical purity likely results from the harsh and acidic cyclization conditions.

Formation of Compound A Monohydrate

The monohydrate form of Compound A is advantageously stable and robust in range of about 15% to about 95% relative humidity, and up to about 50° C. Further, the formation of the monohydrate form of Compound A can provide control of the particle size.

As described above, the monohydrate form of Compound A can be formed directly from the end-stage reaction solution of the dehydration of HYDZ to Compound A.

The monohydrate form of Compound A also can be formed from the HCl salt of Compound A. In this embodiment, the HCl salt of Compound A can be broken down and crystallized to form the monohydrate form of Compound A.

The HCl salt of Compound A can be broken down and crystallized in a solvent that includes alcohol and water. The alcohol can be, e.g., methanol, ethanol, and isopropanol. In one aspect the alcohol can include isopropanol. In another aspect, the alcohol can include ethanol. In another aspect, the alcohol can include methanol. The ratio of alcohol to water can be in a range of about 1:10 or about 10:10, for example, including about 1:1, or about 1:2, or about 1:3, or about 1:4, or about 1:5, or about 1:6, or about 1:9, or about 1:8, or about 1:9, or about 1:10, or about 10:1, or about 9:1, or about 8:1, or about 7:1, or about 6:1, or about 5:1, or about 4:1, or about 3:1, or about 2:1. For example, the ratio of alcohol to water can be about 1:3, or about 1:4, or about 1:5, or about 1:6, or about 2:1.

For example, the breakdown of the HCl salt can occur by dissolving the HCl salt in an alcohol/water solution (e.g., 2:1 isopropanol/water), adding a sodium bicarbonate solution to the HCl salt solution at a temperature less than 30° C., then increasing the temperature to about 60° C. and filtering the reaction solution. In another aspect, the breakdown of the salt can occur at a temperature in a range of about 50° C.

Crystallization to form the monohydrate of Compound A can proceed by dissolving Compound A in water, increasing the temperature of the solution to about 60° C., and introducing a seed crystal of Compound A by combining it with an alcohol/water solution (e.g., 20:80 isopropanol/water, or 20% IPA/water, or 30% ethanol/water). The resulting solution, which is optionally rinsed with the alcohol/water solution, can be aged at 55-60° C. for at least about 15 minutes, and then cooled (e.g., to about 20° C.). The monohydrate form of Compound A can be isolate by filtration and washed.

The crystallization procedure can provide crystals of the monohydrate form of Compound A in good yield (e.g., at least about 95%, at least about 97%, at least about 99% yield), and excellent purity (e.g., at least about 99%, at least about 99.5%, at least about 99.7%, or at least about 99.9%). Further the monohydrate crystals can exhibit excellent optical purity (e.g., at least about 99.5%, at least about 99.7%, or about 100%).

Conversion of the HCl salt of Compound A to the monohydrate form is further described in the Examples section.

Preparation of PYRH

As described above, 3-fluoro-2-hydrazinyl-5-(1-methyl-1H-pyrazol-4-yl)pyridine ("PYRH") is one of the three starting materials used to prepare Compound A. Another aspect of the disclosure provides a method for preparing PYRH by:
(i) admixing

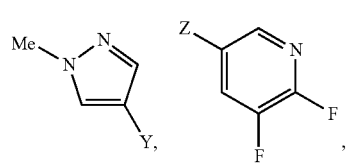

and a catalyst, under conditions sufficient to form an intermediate:

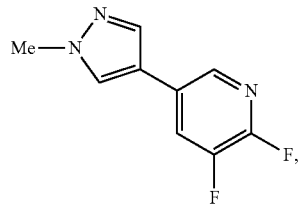 [SMILES: Cn1cc(-c2cnc(F)c(F)c2)cn1]

wherein:
(a) Y is F, Cl, Br, I, or OTf, and Z comprises boronic acid, boronic ester, magnesium, zinc, zirconium, tin, or silicon; or
(b) Y comprises boronic acid, boronic ester, magnesium, zinc, zirconium, tin, or silicon, and Z is F, Cl, Br, I, or OTf; and
(ii) admixing

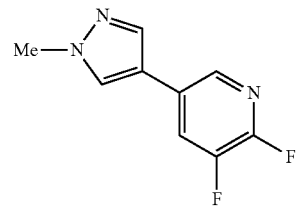 [SMILES: Cn1cc(-c2cnc(F)c(F)c2)cn1]

and H$_2$NNH$_2$, under conditions sufficient to form PYRH:

(PYRH)

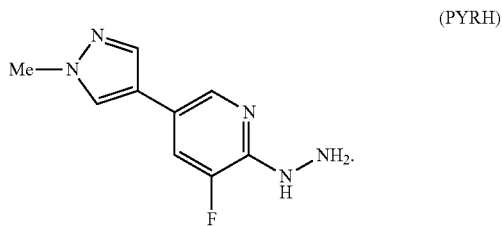 [SMILES: Cn1cc(-c2cnc(NN)c(F)c2)cn1]

More specifically, PYRH can be prepared in two steps: (1) a metal-catalyzed cross-coupling reaction of a 1-methyl-1H-pyrazolyl compound and a 2,3-difluoropyridine compound to form a 2,3-difluoro-5-(1-methyl-1H-pyrazol-4-yl) pyridine intermediate, and
(2) reaction of the intermediate with hydrazine to form PYRH:

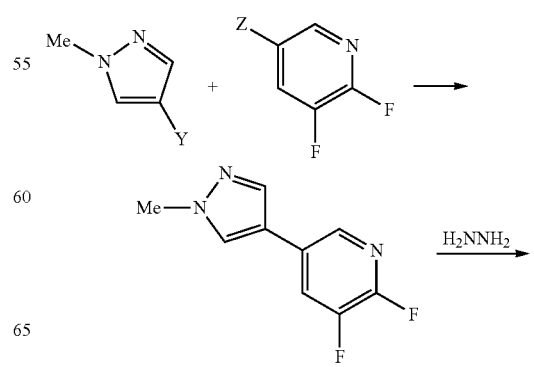

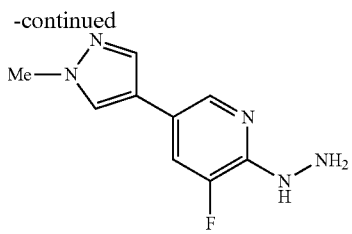

PYRH

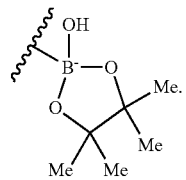 [SMILES: *[B-]1(O)OC(C)(C)C(C)(C)O1]

In one aspect the boronate, wherein:

(a) Y is F, Cl, Br, I, or OTf, and Z comprises boronic acid, boronic ester, magnesium, zinc, zirconium, tin, or silicon; or (b) Y comprises boronic acid, boronic ester, magnesium, zinc, zirconium, tin, or silicon, and Z is F, Cl, Br, I, or OTf.

The preparation of PYRH disclosed herein results in a crystalline product that is stable when stored at room temperature and protected from light and air. Although samples that are exposed to air for over a month develop some degree of coloration, they show no change in purity or weight % by HPLC.

Step 1: Preparation of the Intermediate

The first step in the preparation of PYRH is a metal-catalyzed cross-coupling reaction of a 1-methyl-1H-pyrazolyl compound and a 2,3-difluoropyridine compound to form the intermediate, 2,3-difluoro-5-(1-methyl-1H-pyrazol-4-yl)pyridine. In particular, the first step is the cross-coupling of an organometallic compound with a halide or a triflate. Such cross-coupling of organometallic compounds and halides or triflates are well known in the art (see, e.g., U.S. Pat. No. 6,686,428, Clayden, Organic Chemistry pp. 1324-1332, Oxford University Press (2010)).

In one class of embodiments, the 1-methyl-1H-pyrazolyl compound is the halide or triflate, and the 2,3-difluoropyridine compound is the organometallic compound. In these embodiments, Y is F, Cl, Br, I, or OTf, and Z comprises boron (e.g., boronic acid, boronic ester, or boronate), magnesium, zinc, zirconium, tin, or silicon.

In another class of embodiments, the 1-methyl-1H-pyrazolyl compound is the organometallic compound, and the 2,3-difluoropyridine compound is halide or triflate. In these embodiments, Y comprises boron (e.g., boronic acid, boronic ester, or boronate), magnesium, zinc, zirconium, tin, or silicon, and Z is F, Cl, Br, I, or OTf.

The organometallic compound can comprise boron, and can be a boronic acid or boronic ester, or a boronate. When the organometallic compound is a boronic acid, a boronic ester, or boronate, the reaction is a Suzuki-type cross-coupling reaction.

In one aspect boronic acid can be used as an organometallic compound. In another aspect, boronic ester can be used as an organometallic compound. Examples of boronic esters include pinacolborane and catecholborane. In still other aspects, boronates can be used, for example 9-borabicyclo[3.3.1]nonane ("9-BBN"), an N-methyliminodiacetic acid boronate ("MIDA boronate") and 2-hydroxy-4,4,5,5-tetramethyl-2-(1-methyl-1H-pyrazol-4-yl)-1,3,2-dioxaborolan-2-uide:

is used and can be prepared according to the process reported in Stewart et al., Org. Process Res. Dev. 14:849-858 (2010). Boronic acids, boronic esters, and boronates are described in Leenox et al. Chem Soc. Rev. 43:412 (2014).

The organometallic compound can include magnesium. When the organometallic compound includes magnesium, the reaction is a Kumada-type cross coupling reaction.

The organometallic compound can include zinc. When the organometallic compound includes zinc, the reaction is a Negishi-type cross coupling reaction.

The organometallic compound can include tin. When the organometallic compound includes tin, the reaction is a Stille-type cross coupling reaction.

The organometallic compound can include silicon. When the organometallic compound includes silicon, the reaction is a Hiyama-type reaction.

Suzuki, Kumada, Nehishi, Stille, and Hiyama cross-coupling reactions are well known in the art. See, e.g., Nicolaou et al., Palladium Catalyzed Transformations in Organic Synthesis" Angewandte Chemie International Edition, 44(29):4442-4489 (2005).

The cross-coupling reactions described herein can achieve good stereospecificity and yield in the presence of a transition metal catalyst. Transition metal catalysts useful for the cross-coupling reactions disclosed herein include palladium (0), palladium (II), nickel, copper, and iron. For example, in one aspect palladium (0) and palladium (II) catalysts can be used. Suitable catalysts can include $Pd_2(dba)_3$, $Pd(PPh_3)$, a PEPPSI-SIPr, or a palladacycle selected from the group consisting of a DavePhos, a XPhos, a SPhos, a JohnPhos, a RuPhos, a BrettPhos, a JackiePhos, a CPhos, and combinations thereof.

Specific examples of suitable catalysts include: 2-Dicyclohexylphosphino-2'-(N,N-dimethylamino)biphenyl ("DavePhos"), 2-Dicyclohexylphosphino-2',4',6'-triisopropylbiphenyl ("XPhos"), 2-Dicyclohexylphosphino-2',6'-dimethoxybiphenyl ("SPhos"), 2-Di-tert-butylphosphino-2',4',6'-triisopropylbiphenyl ("tBuXPhos"), (2-Biphenyl)dicyclohexylphosphine ("CyJohnPhos"), (2-Biphenyl)di-tert-butylphosphine ("JohnPhos"), Sodium 2'-dicyclohexylphosphino-2,6 dimethoxy-1,1'-biphenyl-3-sulfonate hydrate ("SPhos") [water soluble], 2-Di-tert-butylphosphino-3,4,5,6-tetramethyl-2',4',6'-triisopropyl-1,1'-biphenyl ("Tetramethyl tBuXPhos"), 2-Dicyclohexylphosphino-2',6'-diisopropoxybiphenyl ("RuPhos"), 2'-(Diphenylphosphino)-N,N-dimethyl-(1,1'-biphenyl)-2-amine, 2-iphenylphosphino-2'-(N,N-dimethylamino)

biphenyl ("PhDave-Phos"), 2'-(Di-tert-butylphosphino)-N,N-dimethylbiphenyl-2-amine ("t-BuDavePhos"), 2-Dicyclohexylphosphino-2'-methylbiphenyl, 2-Methyl-2'-dicyclohexylphosphinobiphenyl ("MePhos"), 2-Di-tert-butylphosphino-2'-methylbiphenyl("tBuMePhos"), (2-Biphenyl)di-tert-butylphosphine gold(I) chloride ("JohnPhos"), 2-Dicyclohexylphosphino-2',4',6'-triisopropylbiphenyl gold(I) chloride ("XPhos AuCl"), 2-Dicyclohexylphosphino-2',4',6'-triisopropylbiphenyl gold(I) bis(trifluoromethanesulfonyl)imide ("XPhos AuNTf2"), 2-(Dicyclohexylphosphino) 3,6-dimethoxy-2',4',6'-triisopropyl-1,1'-biphenyl ("BrettPhos"), Chloro(2-dicyclohexylphosphino-2',4',6'-triisopropyl-1,1'-biphenyl)[2-(2-aminoethyl)phenyl)]palladium(II) ("XPhos Palladacycle"), Chloro(2-dicyclohexylphosphino-2',6'-dimethoxy-1,1'-biphenyl)[2-(2-aminoethylphenyl)]palladium(II)-methyl-t-butyl ether adduct ("SPhos Palladacycle"), t-BuXPhos palladium(II) phenethylamine chloride ("tBuXPhos Pd G1"), 2-{Bis[3,5-bis(trifluoromethyl)phenyl]phosphino}-3,6-dimethoxy-2',4',6'-triisopropyl-1,1'-biphenyl ("JackiePhos"), 2-(Di-tert-butylphosphino)-2',4',6'-triisopropyl-3,6-dimethoxy-1,1'-biphenyl ("tBuBrettPhos"), Dicyclohexyl(2',4',6'-trimethoxy[1,1'-biphenyl]-2-yl)-phosphine ("BrettPhos Pd G1 Methyl-t-Butyl Ether Adduct"), Chloro(2-dicyclohexylphosphino-2',4',6'-triisopropyl-1,1'-biphenyl)[2-(2'-amino-1,1'-biphenyl)]palladium(II) ("Xphos Pd G2"), Chloro(2-dicyclohexylphosphino-2',6'-dimethoxy-1,1'-biphenyl)[2-(2'-amino-1,1'-biphenyl)]palladium(II) ("SPhos Pd G2"), Chloro(2-dicyclohexylphosphino-2',6'-diisopropoxy-1,1'-biphenyl)[2-(2'-amino-1,1'-biphenyl)]palladium(II) ("RuPhos Pd G2"), Chloro[(2-dicyclohexylphosphino-2',6'-bis(N,N-dimethylamino)-1,1'-biphenyl)-2-(2'-amino-1,1'-biphenyl)]palladium(II) ("CPhos-Pd-G2"), [(2-Dicyclohexylphosphino-2',6'-bis(N,N-dimethylamino)-1,1'-biphenyl)-2-(2'-amino-1,1'-biphenyl)] palladium(II) methanesulfonate ("CPhos-Pd-G3"), [(2-Di-tert-butylphosphino-2',4',6'-triisopropyl-1,1'-biphenyl)-2-(2'-amino-1,1'-biphenyl)] palladium(II)methanesulfonate ("tBuXPhos-Pd-G3"), (2-Dicyclohexylphosphino-2',6'-diisopropoxy-1,1'-biphenyl)[2-(2'-amino-1,1'-biphenyl)]palladium(II) methanesulfonate ("RuPhos-Pd-G3"), (2-Dicyclohexylphosphino-2',4',6'-triisopropyl-1,1'-biphenyl)[2-(2'-amino-1,1'-biphenyl)]palladium(II) methanesulfonate ("XPhos-Pd-G3"), [(2-Di-cyclohexylphosphino-3,6-dimethoxy-2',4',6'-triisopropyl-1,1'-biphenyl)-2-(2'-amino-1,1'-biphenyl)] palladium(II) methanesulfonate ("BrettPhos-Pd-G3"), [(2-{Bis[3,5-bis(trifluoromethyl)phenyl]phosphine-3,6-dimethoxy-2',4',6'-triisopropyl-1,1'-biphenyl)-2-(2'-amino-1,1'-biphenyl)]palladium(II) Methanesulfonate ("JackiePhos-Pd-G3"), and combinations thereof.

PEPPSI-SIPr and the like also are suitable catalysts.

In particular the catalyst can be $Pd_2(dba)_3$, an Xphos-palladacycle, $Pd(PPh_3)_4$, and combinations thereof, for example. In one aspect the catalyst comprises Xphos-palladacycle. In another aspect, the catalyst is $Pd(PPH_3)_4$.

The cross-coupling reaction can proceed in the absence of a base. The cross-coupling reaction can include a suitable base (e.g., $K_3PO_4$, CsF, and/or $Cs_2CO_3$). In one aspect, the cross-coupling reaction includes $Cs_2CO_3$. In another aspect, the cross-coupling reaction includes is $K_3PO_4$. The base can be present in an amount that results in good conversion (e.g., 1.5 equivalents).

When the organometallic compound is a boronic acid or ester, the solvent can be an anhydrous aprotic solvent. Examples of suitable solvents include dioxane, toluene, tetrahydrofuran ("THF"), 2-MeTHF, and combinations thereof. The solvent, 2-MeTHF, can produce the intermediate in high yield. Although 1-butanol/water is a common solvent for the metal-catalyzed cross-coupling reactions, it is not optimal for the formation of the intermediate described herein. In one example, 1-butanol/water caused C—F reduction of the product, likely because butanol serves as a hydride source, and cross-coupling of a second pyrazole at the 2-position of the pyridine ring, indicating that oxidative insertion can occur at the C—F bond.

When the organometallic compound includes a boronic acid or a boronic ester, a phase transfer catalyst ("PTC") can be included in the reaction mixture. For example, the phase transfer catalyst can be selected from quaternary salts (e.g., chlorides, bromides, hydrogen sulfates, iodides, ammonium salts, and phosphonium salts) and crown ethers. In one aspect the phase transfer catalysts can be a quaternary ammonium or phosphonium salt. In another aspect, the phase transfer catalyst can be a crown ether.

Suitable quaternary ammonium salts include Tetramethylammonium bromide, Tetramethylammonium chloride, Tetramethylammonium hexafluorophosphate, Tetramethylammonium hydroxide pentahydrate, Tetramethylammonium hydroxide, Tetramethylammonium hydroxide, Tetramethylammonium iodide, Tetramethylammonium nitrate, Tetramethylammonium perchlorate, Tetramethylammonium tetrafluoroborate, Triethylmethylammonium chloride, Tetraethylammonium bromide, Tetraethylammonium chloride monohydrate, Tetraethylammonium hydroxide, Tetraethylammonium hydroxide, Tetraethylammonium hydroxide, Tetraethylammonium iodide, Tetraethylammonium nitrate, Tetraethylammonium perchlorate, Tetraethylammonium tetrafluoroborate, Tetraethylammonium p-toluenesulfonate, (1-Hexyl)trimethylammonium bromide, Phenyltrimethylammonium bromide, Phenyltrimethylammonium chloride, Phenyltrimethylammonium iodide, Phenyltrimethylammonium methosulfate, Benzyltrimethylammonium bromide, Benzyltrimethylammonium chloride, Benzyltrimethylammonium hexafluorophosphate, Benzyltrimethylammonium hydroxide, Benzyltrimethylammonium iodide, (1-Butyl)triethylammonium bromide, (1-Octyl)trimethylammonium bromide, Tetra-n-propylammonium bromide, Tetra-n-propylammonium chloride, Tetra-n-propylammonium hydrogen sulfate, Tetra-n-propylammonium hydroxide, Tetra-n-propylammonium iodide, Phenyltriethylammonium iodide, Methyltri-n-butylammonium bromide, Methyltri-n-butylammonium chloride, (1-Decyl)trimethylammonium bromide, Benzyltriethylammonium bromide, Benzyltriethylammonium chloride, Benzyltriethylammonium hydroxide, Benzyltriethylammonium tetrafluoroborate, (1-Dodecyl)trimethylammonium chloride, (1-Dodecyl) trimethylammonium bromide, Benzyltri-n-propylammonium chloride, Tetra-n-butylammonium acetate, Tetra-n-butylammonium acetate, Tetra-n-butylammonium bromide, Tetra-n-butylammonium chloride, Tetra-n-butylammonium chloride, Tetra-n-butylammonium hexafluoro-phosphate, Tetra-n-butylammonium hydrogen sulfate, Tetra-n-butylammonium hydroxide, Tetra-n-butylammonium hydroxide, Tetra-n-butylammonium hydroxide, Tetra-n-butylammonium hydroxide, Tetra-n-butylammonium iodide, Tetra-n-butylammonium nitrate, Tetra-n-butylammonium perchlorate, Tetra-n-butylammonium perchlorate, Tetra-n-butylammonium phosphate, Tetra-n-butylammonium sulfate, Tetra-n-butylammoniumtrifluoromethane-sulfate, (1-Tetradecyl) trimethylammonium bromide, (1-Tetradecyl) trimethylammonium chloride, (1-Hexadecyl) trimethylammonium bromide, Ethyl(1-hexadecyl) dimethylammonium, Tetra-n-pentylammonium iodide, Benzyltri-n-butylammonium bromide, Benzyltri-n-butylammonium chloride, Benzyltri-n-butylammonium iodide, (1-Hexadecyl)pyridinium bromide monohydrate, (1-Hexadecyl)pyridinium chloride monohydrate, Di-n-decyldimethylammonium bromide, Tetra-n-hexylammonium bromide, Tetra-n-hexylammonium hydrogen sulfate, Tetra-n-hexylammonium iodide, Tetra-n-hexylammonium perchlorate, Di-n-dodecyldimethylammonium bromide, Tetra-n-heptylammonium bromide, Tetra-n-heptylammonium iodide, Tetra-n-octylammonium bromide, Dimethyldistearylammonium chloride, Tetra-n-dodecylammonium iodide, Tetraoctadecylammonium bromide.

In one aspect tetrabutylammonium bromide ("TBAB") can be used. In another aspect, tetra-n-butylammonium phosphate can be used. In still another aspect, di-n-decyldimethylammonium bromide can be used.

Suitable phosphonium salts include, but are not limited to, bis(triphenylphosphoranilydene)-ammonium chloride, (1-Hexadecyl)tri-n-butylphosphonium bromide, tetra-n-butylphosphonium bromide, tetraphenylphosphonium bromide, tetraphenylphosphonium chloride, tetraphenylphosphonium hexafluoro-antimonate, tetraphenylphosphonium iodide, tetraphenylphosphonium tetrafluoroborate, (triphenylmethyl)triphenylphosphonium chloride.

Adding a catalytic amount of a PTC to the reaction mixture can consistently increase the reaction yield and can consistently consume the starting material. For example, 5 mol % of TBAB can be added to the reaction. Without being bound by any particular theory, the PTC increases the solubility of phosphate in 2-MeTHF, and thus, increases the concentration of active boronate, which accelerates transmetallation to palladium. The bromide counterion to TBAB also could be playing a role in the improved reaction conditions. In one example, when a PTC is not added to the reaction mixture, the product yield was less than 50%.

When the organometallic compound is a boronate, the solvent can include water and a alcohol. Examples of suitable alcohols include 1-butanol, 2-butanol, and the like. In one aspect the alcohol is 1-butanol. In another one aspect, the alcohol is 2-butanol.

The temperature can be below the reflux temperature of the reaction mixture. For example, the temperature can be in a range of about 60° C. to 80° C., or 65° C. to 75° C. (e.g., 70° C.). In one example, when the temperature was increased above 70° C. or 80° C., the amount of catalyst that precipitated from the reaction increased, lowering its lifetime. The compounds in the reaction solution can be stable at 80° C. for up to about 24 hours. Extended heating, however, can reduce the amount of halide or triflate starting material through the headspace due to the boiling point of this reagent.

In one type of embodiment, the intermediate can be formed by admixing 5-chloro-2,3-difluoropyridine (e.g., about 1 equivalent) with

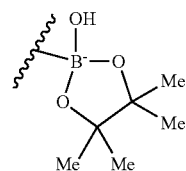 [SMILES: *[B-]1(O)OC(C)(C)C(C)(C)O1]

(e.g., about 0.9 equivalents) in an alcohol/water slurry (e.g., 2-BuOH/water) at, e.g., 20° C. The resulting boronate slurry can be slowly added to a solution containing a palladium catalyst (e.g., about 0.004 equivalents of an Xphos-palladacycle) and an alcohol (e.g., 2-BuOH) over 1 hour at, e.g., 80° C. The slow addition of the boronate prevents an exotherm. The reaction can be allowed to proceed until about 95% conversion. In one example, attempts to obtain a conversion over 98% resulted in increased impurity. Upon completion of the reaction, the reaction mixture can be rinsed with an alcohol (e.g., 2-butanol).

Reaction workup can occur by any suitable means (e.g., extraction). When the workup is extractive, it can occur in a toluene/2-butanol solution at a temperature above 40° C., for example, 50° C., 60° C., or 70° C. In one example, an extractive workup at a temperature below 40° C. resulted in precipitation and loss of the product. In one aspect, the workup can include adding $NaHSO_3$ solution to the reaction mixture. In another aspect, the workup can include using thioglycolyic acid. In another aspect, Celite can be used after treatment with $NaHSO_3$ to decrease the palladium content.

Following workup, the desired intermediate can be isolated by crystallization. The workup solvent can be swapped with 2-butanol, and heptane can be added to the slurry at a temperature in a range of 20° C. to 50° C., for example. The temperature of the resulting slurry can be increased (e.g., in a range of 90° C. to 100° C.), and the slurry can be aged (e.g., for at least 15 minutes). After aging is complete, the slurry can be cooled (e.g., to 20° C.) over a period of time (e.g., greater than 3 hours), and the resulting crystals can be isolated and washed.

In view of the teachings herein, the cross-coupling reaction can provide the desired intermediate in good yield (e.g., greater than 95% crude, greater than 87% isolated). For example, the cross-coupling of the intermediate can result in a yield of at least about 95%, at least about 97%, or at least about 99%. The cross-coupling reaction can also result in excellent purity (e.g., at least about 97%, at least about 98%, at least about 99%).

Preparation of the intermediate in the synthesis of PYRH is further described in the Examples section.

Step 2: Preparation of PYRH

The second step in the preparation of PYRH is a nucleophilic aromatic substitution reaction between the intermediate and hydrazine.

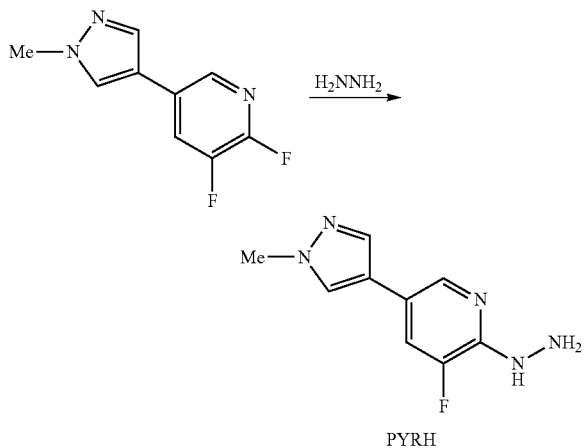

In this reaction, at least about 1 equivalent, or at least about 2 equivalents, or at least about 3 equivalents, or at least about 4 equivalents, or at least about 5 equivalents, or at least about 6 equivalents, or at least about 7 equivalents, or higher of hydrazine can be used. In one class of embodiments, at least about 3 equivalents, or at least about 4 equivalents, or at least about 5 equivalents, or at least about 6 equivalents of hydrazine are used.

Hydrazine serves as both a reactant and as a base for the evolved HF. Therefore, at least two equivalents of the hydrazine can be used. Addition of excess hydrazine to the reaction mixture leads to acceleration of the reaction rate. In one example, when 6 equivalents of hydrazine was used instead of 3 equivalents, the reaction time decreased from 6 hours to 3 hours, with no changes in the purity profile of the product.

The temperature of the nucleophilic aromatic substitution reaction can be above 70° C. (e.g., at least 70° C., at least 80° C., at least 90° C., at least 100° C., at least 110° C.). A lower temperature can increase the reaction time. In one example, decreasing the reaction temperature from 100° C. to 80° C. resulted in an increase in reaction time from 4 to 10 hours. The intermediate has poor solubility in water, which can lead to long reaction times at lower temperatures. In one example, no reaction occurred at room temperature.

Any suitable solvent can be used for the nucleophilic aromatic substitution reaction. The solvent can include, e.g., water, alcohol, and combinations thereof. The alcohol solvent can include methanol, ethanol, propanol, isopropanol, n-butanol, 2-butanol, and combinations thereof. In one aspect the solvents are selected from methanol, water, and a combination thereof. Performing the reaction in water is practical and safe.

Upon completion of the reaction, the desired PYRH can crystallize directly from the reaction mixture. The resulting PYRH product is stable when stored at room temperature and protected from light and air.

The method for preparing PYRH disclosed herein can provide PYRH in good yield (e.g., at least about 90%, at least about 95%, at least about 97% yield, at least about 99%), and excellent purity (e.g., at least about 97%, at least about 99%, at least about 99.5%, or at about 100%).

Preparation of PYRH is further described in the Examples section. Alternative methods for synthesizing PYRH are known in the art (see, e.g., PCT Publication WO 2013/38362 at page 78-79, which is incorporated herein by reference in its entirety).

Preparation of NAPH

Another aspect of the disclosure provides methods for preparing 3-(2-methoxyethoxy)-1,6-naphthyridin-5(6H)-one ("NAPH"). As described above, NAPH is one of the three starting materials used to prepare Compound A.

Method 1

Provided herein is a method of making NAPH prepared from methylnicotinate (commercially available from e.g., SigmaAldrich), 1,3,5-triazine, and methoxyethanol in two steps. First, the methylnicotinate is condensed with 1,3,5-triazine in the presence of a base to give an intermediate naphthyridinone.

Step 1

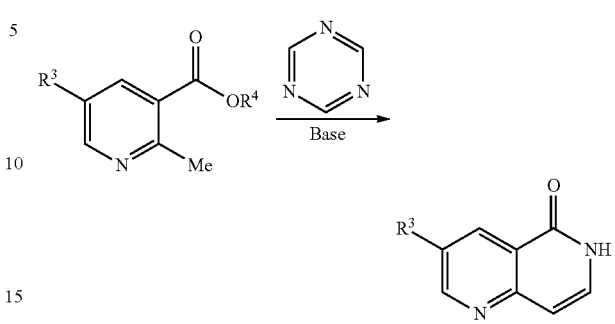

wherein $R^3$ is Cl, Br, or I and $R^4$ is alkyl, including but not limited to, Me, Et, n-Pr, or n-Bu.

The solvent of the condensation reaction can be any suitable solvent. For example, the solvent can include any polar aprotic solvent, including but not limited to one or more of dimethyl sulfoxide and dimethylacetamide.

The base can be any suitable strong base. For example, the base can be selected from $Cs_2CO_3$, KOtBu, $K_3PO_4$, $K_2CO_3$, and combinations thereof. The reaction of the base with the methylnicotinate and triazine is exothermic. The method of addition can be used to control the exotherm. For example, a gradual or portioned (e.g. drop-wise) addition of a solution of both starting materials into a slurry of the base can suppress the exotherm.

The condensation reaction can occur at any suitable temperature. For example, the reaction can occur at a temperature in a range of about 15° C. to 100° C., 20° C. to 95° C., 30° C. to 90° C., 40° C. to 85° C., or 50° C. to 80° C.

The condensation reaction produces a naphthyridinone, an advantageously stable compound, that can be isolated as a beige solid. In view of the teachings herein, the synthesis of the naphthyridinone can be high yielding (e.g. 80-95% isolated) with good purity (e.g., greater than 90 wt. %).

Second, after the intermediate naphthyridinone is formed, it is subsequently treated with a salt of 2-methoxyethanol in the presence of a catalyst to give NAPH.

Step 2

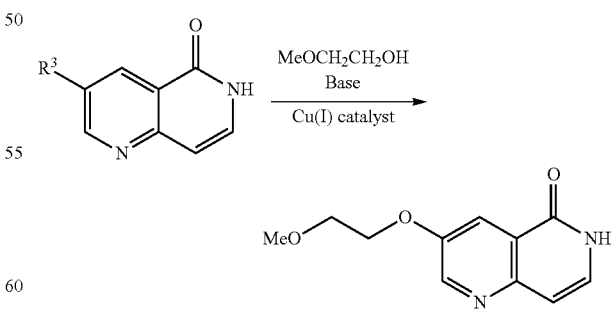

The solvent of the etherification reaction can be any suitable solvent. For example, the solvent will be an ether solvent having a boiling point above about 85° C. For example, the solvent can be selected from the group consisting of 2-methoxyethanol, diglyme, dioxane, and combinations thereof. In one aspect, the solvent can be neat 2-methoxyethanol. In another aspect, the solvent can be dioxane.

The base can be any suitable base. For example, the base can be selected from KH, NaH, LiH, KOtBu, NaOtBu, LiOtBu, BuLi, HexLi, Cs$_2$CO$_3$, lithium bis(trimethylsilyl) amide ("LiHMDS"), sodium bis(trimethylsilyl)amide ("NaHMDS"), potassium bis(trimethylsilyl)amide ("KHMDS"), lithium diisopropylamide ("LDA"), lithium tetramethylpiperidide ("LiTMP"), LiOH, NaOH, KOH, CsOH, and combinations thereof. For example, the base can be a strong base, for example one or more of Cs$_2$CO$_3$, LiOtBu, LiHMDS, and KOtBu.

The etherification reaction can occur at any suitable temperature. For example, the reaction can occur at a temperature in a range of about 50° C. to 130° C., 80° C. to 120° C., or 95° C. to 115° C.

The copper (I) catalyst can be any suitable copper (I) catalyst. The Cu(I) catalyst can be used with or without a ligand. For example, suitable catalysts include, but are not limited to CuBr, CuBr-DMS, Cu(OAc), Cu(OTf), and CuI A catalyst free of iodine is more optimal for maintaining stereoselectivity in the subsequent alkylation step (to form NAPA). When the catalyst comprises a ligand, suitable ligands include, but are not limited to 1,10-phenanthroline and 3,4,7,8-tetramethyl-1,10-phenanthroline.

The etherification reaction produces NAPH, an advantageously stable compound, that can be isolated as a crystalline solid. The resulting NAPH can be purified by any suitable purification method, for example by crystallization, as described in further detail in the Examples section. NAPH is thermally stable up to at least 100° C., and is stable to acids and bases. The synthesis of NAPH using the foregoing Method 1 can have an isolated yield of at least about 65%, 75%, 85%, or 95%, for example. The yield may be affected by impurities that poison the Cu(I) catalyst in Step 2. The purity of NAPH can be at least about 90%, 95%, or 97%, for example. The purity of NAPH is affected by residual Cu(I) catalyst and water. The residual copper can be removed using a Cu(I) scavenger, e.g., N-(2-hydroxyethyl)ethylenediamine triacetic acid trisodium salt (HEDTA). Cu(I) scavenging can be assisted by the presence of or introduction of a source of reactive oxygen, e.g. air.

Method 2

The disclosure provides a method of making NAPH from a protected N-(3-formyl-4-amino-2-alkoxy)pyridine and 1-hydroxy-2-(2-methoxyethoxy)ethane-1-sulfonate in two steps. First, the protected N-(3-formyl-4-amino-2-alkoxy) pyridine is admixed with 1-hydroxy-2-(2-methoxyethoxy) ethane-1-sulfonate and base under conditions sufficient to form a naphthyridine of Formula (III).

Step 1

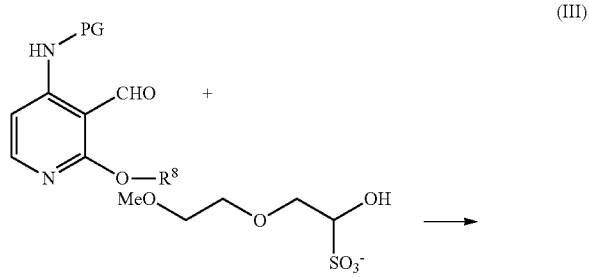

(III)

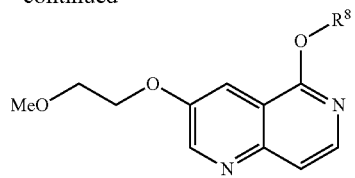

wherein R$^8$ is alkyl and PG is a protecting group.

The protecting group can be any suitable protecting group, including, but not limited to PivCl, PivBr, or Piv anhydride. R$^8$ can be any alkyl such that OR$^8$ is an ortho-directing metallation group. For example, R$^8$ can be any of C$_{1-4}$ alkyl groups.

The protected N-(3-formyl-4-amino-2-alkoxy)pyridine can be prepared by converting 2-alkoxy-pyridin-4ylamine into a protected amine followed by directed ortho-lithiation in THF or MeTHF. The directed ortho-lithiation is then quenched with, e.g., DMF or N-formylmorpholine to give the corresponding formyl substituted pyridine. The amide can then be hydrolyzed with excess base and converted to the corresponding naphthyridine ether with a methoxyethoxyl acetaldehyde bisulfite adduct.

The protected amine can be formed by admixing 2-alkoxy-pyridin-4ylamine with a protecting group selected from, for example, a compound of Formula (IV) to form an N-(2-alkoxypyridin-4-yl)pivalamide:

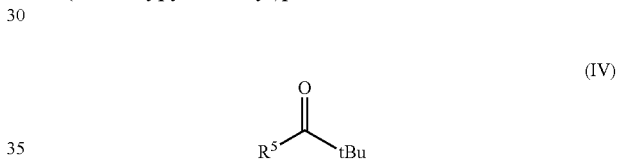

wherein R$^5$ is Cl, Br, or OC(O)alkyl and wherein alkyl is Me, Et, Pr, iPr, n-Bu, sec-Bu or t-Bu.

The protecting group can be added at any suitable temperature, for example, at a temperature in a range of about −30° C. to about 50° C., for example 0° C. The yield of the protected aminopyridine can be at least about 85%, at least about 90%, or at least about 95%, for example. The purity of the protected aminopyridine can be at least about 90%, at least about 80%, or at least about 60%, for example.

Similarly, the ortho-lithiation can be done at any suitable temperature. For example, ortho-lithiation can proceed at temperatures 25° C. or less, for example a temperature in a range of about −50° C. to about 25° C., or about −30° C. to about −10° C. The lithium reagent can be selected from n-hexyl lithium, n-butyl lithium, s-butyl lithium, lithium bis(trimethylsilyl)amide ("LiHMDS"), lithium diisopropyl amide ("LDA"), lithium tetramethylpiperidine (LiTMP), or combinations thereof, for example.

The quenching of the ortho-lithiation can proceed at any suitable temperature to provide the formyl substituted pyridine, for example, a temperature in a range of about −78° C. to 25° C., for example −10° C. The yield of the formyl substituted pyridine can be at least about 80%, at least about 85%, or at least about 90%, for example. The purity of the formyl substituted pyridine can be at least about 95%, at least about 60%, or at least about 30%, for example.

Suitable bases for hydrolyzing and thereby deprotecting the amine on the formyl substituted pyridine can be any strong base, for example, including but not limited to NaOH, KOH, K$_3$PO$_4$, LiOH, CsOH, and RbOH. Without intending to be bound by theory, it is believed that strong acids, such as HCl would be suitable for hydrolyzing and deprotecting the amine.

The admixing of the protected N-(3-formyl-4-amino-2-alkoxy)pyridine and the bisulfite adduct can occur in any suitable solvent. Suitable solvents include water-soluble solvents. Suitable solvents also include base-stable solvents. For example, methanol, ethanol, isopropanol, acetonitrile, tetrahydrofuran, dioxane, 2-methoxyethanol, t-BuOH, 2-BuOH, trifluoroethanol, water, and combinations thereof are suitable solvents.

The bisulfite adduct can be added at any suitable temperature to convert formyl substituted pyridine to the corresponding naphthyridine ether. For example, suitable temperatures include temperatures in a range of about 40° C. to about 90° C., for example, about 40° C., about 50° C., about 60° C., about 70° C., about 80° C., or about 90° C. High conversion can be achieved through slow addition of the bisulfite adduct. The bisulfite adduct is provided in an amount in a range of about 1 equivalent to about 5 equivalents, about 1 equivalent to about 4 equivalents, about 1 equivalent to about 3 equivalents, about 1 equivalent to about 2 equivalents, or about 1.6 equivalents, for example.

Optionally, the napthyridine of Formula (III) can be formed by admixing the protected N-(3-formyl-4-amino-2-alkoxy)pyridine with 2-methoxyethoxyacetaldehyde rather than the bisulfite adduct. However, the 2-methoxyethoxyacetaldehyde is not as stable as the bisulfite adduct. When 2-methoxyethoxyacetaldehyde is used, admixing can occur in any suitable solvent. Suitable solvents include water-soluble solvents. Suitable solvents also include base-stable solvents. For example, methanol, ethanol, isopropanol, and acetonitrile are suitable solvents.

The 2-methoxyethoxyacetaldehyde can be added at any suitable temperature to convert formyl substituted pyridine to the corresponding naphthyridine ether. For example, suitable temperatures include temperatures in a range of about 40° C. to about 90° C., for example, about 40° C., about 50° C., about 60° C., about 70° C., about 80° C., or about 90° C. The 2-methoxyethoxyacetaldehyde is provided in an amount in a range of about 1 equivalent to about 5 equivalents, about 1 equivalent to about 4 equivalents, about 1 equivalent to about 3 equivalents, about 1 equivalent to about 2 equivalents, or about 1.6 equivalents, for example.

Second, after the naphthyridine of Formula (III) is formed, it is subsequently treated with a strong acid under conditions sufficient to give NAPH.

Step 2

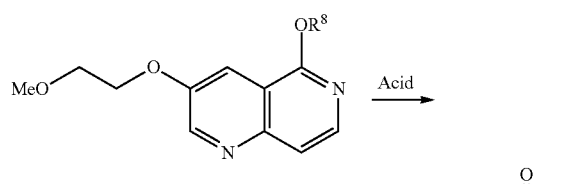
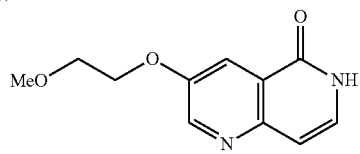

wherein $R^8$ is alkyl, e.g., any $C_{1-4}$ alkyl.

The acid can suitably be any strong acid. For example, strong acids can include inorganic acids, including but not limited to HCl, HBr, and $H_2SO_4$, and organic acids, including but not limited to, methanesulfonic acids (e.g., trifluoromethanesulfonic acid), trifluoroacetic acid, and tolylic acids. The acid can be added in any amount suitable to convert the naphthyridine of Formula (III) to NAPH. For example, the acid can be provided in an amount in a range of about 1 equivalent to about 10 equivalents, about 1 equivalent to about 8 equivalents, about 1 equivalent to about 6 equivalents, about 1 equivalent to about 4 equivalents, about 1 equivalent to about 3 equivalents, about 1 equivalent to about 2 equivalents, about 1 equivalent to about 1.5 equivalents, or about 1.2 equivalents.

The temperature of acidification can be any temperature suitable to convert the naphthyridine of Formula (III) to NAPH. For example, the temperature can be in a range of about 50° C. to about 100° C., or about 50° C. to about 80° C., or about 55° C. to about 75° C., or about 65° C.

The resulting NAPH can be purified by any suitable purification method, for example, by crystallization, as described in further detail in the Examples section. For example, the NAPH can be crystallized with a base. Suitable bases include inorganic bases, including but not limited to, NaOH, KOH, $K_2CO_3$, and $NaHCO_3$, and organic bases, including but not limited to, $Et_3N$.

In view of the teachings herein, the synthesis of NAPH by Method 2 can have an isolated yield of at least about 80%, at least about 90%, or at least about 95%, for example. The purity of NAPH can be at least about at least about 80%, at least about 30%, or at least about 10%, for example.

Method 2 can be advantageous for one or more reasons and can avoid one or more of the disadvantages of Method 1. For example, there can be one or more of the following advantages: Method 2 can produce highly pure NAPH, there can be no heavy metal contamination, the NAPH can have <0.3% organic impurities, the NAPH can be easy to dry (dry NAPH critical for downstream NAPA synthesis), the starting materials are readily available from commercial sources, there can be no highly toxic material involved in the process, and the process can be very robust and has been scaled up to greater than 80 kg per batch.

Preparation of NAPH is further described in the Examples section. Also, methods for synthesizing NAPH are known in the art (see, e.g., Fang et al., J Am Chem Soc 132(44): 15525-7 (2010); WO 2009/091375, which is incorporated herein by reference in its entirety).

Preparation of Bisulfite Adduct

Another aspect of the disclosure provides a method of making 1-hydroxy-2-(2-methoxyethoxy)ethane-1-sulfonate from 2-(2-methoxyethoxy)acetaldehyde with $HSO_3^-$, $S_2O_5^{2-}$, or a combination thereof under conditions sufficient to form the 1-hydroxy-2-(2-methoxyethoxy)ethane-1-sulfonate.

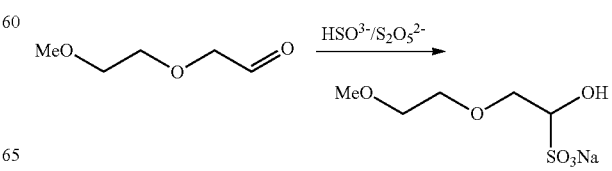

The isolated 1-hydroxy-2-(2-methoxyethoxy)ethane-1-sulfonate is advantageously stable. For example, in contrast to the 2-(2-methoxyethoxy)acetaldehyde starting material which is highly unstable, samples of the 1-hydroxy-2-(2-methoxyethoxy)ethane-1-sulfonate can be left exposed to the atmosphere for at least 2 years without decomposing. Further, the raw materials used to produce the 1-hydroxy-2-(2-methoxyethoxy)ethane-1-sulfonate are readily available and the yield is higher than for other methods of preparing 1-hydroxy-2-(2-methoxyethoxy)ethane-1-sulfonate.

The 2-(2-methoxyethoxy)acetaldehyde can be reacted with $HSO_3^-$, $S_2O_5^{2-}$, or a combination thereof. The $HSO_3^-$ and $S_2O_5^{2-}$ anion can be provided in any form, for example, having a counterion selected from $Li^+$, $K^+$, $Na^+$, $Me_4N^+$, $Et_4N^+$, $Bu_4N^+$, or combinations thereof.

The addition of the $HSO_3^-$ and/or $S_2O_5^{2-}$ to the 2-(2-methoxyethoxy)acetaldehyde can be performed at any suitable temperature. For example, the addition of $HSO_3^-$ and/or $S_2O_5^{2-}$ can be performed at a temperature in a range of about −10° C. to 50° C.

Suitable solvents for the addition of the $HSO_3^-$ and/or $S_2O_5^{2-}$ to the 2-(2-methoxyethoxy)acetaldehyde include, for example methoxyethanol, water, methanol, ethanol, and combinations thereof (e.g., methoxyethanol, water/methanol, and water/ethanol).

In view of the teachings herein, the yield of the 1-hydroxy-2-(2-methoxyethoxy)ethane-1-sulfonate production can be least about 50%, at least about 60%, at least about 70%, or at least about 80%, for example. The 1-hydroxy-2-(2-methoxyethoxy)ethane-1-sulfonate formed by this method can have a purity of at least about 40%, at least about 50%, or at least about 60% as a solution in $H_2O$, with water making up the majority of the remaining weight.

In embodiments of the disclosure, the 2-(2-methoxyethoxy)acetaldehyde can formed by oxidizing 2-(2-methoxyethoxy)-1-ethanol with an oxidizing agent.

The oxidizing agent can be selected from oxalyl chloride, pyridinium chlorochromate ("PCC"), pyridinium dichromate ("PDC"), or dimethyl sulfoxide ("DMSO") activated with a sulfur trioxide pyridine complex, for example. The oxidation can take place via a Swern oxidation, for example with oxalyl chloride, DMSO and an organic base. The Swern oxidation is well known in the art.

When the oxidation further includes a base, for example, a Swern oxidation, the base can be selected from organic bases, including but not limited to, triethylamine, N,N-diisopropylethylamine (DIPEA), N-methylmorpholine, and combinations thereof.

Suitable solvents for the oxidation include, but are not limited to, high boiling solvents (e.g., boiling point >100° C.), for example methoxyethanol.

Using the oxidation method, the yield of 2-(2-methoxyethoxy)acetaldehyde can be at least about 50%, or at least about 60%, or at least about 70%, or at least about 80%, at least about 85%, at least about 90%, at least about 95%, or at least about 99%. Further, the purity of 2-(2-methoxyethoxy)acetaldehyde can be at least about 50%, or at least about 60%, or at least about 70%, or at least about 80%, at least about 85%, at least about 90%, or at least about 95%.

In embodiments of the disclosure, the 2-(2-methoxyethoxy)acetaldehyde can be formed by: (i) admixing methoxyethanol with a compound of Formula (V):

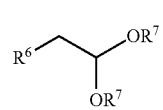

(V)

and a strong base, followed by hydrolysis to form the 2-(2-methoxyethoxy)acetaldehyde; wherein $R^6$ is selected from the group consisting of Cl, Br, I, and cyclic diol protecting groups, i for example, ethylene glycol and 1,3-propanediol, and $R^7$ is $C_{1-4}$alkyl, and each $R^7$, independently, is $CH_3$, $CH_2CH_3$, or $CH_2CH_2CH_3$.

The reaction proceeds via an $S_N2$ mechanism. This method is advantageous because it provides a higher yield than the oxidation process and does not require equipment to support cryogenic procedures, as the Swern oxidation does.

The strong base can be present in an amount in a range of about 1 equivalent to about 1.5 equivalents, or about 1.2 equivalents, for example. Any suitable strong base can be used, for example, one or more of NaH, LiH, LiOt-Bu, BuLi, hexLi, NaOt-Bu, KOt-Bu, KH and LiOH.

The admixing can occur at any suitable temperature to promote the $S_N2$ reaction. Suitable temperatures can be in a range of about 100° C. to about 120° C., or about 110° C., for example.

The hydrolysis to form the 2-(2-methoxyethoxy)acetaldehyde occurs in acidic conditions. Suitable acids include but are not limited to strong acids, including inorganic acids, including but not limited to HCl, HBr, and $H_2SO_4$, and organic acids, including but not limited to, methanesulfonic acids and tolylic acids.

Using the $S_N2$ method, the yield of 2-(2-methoxyethoxy)acetaldehyde can be at least about 40%, or at least about 50%, or at least about 60%, or at least about 70%, or at least about 80%, at least about 85%, at least about 90%, at least about 95%. Further, the purity of 2-(2-methoxyethoxy)acetaldehyde can be at least about 80%, or at least about 85%, or at least about 90%, or at least about 95%, or at least about 97%, or at least about 99%.

Preparation of the bisulfite adduct is further described in the Examples section.

EXAMPLES

The following examples are provided for illustration and are not intended to limit the scope of the invention.

Example 1

Synthesis of (R)-2-(3-(2-methoxyethoxy)-5-oxo-1,6-naphthyridin-6(5H)-yl)propanoic acid naphthalene-2-sulfonate (NAPA)

Scheme 1: Synthesis of naphthyridinone acid 2-napsylate (NAPA)

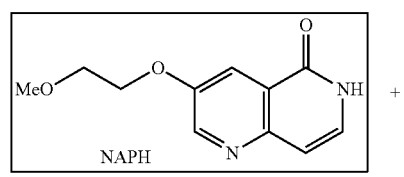

NAPH +

45

-continued

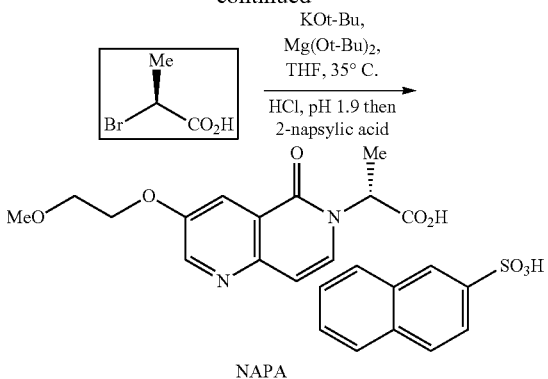

NAPA

NAPA was synthesized according to Scheme 1 by the following procedure. A jacket reactor (60 L) was charged with 3000 g (1.0 equivalent) of 3-(2-methoxyethoxy)-1,6-naphthyridin-5(6H)-one and 4646 g (2.0 equivalents) of magnesium tert-butoxide. 12 L (4.0 Vol) tetrahydrofuran was added to the reactor and an $N_2$ sweep and stirring were initiated. 2213 g (1.5 equivalents) of S-2-bromopropionic acid was added over at least 30 min, controlling the addition such that the batch temperature did not rise above 30° C. The charge port was rinsed with tetrahydrofuran (0.5 Vol) after addition. The batch was then aged for at least 5 min at 25° C. 1600 g (1.05 equivalents) of potassium tert-butoxide was added to the reactor in four portions (approximately equal) such that the batch temperature did not rise above 30° C. The charge port was again rinsed with tetrahydrofuran (1.5 L, 0.5 Vol). The batch temperature was adjusted to 35±5° C. and the batch was aged for at least 12 h.

A separate 100 L reactor was charged with 6 L of 2-Metetrahydrofuran (2-MeTHF) (2.0 Vol), 8.4 L of water (1.5 Vol) and 9.08 L (4.0 equivalents) of 6 N HCl. The mixture from the 60 L reactor was pumped into the 100 L reactor, while maintaining the batch temperature at less than 45° C.

The batch temperature was then adjusted to 20±5° C. The pH of the batch was adjusted with 6N HCl (or 2N NaOH) solution until the pH was 1.4 to 1.9. The aqueous layer was separated from the product-containing organic layer. The aqueous layer was extracted with 2-MeTHF (2 Vol), and the 2-MeTHF was combined with the product stream in the reactor. The combined organic stream was washed with 20% brine (1 Vol). The organic layer was polish-filtered through a ≤10 μm filter into a clean vessel.

In a separate vessel, 1.1 equivalents of 2-Naphthalenesulfonic acid hydrate was dissolved in THF (2 Vol). The solution was polish-filtered prior to use. The 2-naphthalenesulfonic acid hydrate THF solution was added into the product organic solution in the vessel over at least 2 h at 25±5° C. The batch temperature was adjusted to 60±5° C. and the batch was aged for 1±0.5 h. The batch temperature was adjusted to 20±5° C. over at least 2 h. The batch was filtered to collect the product. The collected filter cake was washed with THF (5.0 Vol) by displacement. The product cake was dried on a frit under vacuum/nitrogen stream until the water content was ≤1 wt % by LOD.

The yield of the product (R)-2-(3-(2-methoxyethoxy)-5-oxo-1,6-naphthyridin-6(5H)-yl)propanoic acid naphthalene-2-sulfonate, was 87%. The chiral purity was determined using chiral HPLC and was found to be 98-99% ee. The purity was determined using HPLC, and was found to be ≥98%.

Thus, Example 1 shows the synthesis of NAPA according to the disclosure.

46

Example 2

Synthesis of (R)—N'-(3-fluoro-5-(1-methyl-1H-pyrazol-4-yl)pyridin-2-yl)-2-(3-(2-methoxyethoxy)-5-oxo-1,6-naphthyridin-6(5H)-yl)propanehydrazide (HYDZ)

Scheme 2: Synthesis of (R)-N'-(3-fluoro-5-(1-methyl-1H-pyrazol-4-yl)pyridin-2-yl)-2-(3-(2-methoxyethoxy)-5-oxo-1,6-naphthyridin-6(5H)-yl)propanehydrazide

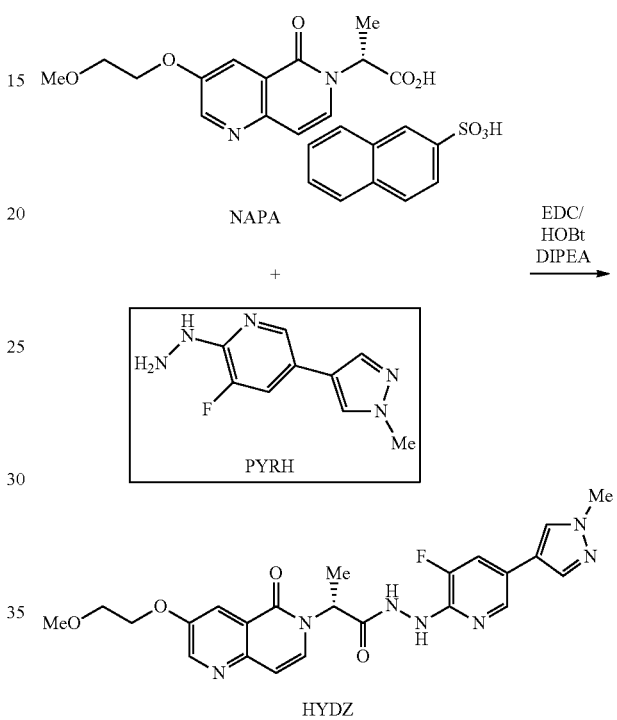

HYDZ was synthesized according to Scheme 2 by the following procedure. A 60 L jacket reactor was charged with 2805.0 g (1.0 equivalent) of (R)-2-(3-(2-methoxyethoxy)-5-oxo-1,6-naphthyridin-6(5H)-yl)propanoic acid 2-napsylate (NAPA) and N,N-dimethylacetamide (DMAC) (4.6 mL DMAC per gram of NAPA). Stirring and an $N_2$ sweep were initiated. 1.05 equivalents of N,N-diisopropylethylamine (DIPEA) was added while maintaining the batch temperature at less than 35° C. Initially the NAPA dissolves. A white precipitate formed while aging, but the precipitate had no impact on the reaction performance. 2197 g (1.10 equivalents) of 3-fluoro-2-hydrazinyl-5-(1-methyl-1H-pyrazol-4-yl)pyridine (PYRH) was added to the batch. The batch temperature was adjusted to 10±5° C. 2208 g (1.2 equivalents) of N-(3-dimethylaminopropyl)-N-ethylcarbodiimide hydrochloride (EDC) was added in four portions (approximately equal) over at least 1 h (about 20 min interval per portion) at 10±5° C.

The batch was aged until the amide conversion target was met. If the amide conversion target was not reached within 2 h, additional EDC was added until the conversion target was met. Once the target was met, the batch was heated to 55° C. until the solution was homogeneous. The batch was filtered through a ≤20μ in-line filter into a reactor. The vessel and filter were rinsed with DMAC (0.2 mL DMAC/g of NAPA). The batch temperature was adjusted to 45±5° C.

The reactor was charged with a seed slurry of (R)—N'-(3-fluoro-5-(1-methyl-1H-pyrazol-4-yl)pyridin-2-yl)-2-(3-

(2-methoxyethoxy)-5-oxo-1,6-naphthyridin-6(5H)-yl)propanehydrazide (HYDZ) (0.01 equivalents) in water (0.3 mL/g).

The batch was aged at 50±5° C. for at least 30 min. The batch temperature was adjusted to 20±5° C. over at least 2 h. The batch was aged at 20±5° C. for at least 30 min. 2.90 mL water per g was added at 25±5° C. over at least 2 h. The batch was aged at 20±5° C. for at least 1 h. The batch slurry was filtered to collect the product. The product was washed with 30% DMAC/H$_2$O (0.5 Vol) by displacement. The product cake was washed with water (3 Vol) by displacement. The product cake was dried on the frit under vacuum/nitrogen stream until the water content was ≤0.2 wt % as determined by Karl Fischer titration (KF). The product was a white, crystalline solid. The yield was about 83-84%. The ee was measured by HPLC and was found to be >99.8% ee. The purity was determined by HPLC and was found to be ≥99.8 LCAP (purity by LC area percentage).

Thus, Example 2 demonstrates the synthesis of HYDZ according to the disclosure.

Example 3

Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride salt (Compound A-HCL)—Route 1

Scheme 3 Route 1-Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride

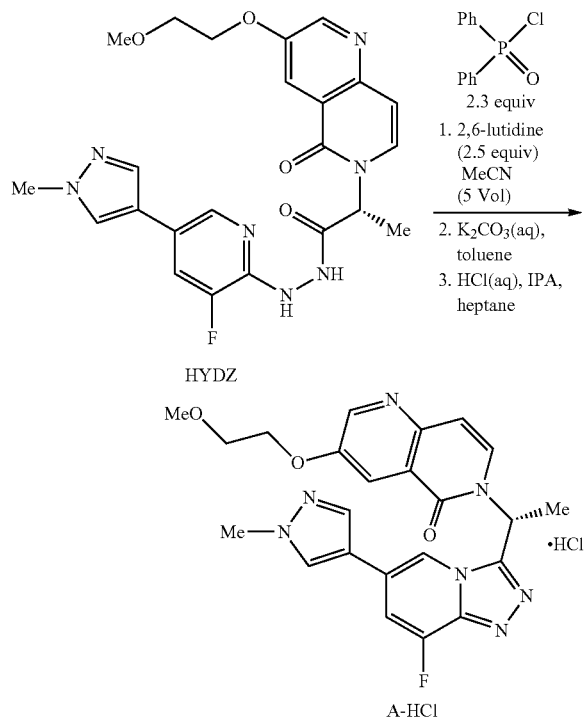

(R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride salt (Compound A-HCl) was synthesized according to Scheme 3, Route 1 by the following procedure. A 15 L reactor, Reactor 1, was charged with 750 g HYDZ and the reactor jacket temperature was adjusted to 20±5° C. A nitrogen sweep was initiated in Reactor 1 and the condenser coolant (at 5±5° C.) was started. Acetonitrile (3.4 L, 4.5 Vol) was added to Reactor 1 and stirring was initiated. 420 g (2.5 equivalents) of 2,6-lutidine was added to the reactor.

A solution of diphenylphosphinyl chloride Ph$_2$P(O)(Cl) was prepared by combining 850 g (2.3 equivalents) of Ph$_2$P(O)(Cl) and 300 g acetonitrile in an appropriate container. The contents of the PH$_2$P(O)(Cl) solution were added to Reactor 1. The jacket temperature was adjusted over 60±30 min until the reflux temperature of the batch (approximately 85° C.) was reached. The reaction was stirred for 14±6 h. The batch temperature was reduced to 75±5° C. and the batch was sampled for IPT analysis. The expected result was ≤2% HYDZ remaining. If the target was not met, the heating at reflux temperature was continued for 9±6 h. Sampling, analysis, and heating was repeated until a satisfactory conversion assay result was obtained (<10% HYDZ was considered satisfactory, <1% was actually achieved). The final sample was assayed for optical purity by HPLC, and was found to be >99.5% ee.

A K$_2$CO$_3$/KCl quench solution (5.0 Vol) was prepared in advance by combining 555 g (3.1 equivalents) of potassium carbonate with 335 g (2.9 equivalents) of potassium chloride and 3450 g of water in an appropriate container. The quench solution was added to Reactor 1 over at least 15 min, maintaining the batch temperature at 60±5° C. As the aqueous base reacted with excess acid some bubbling (CO$_2$) occurred. 3.0 L (4.0 Vol) of toluene was added to Reactor 1 at 65±5° C. A sample of the batch was taken for IPT analysis. The lower (aqueous) phase of the sample was assayed by pH probe (glass electrode). The pH was acceptable if in the range of pH 8-11. The upper (organic) phase of the sample was assayed by HPLC.

The batch was agitated for 20±10 min at 65±5° C. Stirring was stopped and the suspension was allowed to settle for at least 20 min. The aqueous phase was drained from Reactor 1 via a closed transfer into an appropriate inerted container. The remaining organic phase was drained from Reactor 1 via a closed transfer to an appropriate inerted container. The aqueous phase was transferred back into Reactor 1.

An aqueous cut wash was prepared in advance by combining 2.3 L (3.0 Vol) acetonitrile and 2.3 L (3.0 Vol) toluene in an appropriate container. The aqueous cut wash was added to Reactor 1. The batch was agitated for 20±10 min at 65±5° C. The stirring was stopped and the suspension was allowed to settle for at least 20 min. The lower (aqueous) phase was drained from Reactor 1 via a closed transfer into an appropriate inerted container. The organic phase was drained from Reactor 1 via a closed transfer to the inerted container containing the first organic cut. The combined mass of the two organic cuts was measured and the organic cuts were transferred back to Reactor 1. Agitation was initiated and the batch temperature was adjusted to 60±10° C. A sample of the batch was taken and tested for Compound A content by HPLC. The contents of Reactor 1 were distilled under vacuum (about 300-450 mmHg) to approximately 8 volumes while maintaining a batch temperature of 60±10° C. and a jacket temperature of less than 85° C. The final volume was between 8 and 12 volumes.

The nitrogen sweep in Reactor 1 was resumed and the batch temperature adjusted to 70±5° C. A sample of the batch was taken to determine the toluene content by GC. If the result was not within 0-10% area, the distillation was continued and concomitantly an equal volume of 2-propanol, up to 5 volumes, was added to maintain constant batch volume. Sampling, analysis, and distillation was repeated until the toluene content was within the 0-10% area window. After the distillation was complete, 540 g (450 mL, 3.5 equivalents) of hydrochloric acid was added to Reactor 1 over 45±15 min while maintaining a batch temperature at 75±5° C.

A Compound A-HCl seed suspension was prepared in advance by combining 7.5 g of Compound A-HCl and 380 mL (0.5 Vol) of 3 propanol in an appropriate container. The seed suspension was added to Reactor 1 at 75±5° C. The batch was agitated for 60±30 min at 75±5° C. The batch was cooled to 20±5° C. over 3±1 h. The batch was agitated for 30±15 min at 20±5° C. 2.6 L (3.5 Vol) of heptane was added to the batch over 2±1 h. The batch was then agitated for 60±30 min at 20±5° C. A sample of the batch was taken and filtered for IPT analysis. The filtrate was assayed for Compound A-HCl. If the amount of Compound A-HCl in the filtrate was greater than 5.0 mg/mL the batch was held at 20° C. for at least 4 h prior to filtration. If the amount of Compound A-HCl in the filtrate was in the range of 2-5 mg·ML, the contents of Reactor 1 were filtered through a ≤25 µm PTFE or PP filter cloth, sending the filtrate to an appropriate container.

A first cake wash was prepared in advance by combining 1.5 L (2.0 Vol) of 2-propanol and 1.5 L (2.0 Vol) of heptane in an appropriate container. The first cake wash was added to Reactor 1 and the contents were agitated for approximately 5 min at 20±5° C. The contents of Reactor 1 were transferred to the cake and filter. A second cake wash of 3.0 L (4.0 Vol) of heptane was added to Reactor 1 and the contents were agitated for approximately 5 min at 20±5° C. The contents of Reactor 1 were transferred to the cake and filter. The wet cake was dried under a flow of nitrogen and vacuum until the heptane content was less than 0.5 wt % as determined by GC. The dried yield was 701 g, 85% as a yellow powder. The dried material was assayed for chemical purity and potency by HPLC and for residual solvent content by GC. The isolated product was 88.8% Compound A-HCl, having 99.8% ee and 0.6% water.

Thus, Example 3 shows the synthesis of Compound A-HCL according to the disclosure.

Example 4

Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride salt (Compound A-HCL)—Route 2

Scheme 4: Route 2-Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride

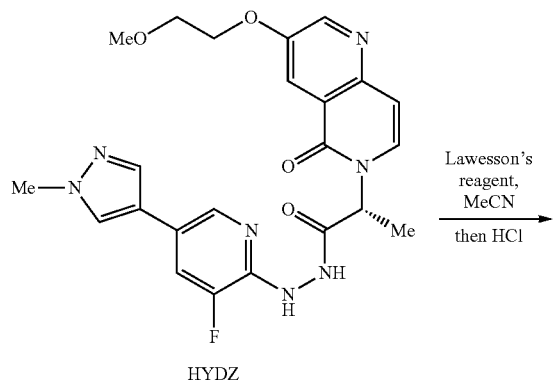

HYDZ

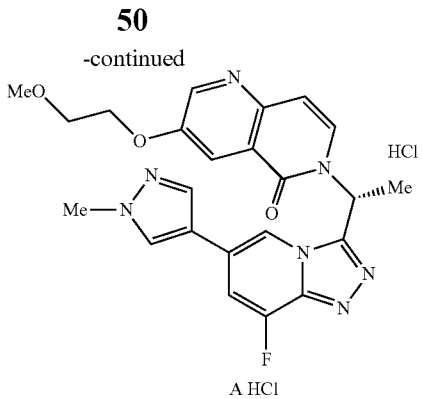

A HCl (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one hydrochloride salt was synthesized according to Scheme 4, Route 2, by the following procedure. A clean and dry 60 L reactor was fitted with a reflux condenser, nitrogen inlet, and vented to a scrubber (Reactor 1). The jacket temperature of Reactor 1 was set to 20° C. A scrubber was set up to the vent of Reactor 1, and aqueous bleach solution was charged to the scrubber. The circulating pump (commercial 5.25% NaOCl) was initiated. The scrubber pump was turned on and N$_2$ sweep on Reactor 1 was started. Reactor 1 was charged with 2597 g (0.52 equivalents) of Lawesson's reagent. Reactor 1 was then charged with 6000 g (1.0 equivalent) of HYDZ and 30 L (5.0 vol) acetonitrile (MeCN). Agitation of Reactor 1 was initiated. The reactor was heated to 50±5° C. and aged until an LC assay showed consumption of HYDZ (≥99% conversion).

The jacket temperature of a second clean and dry reactor, Reactor 2, was set to 50° C. The contents of Reactor 1 were transferred to Reactor 2 through a 5 micron inline filter. Reactor 1 was rinsed with MeCN, and the rinse was transferred through the inline filter to Reactor 2. Reactor 2 was charged with toluene. (31.7 Kg)

In a separate container a solution of 16.7% K$_2$CO$_3$ was prepared by adding 7200 g K$_2$CO$_3$ and 36 L water to the container and shaking the container well until all the solid was dissolved. Half of the contents of the K$_2$CO$_3$ solution was added to Reactor 2 over at least 10 min. The batch temperature of Reactor 2 was adjusted to 50±5° C. The batch in Reactor 2 was agitated at 50±5° C. for at least 1 h. The agitation was stopped and the batch in Reactor 2 was allowed to phase separate. The aqueous phase was removed. The remaining contents of the K$_2$CO$_3$ solution was added to Reactor 2 over at least 10 min. The batch temperature in Reactor 2 was adjusted to 50±5° C. The batch in Reactor 2 was agitated at 50±5° C. for at least 1 h. The agitation was stopped and the batch in Reactor 2 was allowed to phase separate. The aqueous phase was removed.

The jacket temperature of a clean and dry reactor, Reactor 3, was set to 50° C. The contents of Reactor 2 were transferred to Reactor 3 through a 5 micron in-line filter. The contents of Reactor 3 were distilled at reduced pressure. Isopropyl alcohol (IPA, 23.9 kg) was charged to Reactor 3 and then the batch was distilled down. IPA (23.2 kg) was again added to Reactor 3. The charge/distillation/charge cycle was repeated. The batch temperature in Reactor 3 was adjusted to 70±15° C. Reactor 3 was then charged with DI water (1.8 L). Concentrated HCl (1015 mL) was added to Reactor 3 over at least 15 min at 70±15° C.

A seed of the Compound A-HCl was prepared by combining a seed and IPA in a separate container. The Compound A-HCl seed was added to Reactor 3 as a slurry. The batch in Reactor 3 was aged at 70±15° C. for at least 15 min to ensure that the seed held. The batch in Reactor 3 was cooled to 20±5° C. over at least 1 h. Heptane (24.5 kg) was added to Reactor 3 at 20±5° C. over at least 1 h. The batch was aged at 20±5° C. for at least 15 min. The contents of Reactor 3 were filtered through an Aurora filter fitted with a ≤25 μm PTFE or PP filter cloth. The mother liquor was used to rinse Reactor 3.

A 50% v/v IPA/heptane solution was prepared, in advance, in a separate container by adding the IPA and heptane to the container and shaking. The filter cake from Reactor 3 was washed with the 50% IPA/heptane solution. If needed, the IPA/heptane mixture, or heptane alone, can be added to Reactor 3 prior to filtering the contents through the Aurora filter. The cake was washed with heptane. The cake was dried under nitrogen and vacuum until there was about ≤0.5 wt % heptane by GC analysis. The product was analyzed for purity and wt % assay by achiral HPLC, for wt % by QNMR, for water content by KF, for form by XRD, for chiral purity by chiral HPLC, and for K and P content by ICP elemental analysis.

Compound A-HCl had a purity of 99.56 area % and 88.3 wt % assay by achiral HPLC, and 89.9 wt % by QNMR. The water content was 0.99 wt % as determined by KF. The chiral purity was 99.9% ee as determined by chiral HPLC. The P and K content was found to be 171 ppm and 1356 ppm, respectively, as determined by ICP elemental analysis.

Thus, Example 4 shows the synthesis of Compound A-HCl according to the disclosure.

Example 5

Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (Compound A)—Route 3

Scheme 5: Route 3-Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (compound A)

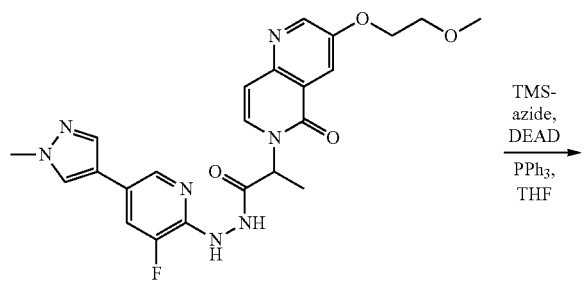

TMS-azide, DEAD
PPh₃, THF

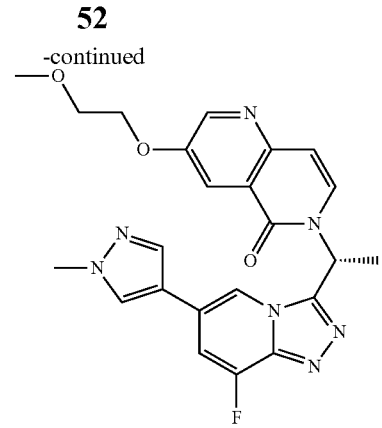

(R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one was synthesized according to Scheme 5, Route 3, by the following procedure. 0.760 g (1.6 mmol) N'-(3-fluoro-5-(1-methyl-1H-pyrazol-4-yl)pyridin-2-yl)-2-(3-(2-methoxyethoxy)-5-oxo-1,6-naphthyridin-6(5H)-yl)propanehydrazide (HYDZ) and 0.62 g (2.4 mmol) triphenylphosphine were taken up in 16 mL THF. 0.31 mL (2.4 mmol) trimethylsilyl (TMS)-azide was added, followed by addition of 0.37 mL (2.4 mmol) DEAD, maintaining the reaction temperature below 33° C. The reaction was stirred at room temperature for 50 minutes. The reaction mixture was concentrated in vacuo.

The crude material was taken up in dichloromethane and loaded onto silica gel. The crude material was purified via medium pressure liquid chromatography using a 90:10:1 DCM:MeOH:NH₄OH solvent system. 350 mg, (48% yield) of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one was collected as a tan solid. The (S) isomer was also collected. The product had a purity of 97% by HPLC.

Thus, Example 5 shows the synthesis of enantiomerically pure Compound A according to the disclosure.

Example 6

Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (Compound A) and the hydrochloride salt—Route 3

Scheme 6: Route 3-Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (compound A) and the hydrochloride salt 1.2 equiv
1.2 equiv PMe₃

MeCN/THF (7.5 Vol)
50° C., 1.5 h
99% conversion
91 LCAP

-continued

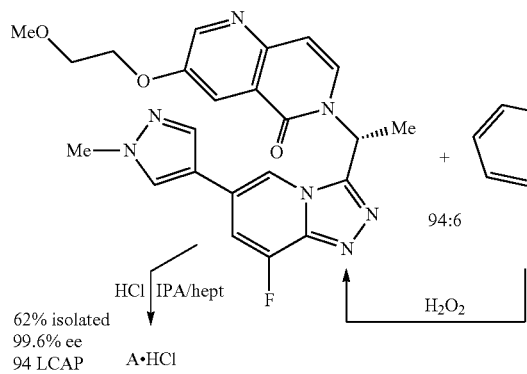

62% isolated
99.6% ee
94 LCAP

HCl | IPA/hept

A·HCl

94:6

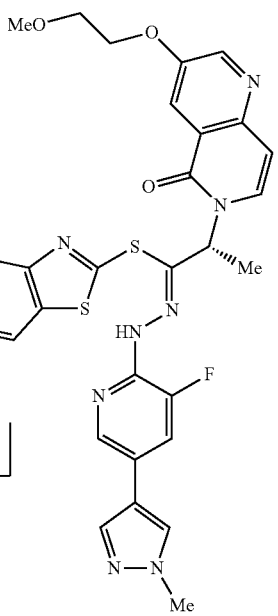

H₂O₂

(R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one was synthesized according to Scheme 6, Route 3, by the following procedure. Benzothiazyl disulfide (3.31 g, 9.97 mmol), HYDZ (4.0 g, 8.31 mmol), and a stir bar were added to a 50 mL 3-neck flask fitted with a reflux condenser topped with a nitrogen inlet, a thermocouple and a septum. The flask headspace was purged with nitrogen, and the solids were suspended in MeCN (20.00 mL, 5 mL/g) at ambient conditions. The flask contents were heated to 50° C. on a heating mantle. Finally, trimethylphosphine, solution in THF (9.97 ml, 9.97 mmol) was added dropwise by syringe pump with stirring over 1 h. An ice pack was affixed to the side of the flask in lieu of a reflux condenser. After about 0.5 h from addition, the resulting suspension was sampled and analyzed by, showing about 99% conversion of penultimate, and about 94% Compound A vs. benzothiazole-2-thiol ("BtSH") adduct selectivity.

After about 0.75 h from addition, the yellow reaction mixture was cooled to 0° C. in an ice bath, and 30% hydrogen peroxide in water (2.037 mL, 19.94 mmol) was added dropwise over 2 hours. The reaction solution was allowed to warm to room temperature overnight.

The suspension was heated to 30° C., held at that temperature for 3 h and then cooled to room temperature. After cooling was complete, an aliquot was filtered and the filtrate was analyzed by liquid chromatography, showing 99% Compound A vs. BtSH adduct (91% purity for Compound A overall).

A Celite filtration pad about 0.5" thick was set up on a 50 mL disposable filter frit and wetted with toluene (32.0 mL, 8 mL/g). The reaction suspension was transferred to the Celite pad and filtered to remove BtSH-related byproducts, washing with MeCN (2.000 mL, 0.5 mL/g). The filtrate was transferred to a 100 mL round bottom flask, and treated with 30 mL (7.5 Vol) of an aqueous quench solution consisting of sodium bicarbonate (7.5 ml, 8.93 mmol) and sodium thiosulfate (3.75 ml, 4.74 mmol) at overall about 5 wt % salt. The suspension was stirred for about 15 min and then the layers were allowed to separate. Once the layers were cut, the aqueous waste stream was analyzed by LC, showing 8% loss. The organic stream was similarly analyzed, showing 71% assay yield, implying about 20% loss to waste cake.

The organic cut was transferred to a 3-neck 50 mL round bottom flask with magnetic stir bar, thermocouple, and a shortpath distillation head with an ice-cooled receiving flask. The boiling flask contents were distilled at 55° C. and 300 torr pressure. The volume was reduced to 17 mL. The distillation was continued at constant volume with concomitant infusion of IPA (about 75 mL). The resulting thin suspension was filtered into a warm flask and water (0.8 mL) was added. The solution was heated to 80° C. After this temperature had been reached, hydrochloric acid, 37% concentrated (0.512 ml, 6.23 mmol) was added, and the solution was seeded with about 30 mg (about 1 wt %) Compound A-HCl salt. The seed held for 15 min. Next the suspension was cooled to 20° C. over 2 h. Finally heptane (17 mL, 6 Vol) was added over 2 h by syringe pump. The suspension was allowed to stir under ambient conditions overnight.

The yellow-green solid was filtered on an M-porosity glass filter frit. The wet cake was washed with 1:1 heptane/IPA (2 Vol, 5.5 mL) and then with 2 Vol additional heptane (5.5 mL). The cake was dried by passage of air. The dried cake (3.06 g, 78.5 wt %, 94 LC area % Compound A, 62% yield) was analyzed by chiral LC showing optical purity of 99.6% ee.

Thus, Example 6 shows the synthesis of enantiomerically pure Compound A and the hydrochloric salt thereof, according to the disclosure.

Example 7

Re-Crystallization of Compound A

Scheme 7: Re-crystallization of Compound A

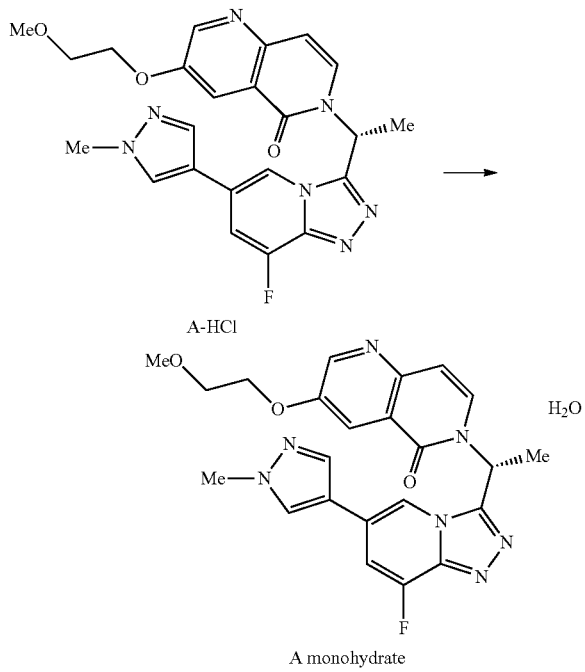

A-HCl

A monohydrate

Compound A-HCl was recrystallized to Compound A. A (60 L) jacketed reactor, Reactor 1, with a jacket temperature of 20° C. was charged with 5291 g, 1.0 equivalent of Compound A-HCl. 2 Vol (10.6 L) of IPA and 1 Vol (5.3 L) of water were added to Reactor 1 and agitation of Reactor 1 was initiated.

An aqueous $NaHCO_3$ solution was prepared in advance by charging $NaHCO_3$ (1112 g) and water (15.87 L, 3 Vol) into an appropriate container and shaking well until all solids were dissolved. The prepared $NaHCO_3$ solution was added to Reactor 1 over at least 30 min, maintaining the batch temperature below 30° C. The batch temperature was then adjusted to about 60° C. The reaction solution was filtered by transferring the contents of Reactor 1 through an in-line filter to a second reactor, Reactor 2, having a jacket temperature of 60±5° C. Reactor 2 was charged with water (21.16 L) over at least 30 min through an in-line filter, maintaining the batch temperature at approximately 60° C. After the addition, the batch temperature was adjusted to approximately 60° C.

A seed was prepared by combining Compound A seed (0.01 equivalents) and IPA/water (20:80) in an appropriate container, in an amount sufficient to obtain a suspension. The seed preparation step was performed in advance. Reactor 2 was charged with the seed slurry. The batch was aged at 55-60° C. for at least 15 min. The batch was cooled to 20±5° C. over at least 1 h. The batch from Reactor 2 was recirculated through a wet mill for at least 1 h, for example, using 1 fine rotor stator at 60 Hz, having a flow rate of 4 L/min, for about 150 min.

The reaction mixture was sampled for particle size distribution during the milling operation. The solids were analyzed by Malvern particle size distribution (PSD) and microscopic imaging. At the end of the milling operation a sample of the reaction mixture was again analyzed. The supernatant concentration was analyzed by HPLC, and the solids were analyzed by Malvern PSD and microscopic imaging to visualize the resulting crystals.

The batch temperature was adjusted to 35±5° C. and the batch was aged for at least 1 h. The batch was cooled to 20±5° C. over at least 2 h. The reaction mixture was sampled to determine the amount of product remaining in the supernatant. The supernatant concentration was analyzed by HPLC for target of ≤5 mg/mL Compound A in the supernatant. The contents of Reactor 2 were filtered through an Aurora filter fitted with a ≤25 μm PTFE or PP filter cloth.

A 20% v/v IPA/water solution was prepared and the filter cake from Reactor 2 was washed with the 20% IPA/water solution. The cake was then washed with water. If needed, the IPA/water solution, or water alone, can be added to Reactor 2 prior to filtering to rinse the contents of the reactor. The cake was dried under moist nitrogen and vacuum until target residual water and IPA levels were reached. The product had 3.2-4.2% water by KF analysis. The product was analyzed by GC for residual IPA (an acceptable about less than or equal to about 5000 ppm). The yield and purity were determined to be 100% and 99.69% (by HPLC), respectively.

Thus, Example 6 shows the recrystallization of Compound A from the HCl salt, Compound A-HCl, according to the disclosure.

Example 8

Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (Compound A)

Scheme 8 Synthesis of (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one

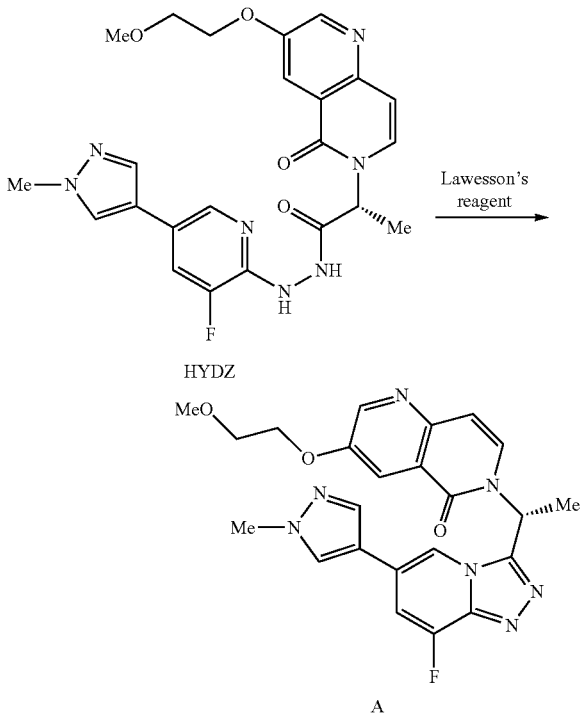

HYDZ

A (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one was synthesized according to Scheme 8 by the following procedure. A clean and dry 60 L reactor was fitted with a reflux condenser, nitrogen inlet, and vented to a scrubber (Reactor 1). The jacket temperature of Reactor 1 was set to 20° C. A scrubber was set up to the vent of Reactor 1, and aqueous bleach solution was charged to the scrubber. The circulating pump (commercial 5.25% NaOCl) was initiated. The scrubber pump was turned on and N₂ sweep on Reactor 1 was started. Reactor 1 was charged with 1599.5 g (0.52 equivalents) of Lawesson's reagent. Reactor 1 was then charged with 24.4 L acetonitrile (MeCN). Agitation of Reactor 1 was initiated. 3664.7 g (1.0 equivalent) of HYDZ was added to the reactor in portions over 1±0.5 h, using acetonitrile (5 L) as rinse. The reactor was heated to 50±5° C. and aged until an LC assay shows consumption of HYDZ (≥99% conversion).

The reactor was cooled to 20° C. and the reaction was assayed by HPLC for Compound A. The assay showed a 99% crude yield of Compound A.

The contents of Reactor 1 were transferred to second reactor, Reactor 2, through a 1 micron inline filter. Reactor 2 was charged with 2 L of water. Reactor 2 was connected to a batch concentrator and vacuum distilled until a final volume of about 10 L. The jacket temperature was 50° C. during distillation and the pot temperature was maintained below 50° C. The batch was then cooled to 20° C.

In a separate container a solution of 10% K₂CO₃ was prepared by adding 1160 g K₂CO₃ and 10450 mL water to the container and shaking the container well until all the solid was dissolved. The K₂CO₃ solution was added to Reactor 2 through an in-line filter (5 μm). 13 kg of purified water was added to the reactor through the in-line filter (5 μm).

A Compound A seed was added to the reactor through an addition port. The resulting slurry was aged for one hour during which crystallization was observed. The reactor was placed under vacuum and charged with 16 L of water. The resulting slurry was aged at 20° C. overnight. The product slurry was filtered through a 25 μm filter cloth and washed with 10 L of a 10% MeCN in water solution, followed by 12 L of water. The product was dried on a frit under a stream of ambient humidity filtered air.

Compound A was isolated as a monohydrate crystalline solid which reversibly dehydrates at <11% RH. After drying, there was 3.9 wt. % water present in constant weight solid as determined by KF. 3.317 kg, 89% yield, of Compound A was isolated as a pale yellow solid. The product had a purity of 99.4 wt. % as determined by LCAP.

Example 9

Synthesis of NAPH—Route 1

Scheme 9: Synthesis of NAPH-Route 1

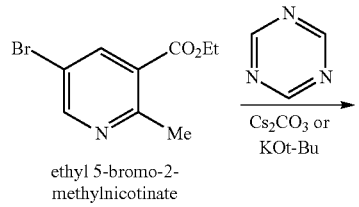

ethyl 5-bromo-2-methylnicotinate

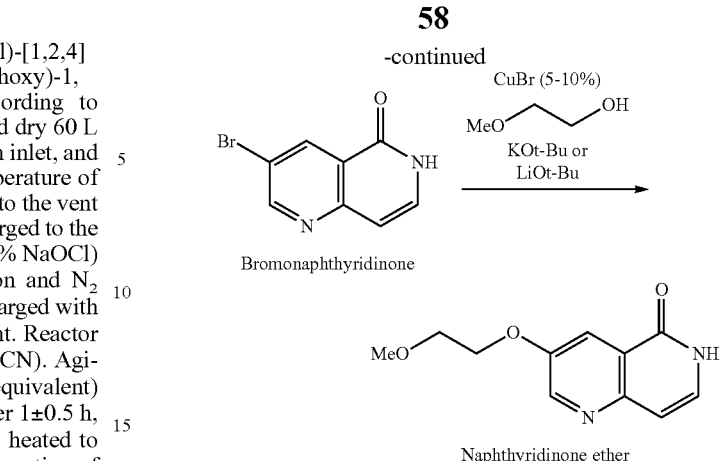

Bromonaphthyridinone

Naphthyridinone ether

The NAPH starting material for the synthesis of Compound A was synthesized according to Scheme 9, Route 1 by the following procedure. The jacket temperature of a 6 L jacketed reactor, Reactor 1, was set to 22° C. 2409 g (1.0 equiv) of ethyl 5-bromo-2-methylnicotinate, 824 g (1.0 equivalent) of triazine, and 3.6 L dimethyl sulfoxide (DMSO) were added to the reactor. The jacket temperature was adjusted to 45° C. The reactor was agitated until a homogenous solution resulted. Once complete dissolution has occurred (visually) the jacket of Reactor 1 was cooled to 22° C.

A second, 60 mL reactor, Reactor 2, was prepared. 8.0 L of water was charged to a scrubber. 4.0 L of 10 N sodium hydroxide was added to the scrubber and the scrubber was connected to Reactor 2. The cooling condenser was started. 6411.2 g of cesium carbonate and 12.0 L of DMSO were added to Reactor 2. Agitation of Reactor 2 was initiated. The batch temperature of Reactor 2 was adjusted to 80° C. The solution from Reactor 1 was added slowly over 1 h at 80° C., while monitoring the internal temperature. 1.2 L of DMSO was added to Reactor 1 as a rinse. The DMSO rinse was transferred from Reactor 1 to Reactor 2 over 6 min. Reactor 2 was agitated for more than 1 h and the conversion to 3-bromo-1,6-naphthyridin-5(6H)-one was monitored by HPLC until there was ≤1.0% ethyl 5-bromo-2-methylnicotinate remaining. When the reaction was complete the batch temperature was adjusted to 60° C. 24.0 L (10V) of water was added to Reactor 2 over 2 h, maintaining a reaction temperature of 60±5° C., using a peristaltic pump at 192 mL/min. Reactor 2 was cooled to 22° C. over 1 h 10 min. Stirring was continued at 22±5° C. until the supernatant assays for less than 3 mg/mL of 3-bromo-1,6-naphthyridin-5(6H)-one (analyzed by HPLC). The crystallized product was filtered through an Aurora filter fitted with 25 μm polypropylene filter cloth. The reactor and filter cake were washed with a 75 wt % H₂O-DMSO solution (3 Vol made from 1.6 L DMSO and 5.6 L water), followed by water (7.2 L, 3 Vol), and finally toluene (7.2 L, 3 Vol). The product cake was dried on the aurora filter under vacuum with a nitrogen stream at ambient temperature. The product was determined to be dry when the KF was <2.0 wt % water. 2194 g of 3-bromo-1,6-naphthyridin-5(6H)-one was isolated as a beige solid. The chemical purity was 99.73%. The adjusted yield was 2031.6 g (91.9%).

The jacket temperature of a 100 L reactor, Reactor 3, was set to 15±5° C. 6.45 L of 2-methoxyethanol was added to the reactor and agitation was initiated. (8107 g) lithium tert-butoxide was added portion-wise to the reactor, maintaining the reactor temperature in a range of 15° C. to 24° C. 3795 g of 3-bromo-1,6-naphthyridin-5(6H)-one was added to the reactor. 4 mL of 2-methoxyethanol was added to rinse the solids on the wall of the reactor. The reactor contents were stirred for at least 5 min. The reaction mixture was heated to distillation to remove t-BuOH and water, under 1 atm of nitrogen (jacket temperature 145° C.). Distillation continued until the pot temperature reached 122±3° C. The reactor contents were sampled and analyzed for water content by KF. The reaction mixture was cooled to less than 35° C. 243 g CuBr was added to the reactor. The reaction mixture was de-gassed by applying vacuum to 50 torr and backfilling with nitrogen three times. The batch was heated to 120±5° C. while maintaining the jacket temperature below 150° C. The batch was agitated (174 RPM) for 15.5 h. A sample of the reaction was taken and the reaction progress was monitored by HPLC. When the remaining 3-bromo-1,6-maphthyridin-5(6H)-one was less than 1%, the jacket temperature was cooled down to 25° C.

An Aurora filter was equipped with a 25 μm PTFE cloth and charged with Celite®. The reactor content was transferred onto the filter cloth and the filtrate was collected in the reactor. 800 mL of 2-methoxyethanol was added to the reactor and agitated. The reactor contents were transferred onto the filter and the filtrate was collected in the reactor. 5.6 L of acetic acid was added to the reactor to adjust the pH to 6.5, while maintaining the temperature at less than 32° C. The batch was then heated to 80° C. The reaction mixture was concentrated to 3.0±5 Vol (about 12 L) at 80±5° C. via distillation under vacuum.

In a separate container labeled as HEDTA Solution, 589.9 g of N-(2-hydroxyethyl)ethylenediaminetriacetic acid trisodium salt hydrate and 7660 mL water were mixed to prepare a clear solution. The HEDTA solution was slowly added to the reactor while maintaining the temperature of the batch at about 80-82° C. The batch was then cooled to 72° C.

An aqueous seed slurry of NAPH (31.3 g) in 200 mL of water was added to the reactor. The slurry was aged for 30±10 min. 20 L of water was slowly added to the reactor to maintain the temperature at 65±5° C. The batch was aged at 65±5° C. for 30 min. The batch was cooled to 20° C. over 1 h. The reactor contents were purged with compressed air for 1 h, and then the batch was further cooled to −15° C. and aged for 12.5 h. The batch was filtered through a centrifuge fitted with 25 μm PTFE filter cloth. 5.31 Kg of wet cake was collected (60-62 wt %). The wet cake was reslurried in 6V HEDTA solution and filtered through the centrifuge. The collected wet cake was dried in the centrifuge, and transferred to an Aurora filter for continued drying.

2.82 kg (76% isolated yield) of NAPH was collected having a 2.7% water content by KF.

Thus, Example 8 shows the synthesis of NAPH according to the examples.

Example 10

Synthesis of NAPH—Route 2

Scheme 10: Synthesis of NAPH via Route 2

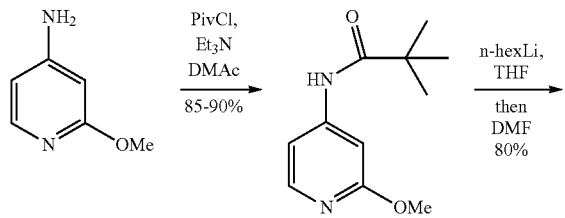

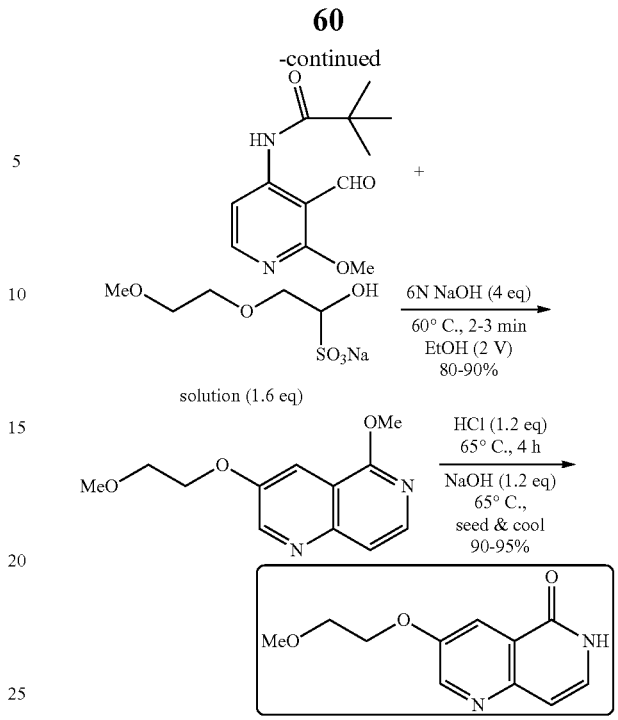

The NAPH starting material for the synthesis of Compound A was synthesized according to Scheme 10, Route 2, by the following procedure.

Preparation of protected 2-methoxy-pyridin-4ylamine. A 1600 L reactor was flushed with nitrogen and charged with 120 L of N,N-dimethylacetamide, 100.0 kg 2-methoxy-pyridin-4-ylamine, and 89.6 kg triethylamine, maintaining the temperature of the reactor at less than 20° C. In a separate container, 103.0 kg pivaloyl chloride was dissolved in 15.0 L of N,N-dimethylacetamide and cooled to less than 10° C. The pivaloyl chloride solution was added to the reactor using an addition funnel over 3.2 hours while maintaining the reactor temperature between 5° C. and 25° C. The addition funnel was washed with 15.0 L of N,N-dimethylacetamide, which was added to the reactor. The reaction was stirred for 2.3 hours at 20-25° C. A sample of the reaction was taken and analyzed for 2-methoxy-pyridin-4ylamine by TLC. No 2-methoxy-pyridin-4ylamine remained in the solution and the reaction was aged at 20-25° C. under nitrogen over night. 1200 L of deionized water was added to the reaction over 2 hours at while the reaction was maintained at 5-15° C. The resulting mixture was stirred at 15° C. for 2 hours and then cooled to 5° C. The reaction was centrifugated at 700-900 rpm in 3 batches. Each batch was washed 3 times with deionized water (3×167 L) at 800 rpm. The wet solids obtained were dried under vacuum at 55° C. for 18 hours in 2 batches, sieved and dried again under vacuum at 55° C. for 21 hours until the water content was ≤0.2% as determined by KF. 80.4 kg (89.7% yield) of the protected 2-methoxy-pyridin-4ylamine was collected as a white solid.

Preparation of protected 3-formyl-4-amino-2-methoxy-pyridine. A 1600 L reactor was flushed with nitrogen and charged with 1000 L of THF and 70.5 kg of the protected 2-methoxy-pyridin-4ylamine. The reaction was stirred for 10 min at 15-25° C. The reaction was cooled to −5° C. and 236.5 kg of n-hexyllithium (solution in hexane) was added over 11.5 hours while maintaining the temperature of the reaction at ≤−4° C. The reaction was maintained at ≤−4° C. for 2 hours. A sample of the reaction was quenched with D₂O and the extent of the ortho-lithiation was determined by ¹H NMR (98.2% conversion). 61.9 kg dimethylformamide (DMF) was added at ≤−4° C. over 3.2 h. After stirring 7.5 hours at ≤−4° C., a sample of the reaction was assayed for conversion by HPLC (98.5% conversion).

A 1600 L reactor, Reactor 2, was flushed with nitrogen and charged with 145 L THF and 203.4 kg of acetic acid. The resulting solution was cooled to −5° C. The content of the first reactor was transferred to Reactor 2 over 2.5 hours at 0° C. The first reactor was washed with 50 L THF and the washing was transferred into Reactor 2. 353 L deionized water was added to Reactor 2 while maintaining the temperature at less than 5° C. After 15 min of decantation, the aqueous layer was removed and the organic layer was concentrated at atmospheric pressure over 5 hours until the volume was 337 L. Isopropanol (350 L+355 L) was added and the reaction was again concentrated at atmospheric pressure until the volume was 337 L. Distillation was stopped and 90 L of isopropanol was added to the reactor at 75-94° C. 350 L of deionized water was added to the reactor at 60-80° C. over 1 h (the temperature was about 60-65° C. at the end of the addition). The reaction was cooled to 0-5° C. After 1 hour, the resulting suspension was filtered. Reactor 2 was washed twice with deionized water (2×140 L). The washings were used to rinse the solid on the filter. The wet solid was dried under vacuum at 50° C. for 15 h. 71.0 kg (80% yield) of the protected 3-formyl-4-amino-2-methoxypyridine was produced. The purity of the formyl substituted pyridine was found to be 92.7% by LCAP.

A 1600 L reactor, Reactor 3, was flushed with nitrogen and successively charged with 190 L ethanol, 128.7 kg of protected 3-formyl-4-amino-2-methoxypyridine, 144 L of deionized water and 278.2 kg of sodium hydroxide. The batch was heated to 60-65° C. and 329.8 kg of the bisulfite adduct was added over 1 h. After 1 h of stirring, a sample was taken for HPLC analysis which showed 100% conversion. The batch was aged 2 hours at 60-65° C., then was allowed to slowly cool down to 20-25° C. The batch was aged 12 h at 20-25° C. The batch was filtered and the reactor was washed with water (2×125 L). The washings were used to rinse the solid on the filter. The wet solid was transferred to the reactor with 500 L deionized water and heated to 45-50° C. for 1 h. The batch was allowed to return to 20-25° C. (24 h). The solid was filtered and the reactor was washed with deionized water (2×250 L). The washings were used to rinse the solid on the filter. 112.5 kg of wet white solid was obtained (containing 85.1 Kg (dry) of the naphthyridine, 72.3% yield, greater than 97% purity as determined by HPLC). The wet product was used directly in the next step, without drying.

A 1600 L reactor was flushed with nitrogen and charged with 417 L of deionized water and 112.5 kg of the wet napthyridine. The scrubber was filled with 700 L of water and 92.2 kg monoethanolamine. A solution of hydrochloric acid (46.6 kg diluted in 34 L of deionized water) was added to the reactor at 15-20° C. over 10 minutes. The batch was heated to 60-65° C. for 3 h. A sample of the batch was taken and contained no remaining starting material as determined by TLC. A solution of concentrated sodium hydroxide (58.2 kg in 31 L of deionized water) was added to the reactor at 60-65° C. 65% of the solution was added over 15 min and then the batch was seeded with crystallized NAPH. Crystallization was observed after 2.5 h and then the remaining 35% of the sodium hydroxide solution was added (pH—11.1). The batch was cooled to 25-30° C. and a solution of sodium phosphate monobasic (1.8 kg in 2.9 L of deionized water) was added over 25 min at 25-30° C.) (pH=6.75). The batch was stirred at 15-20° C. for 12 hours and filtered. The reactor was washed twice with deionized water (2×176 L). The washings were used to rinse the solid on the filter. The wet solid was dried under vacuum at 50° C. until the water content was <5% (by KF), to give 78.1 kg (73.8% yield, ≥95%)) of NAPH as a beige powder.

Thus, Example 9 shows the synthesis of NAPH according to the disclosure.

Example 11

Synthesis of (R)-2-(3-(2-methoxyethoxy)-5-oxo-1,6-naphthyridin-6(5H)-yl)propanoic acid naphthalene-2-sulfonate (NAPA)

Scheme 11: Synthesis of NAPA, Route 3

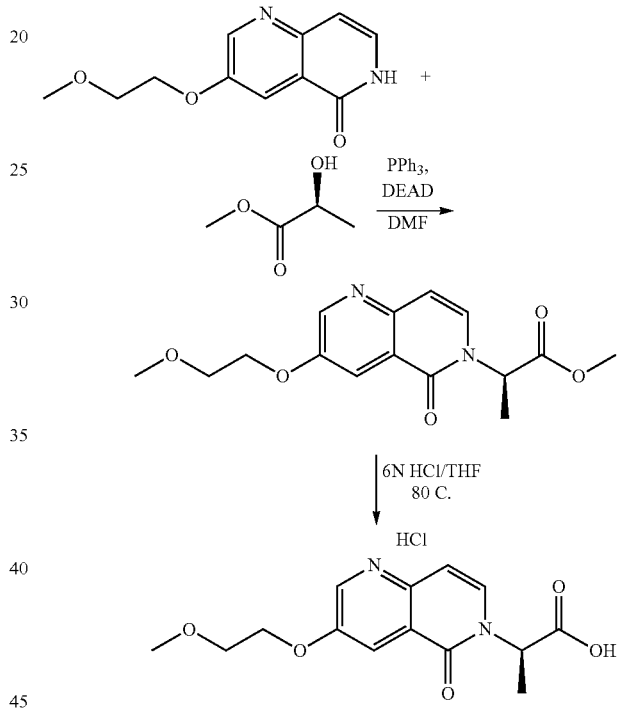

NAPA was synthesized according to Scheme 11, Route 3 by the following procedure. 4.75 g of 3-(2-Methoxyethoxy)-1,6-naphthyridin-5(6H)-one was suspended in 45 mL of DMF. 2.58 mL (s)-methyl lactate and 9.05 g triphenylphosphine were added to the suspension. The reaction mixture was cooled to 0° C. 5.12 mL diethyl azodicarboxylate (DEAD) was added dropwise via syringe. The mixture was stirred at 0° C. for 1 h. A sample of the reaction was taken and the reaction was determined to be complete by LCMS. The reaction mixture was concentrated under vacuum to give crude material as a yellow oil.

1 g of the crude material was loaded in dichloromethane onto a silia gel pre-column. The sample was purified using the Isco Combi-Flash System; column 40 g, solvent system hexane/ethyl acetate, gradient 0-100% ethyl acetate over 15 minutes. Product eluted at 100% ethyl acetate. The product fractions were combined and concentrated under vacuum. 256 mg of (R)-methyl 2-(3-(2-methoxyethoxy)-5-oxo-1,6-naphthyridin-6(5H)-yl)propanoate was collected as a pale yellow oil.

The remaining residue was partitioned between benzene and 6N aq hydrochloric acid (35.9 mL). The acidic layer was extracted with benzene (3×), diethyl ether (2×), ethyl acetate (2×) and dichloromethane (1×). The dichloromethane layer was back extracted with 6N aq. Hydrochloric acid (2×). The aqueous layer was diluted with THF (80 mL). The mixture was heated at 80° C. for 3 h. The reaction mixture was concentrated to remove the THF. The remaining acidic water layer was extracted with ethyl acetate and dichloromethane. The aqueous layer was concentrated under vacuum. The remaining solid was triturated with methanol. The mixture was filtered to remove the solid (naphthyridone). The methanol layer was concentrated under vacuum. The remaining solid was dried overnight on a freeze drier. 10.2 g of material was collected as a yellow solid. NAPA made up 72% of the material as determined by HPLC.

1.0 g of the crude material was dissolved in minimal hot iPrOH then filtered and cooled to RT. Crystallization didn't occur; therefore the solution was cooled in the freezer overnight. A yellow precipitate formed. The solid was collected on a glass frit and was washed with minimal iPrOH. 171 mg of yellow solid was collected, which was NAPA with a small amount of naphthyridone by LC-MS and $^1$H NMR.

Acid-base extraction. About 1 g of the crude material was dissolved in saturated aqueous sodium bicarbonate. The crude material was extracted with dichloromethane. The pH of the aqueous layer was adjusted to 6-7 with acetic acid then extracted with dichloromethane. 11 mg of the product was isolated; the majority of the product remained in the aqueous layer. The pH was reduced to approximately 4-5 with additional acetic acid. The aqueous layer was extracted with dichloromethane, ethyl acetate, and 15% methanol/dichloromethane. The organic layers were concentrated under vacuum to yield 260 mg of NAPA as the free base, as determined by LC-MS.

Thus, Example 10 shows the synthesis of NAPA according to the disclosure.

Example 12

Synthesis of Bisulfite Adduct

C. 88 mL of dimethyl sulfoxide was added to the flask via an addition funnel at less than −40° C. After the addition, the batch was stirred for 10 in at −60° C. 97 mL diethylene glycol monomethyl ether was added to the flask at less than −50° C. over 10 min. The resulting white slurry was stirred at −60° C. for 30 min. 229 mL triethylamine was added to the flask via an addition funnel at less than −30° C. over 1 h. The batch was warmed to RT. 300 mL MTBE was added to the flask and the batch was stirred for 15 min. The slurry was filtered through a fritted funnel and the cake was washed with 300 mL MTBE. The filtrate was concentrated to 350-400 g and then filtered again to remove triethylamine-HCl salt, and the solid was rinsed with MTBE, resulting in 357.7 g of a slightly yellow filtrate solution. The solution was assayed by QNMR and comprised 19 wt % (68 g) of the desired aldehyde (70% crude yield). The solution was concentrated to 150.2 g.

A 500 mL RBF was charged with 60.0 g sodium bisulfite and 150 mL of water to give a clear solution. The concentrated aldehyde solution was added to the aqueous bisulfite solution over 5 min. An exothermic temperature rising was observed up to 60° C. from 18° C. The solution was rinsed with 15 mL water. The resulting yellow solution was cooled to RT and was stirred under a sweep of nitrogen overnight. A QNMR of the solution was taken. The solution contained 43 wt. % of the bisulfite adduct (300 g, 70% yield).

Method 2

The bisulfite adduct was synthesized according to Method 2 of Scheme 12 by the following procedure. A 2500 L reactor was flushed with nitrogen and charged with 657.5 L of 2-methoxyethanol. 62.6 kg of lithium hydroxide monohydrate was added to the reactor while maintaining the temperature at less than 30° C. The reactor was heated to 113±7° C. 270 L of solvent were distilled over 1 h and then the reactor temperature was adjusted to 110° C. 269.4 kg of bromoacetaldehyde diethyl acetal was added over 16 minutes, maintaining the temperature between 110 and 120° C. The reaction was heated to reflux (115-127° C.) for 13 hours. A sample of the reaction was assayed and conversion to 2-(2-methoxyethoxy)acetaldehyde was found to be 98.3%. The reaction was cooled to 15-20° C. and 1305 L of methyl Scheme 12: Synthesis of bisulfite adduct

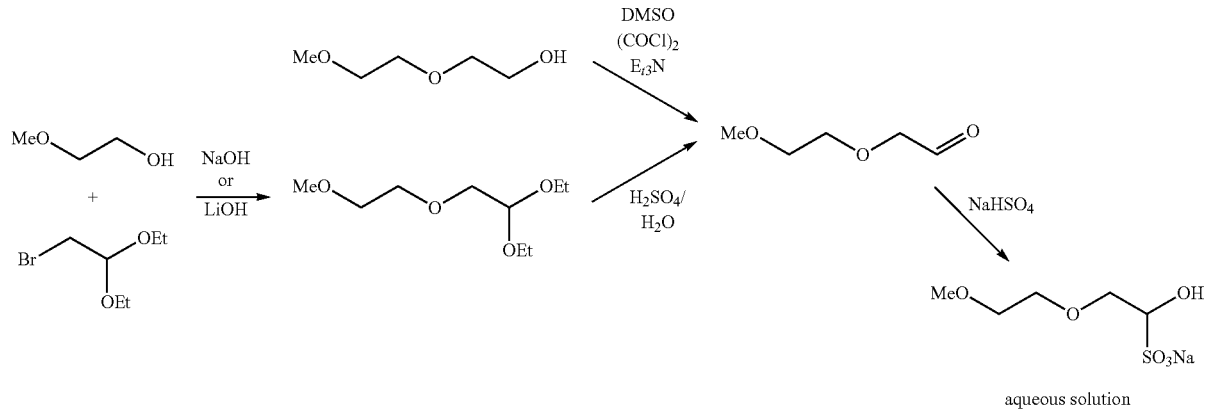

Method 1

The bisulfite adduct was synthesize according to Method 1 of Scheme 12 by the following procedure. A 2 L round-bottom flask (RBF) was purged with nitrogen and charged with 73.1 mL of reagent grade oxalyl chloride and 693 mL methylene chloride. The batch was cooled to less than −40° tert-butyl ether (MTBE) and 132 L of deionized water was added to the reactor. The reaction was stirred for 20 min and then was decanted. The aqueous layer was transferred into a 1600 L reactor and the organic layer was kept in the first reactor. The aqueous layer was extracted with 260 L of MTBE for 10 min. After 10 min decantation, the aqueous layer was removed and the organic layer was transferred to the first reactor. The mixed organic layers were washed twice, 15 min each, with a mixture of concentrated sodium hydroxide solution (2×17.3 kg) diluted in deionized water (2×120 L). The aqueous layers were removed, and the organic layer was concentrated at atmospheric pressure at 60-65° C. until the volume was 540 L. The organic layer was cooled down to 15-20° C. to give 2-(2-methoxyethoxy) acetaldehyde as an orange liquid solution (417.4 kg) containing 215.2 kg of pure product (87.3% yield) as determined by $^1$H NMR and HPLC assay.

A 1600 L reactor, Reactor 3, was flushed with nitrogen and charged with 595 L deionized water followed by 37.8 kg sulfuric acid over 25 minutes via addition funnel, while maintaining the temperature below 25° C. The addition funnel was washed with 124 L of deionized water and the washing was added to Reactor 3.

A 2500 L reactor, Reactor 4, was flushed with nitrogen and charged with 417.4 kg of the solution of the 2-(2-methoxyethoxy)acetaldehyde. The content of Reactor 3 was transferred into Reactor 4 over 25 min while maintaining the temperature of Reactor 4 below 35° C. The batch was aged at 30-35° C. for 3 hours. A sample of the batch was taken and assayed for 2-(2-methoxyethoxy)acetaldehyde. No 2-(2-methoxyethoxy)acetaldehyde remained. The batch was aged 5 h then cooled to 15-20° C.

A solution of sodium carbonate (39.2 kg) in deionized water (196 L) was prepared in Reactor 3. The sodium carbonate solution was transferred to Reactor 4 over 25 min while maintaining the temperature of Reactor 4 below 30° C. The pH of the resulting mixture was pH 5-6. 1.0 kg sodium carbonate was added by portion until the pH was about 7-8. A solution of sodium bisulfite (116.5 kg) in deionized water (218 L) was prepared in Reactor 3. The sodium bisulfite solution was transferred to Reactor 4 over 20 min while maintaining the temperature of Reactor 4 below 30° C. Reactor 3 was washed with deionized water (15 L) and the washing was added to Reactor 4. The batch was stirred for 1.2 hours. 23.3 kg sodium bisulfite was added to Reactor 4 and the batch was aged overnight. The batch was concentrated under vacuum at 30-50° C. over 6.5 hours until precipitation was observed. The batch was cooled to 0-10° C. at atmospheric pressure. After 30 min at 0-10° C., the suspension was filtered on 2 filters. Reactor 4 was washed with deionized water (2×23 L). The first washing was used to rinse the solid on the first filter and the second washing was used to rinse the solid on the second filter. Filtrates were joined to give 473.9 kg of an aqueous solution of the bisulfite adduct (202.5 kg of pure product, 76.3% yield) as a yellow liquid.

Thus, Example 11 shows the synthesis of the bisulfite adduct according to the invention.

Example 13

Synthesis of 2,3-difluoro-5-(1-methyl-1H-pyrazol-4-yl)pyridine

Scheme 13: Synthesis of 2,3-difluoro-5-(1-methyl-1H-pyrazol-4-yl)pyridine, precursor to PYRH

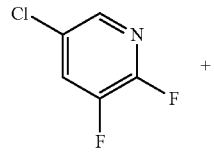

+

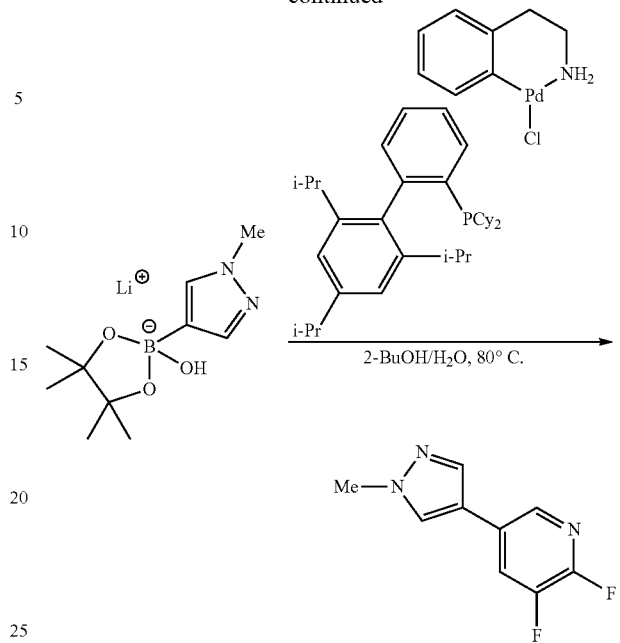

2,3-Difluoro-5-(1-methyl-1H-pyrazol-4-yl)pyridine was synthesized according to Scheme 13 by the following procedure. A boronic-ate complex slurry was prepared in a first 3-neck-2-L round-bottom flask (RBF #1). RBF #1 was charged with 141 g (66.4 wt %, 0.9 equivalents based on boronic ester) of lithium 2-hydroxy-4,4,5,5-tetramethyl-2-(1-methyl-1H-pyrazol-4-yl)-1,3,2-dioxaborolan-2-uide. 120 mL (1.6 Vol relative to 5-chloro-2,3-difluoropyridine) of nitrogen-sparged (2 h) 2-BuOH and 120 mL (1.6 Vol) nitrogen-sparged (2 h) water were added to RBF #1. Agitation and $N_2$ sweep were initiated. The reaction was aged at 20° C. for at least 30 min (reactions aged to 24 h were also successful).

A second 3-neck-2-L round-bottom flask (RBF #2) was charged with 1.48 g (0.004 equivalents) of Xphos-palladacycle and 450 mL (6 Vol relative to 5-chloro-2,3-difluoropyridine) of nitrogen-sparged (2 h) 2-BuOH. Vacuum/$N_2$ flush was cycled through RBF #2 three times to inert the RBF with $N_2$. The batch in RBF #2 was heated to 80° C. 75 g (1.0 equivalents) of 5-chloro-2,3-difluoropyridine was added to RBF #2.

The slurry of boronic-ate complex was transferred from RBF #1 to a 500 mL dropping funnel. RBF #1 was rinsed with 30 mL (0.4 Vol) 2-BuOH. Using the dropping funnel, the slurry of boronic-ate complex was added over 1 h to the hot solution mixture in RBF #2. After 1 h, 95% conversion was observed. If greater than 90% conversion was not observed, additional boronic-ate complex slurry was added (0.1 equivalents at a time with 1.6 Vol of 1:1 2-BuOH/water relative to boronic-ate complex). After the conversion was complete, the batch was cooled to 50° C. While cooling, 600 mL (8 Vol) of toluene was added to RBF #2. 300 mL (4 Vol) of 20% w/v NaHSO$_3$ in water was added to RBF #2 and the batch was stirred at 50° C. for at least 1 h. The batch was polish filtered using a 5 micron Whatman filter at 50° C., into a 2-L Atlas reactor. RBF #2 was rinsed with 30 mL (4.0 Vol) of a 1:1 2-BuOH:toluene solution. The temperature of the batch was adjusted to 50° C. in the Atlas reactor while stirring. The stirring was stopped and the phases were allowed to settle for at least 15 min while maintaining the batch at 50° C. The bottom, aqueous layer was separated from the batch. The Atlas reactor was charged with 300 mL (4 Vol) of a 20% w/v NaHSO₃ solution and the batch was stirred at 50° C. for 1 h. The agitation was stopped and the phases were allowed to settle for at least 15 min at 50° C. The bottom, aqueous layer was removed. Agitation was initiated and the Atlas reactor was charged with 200 mL (4 Vol) of 0.5 M KF while keeping the batch at 50° C. for at least 30 min. The agitation was stopped and the phases were allowed to settle for at least 15 min at 50° C. The bottom, aqueous layer was removed. Agitation was initiated and the reactor was charged with 300 mL (4 Vol) of water. The batch was aged at 50° C. for at least 30 min. Agitation was stopped and the phases were allowed to settle for at least 15 min at 50° C. The bottom, aqueous later was removed.

The organic phase was concentrated by distillation under reduced pressure (180 torr, jacket temp 70° C., internal temp about 50° C.) to a minimal stir volume (about 225 mL). 525 mL (7 Vol) of 2-BuOH was added to the Atlas reactor. The organic batch was again concentrated using reduced pressure (85-95 torr, jacket temp 75° C., internal temp about 55° C.) to a minimal stir volume (about 125 mL). The total volume of the batch was adjusted to 250 mL with 2-BuOH.

525 mL (7 Vol) heptane was added to the slurry mixture in the Atlas reactor. The jacket temperature was adjusted to 100° C. and the batch was aged for more than 15 min, until the batch became homogeneous. The batch was cooled to 20° C. over at least 3 h. A sample of the mixture was taken and the supernatant assayed for 2,3-difluoro-5-(1-methyl-1H-pyrazol-4-yl)pyridine. If the concentration was greater than 10 mg/mL, the aging was continued for at least 1 h until the supernatant concentration was less than 10 mg/mL. The batch was filtered using a medium frit. The filter cake was washed with 150 mL (2 Vol) 30% 2-BuOH/heptane solution followed by 150 mL (2 Vol) heptane. The filter cake was dried under N₂/vacuum. 76.64 g of 2,3-difluoro-5-(1-methyl-1H-pyrazol-4-yl)pyridine was isolated as a white solid (87% yield).

A 60 L jacketed reactor was fitted with a reflux condenser. The condenser cooling was initiated at 0±5° C. The reactor was charged with 2612 g (1 equivalent) of 2,3-difluoro-5-(1-methyl-1H-pyrazol-4-yl)pyridine and placed under an atmosphere of nitrogen. 31.7 L (12.2 Vol) water was added to the reactor and the resulting slurry was nitrogen sparged for 1 h with agitation. 7221 mL (6 equivalents) of hydrazine (35 wt % in water) was added to the reactor under a nitrogen atmosphere. The reactor was heated to 100° C. for 2±2 h until reaction was complete by HPLC analysis. The reactor was cooled to 20° C. over 2±1 h at a rate of 40° C./h. The reactor contents were stirred for 10±9 hours until the desired supernatant assay (<2 mg/mL PYRH in mother liquor). The reactor contents were filtered through an Aurora filter fitted with 25 µm polypropylene filter cloth. The collected filter cake was washed with 12.0 L (4.6 V) of water in three portions. The filter cake was dried on the Aurora filter for 4-24 h at 22±5° C., or until the product contained less than 0.5% water as determined by KF. The dry product was collected. 2.69 kg (97% yield) 2,3-Difluoro-5-(1-methyl-1H-pyrazol-4-yl)pyridine was collected as a white crystalline solid. The solid had a water content of 12 ppm as determined by KF.

Thus, Example 12 shows the synthesis of 2,3-Difluoro-5-(1-methyl-1H-pyrazol-4-yl)pyridine, a precursor to PYRH, according to the disclosure.

Example 14

Synthesis of PYRH—Route 2

Scheme 14: Synthesis of 3-fluoro-2-hydrazinyl-5-(1-methyl-1H-pyrazol-4-yl)-pyridine (PYRH)

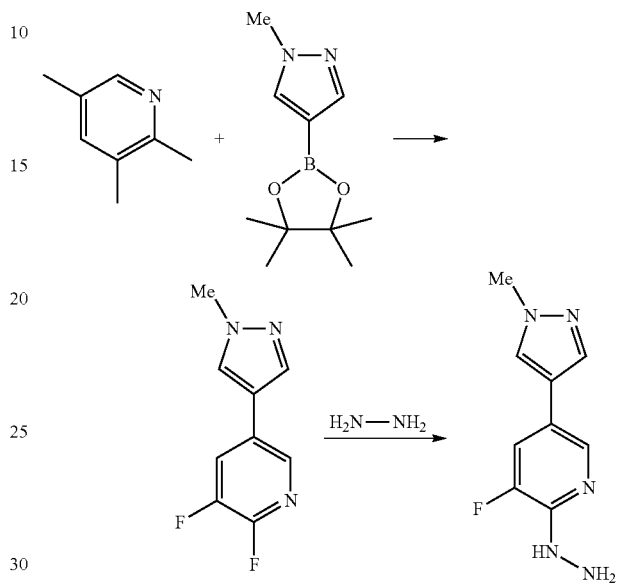

3-fluoro-2-hydrazinyl-5-(1-methyl-1H-pyrazol-4-yl)-pyridine was synthesized according to Scheme 14 by the following procedure. A 60 L jacketed reactor was fitted with a 5 L addition funnel and the jacket temperature was set to 20±5° C. 36.0 L (15 Vol) of 2-methyltetrahydrofuran was added to the reactor via a 20 µm inline filter with vacuum using polypropylene transfer lines. The solution was sparged by bubbling nitrogen through a dipstick in the solution for 1±0.5 h with agitation. After 1 h the dipstick was removed but the nitrogen sweep continued. 1.55 kg of sparged 2-MeTHF was removed to be used as rinse volumes. 36.7 g of Pd₂dba₃, 75.6 g X-Phos, 259 g of tetrabutylammonium bromide, and 7397 g of potassium phosphate tribasic were added to the reactor. The manhole was rinsed with 0.125 kg of sparged 2-MeTHF. The reactor was agitated and the nitrogen sweep continued for 1±0.5 h. Then the nitrogen sweep was stopped and the reaction left under a positive pressure of nitrogen.

3.6 L (1.5 Vol) of sparged water was prepared in advance by bubbling nitrogen through a 4 L bottle of water for 1±0.5 h. The nitrogen sparged water was transferred to the 5 L addition funnel via a 20 µm inline filter with vacuum using polypropylene transfer lines, then slowly added to the reaction while maintaining the internal temperature at 20±5° C. The 5 L addition funnel was replaced with a 2 L addition funnel. 2412 g of 5-chloro-2,3-difluoropyridine was added to the 2 L addition funnel. The 5-chloro-2,3-difluoropyridine was then added to the reaction through the 2 L addition funnel. The 2 L addition funnel was rinsed with 0.060 kg of sparged 2-MeTHF. 83.8 g (1.15 equivalents) of 1-methyl-pyrazole-4-boronic acid, pinacol ester was added to reactor, the reactor was swept with nitrogen for 1±0.5 h, then left under a positive pressure of nitrogen. The internal temperature of the reactor was adjusted to 70±5° C. The batch was agitated at 70±5° C. for at least 4 hours after the final reagent was added. A sample was taken from the reaction and the reaction progress assayed for conversion. The progress of the reaction was checked every 2 hours until the reaction was completed (e.g., greater than 99% conversion). The batch was cooled to 20±5° C.

A 20% w/v sodium bisulfite solution (12.0 L, 5 Vol) was prepared by charging 12.0 L of water then 2411 g sodium bisulfite to an appropriate container and agitating until homogeneous. The 20% sodium bisulfite solution was transferred into the reactor and agitated for 30 minutes. The agitation was stopped, the phases allowed to settle, and the aqueous phase was removed. A 0.5 M potassium fluoride solution (12.0 L, 5 Vol) was prepared by charging 12.0 L of water and 348 g of potassium fluoride to an appropriate container and agitating until homogenous. The 0.5 M potassium fluoride solution was transferred into the reactor and agitated for 30 min. The agitation was stopped, the phases were allowed to settle, and the aqueous phase was removed. A 25% w/v sodium chloride solution (12.0 L, 5 Vol) was prepared by charging an appropriate container with 12.0 L of water and 2999 g of sodium chloride and agitating until homogeneous. The 25% sodium chloride solution was transferred into the reactor and agitated for 30 min. The agitation was stopped, the phases were allowed to settle, and the aqueous phase was removed from the reactor.

The organic phase was distilled at constant volume (36 L, 15 Vol) while maintaining the internal temperature of the reactor at 50±5° C. by adjusting the vacuum pressure until no more than 0.3% of water remained. 2-Methyltetrahydrofuran was added to the reactor as needed to maintain constant volume. The batch was cooled to 20° C. and transferred into drums. The batch was transferred using a polish filter (using a 5 μm inline filter) into a 60 L jacketed reactor with a batched concentrator attached. 1.2 L of 2-MeTHF was used to rinse the drums. The batch was concentrated to about 9 Vol while maintaining the internal temperature of the vessel at 50±5° C. by adjusting the vacuum pressure. The batch was then distilled at constant volume (22.0 L, 9 Vol) while maintaining the internal temperature of the vessel at 50±5° C. by adjusting the vacuum pressure. Heptane was added with residual vacuum until a 15% 2-MeTHF:heptane supernatant mixture was obtained. The pressure was brought to atmospheric pressure under nitrogen. The reactor was cooled to 20±5° C. over 2±2 h. The batch was agitated at 20±5° C. until an assay of the supernatant indicated that the amount of product was 7 mg/mL 2,3-difluoro-5-(1-methyl-1H-pyrazol-4-yl)pyridine.

A 10% 2-MeTHF:heptane (7.2 L, 3 Vol) wash solution was prepared by mixing 720 mL of 2-MeTHF and 6.5 L of heptane. The batch slurry was filtered through an Aurora filter fitted with a 25 μm polypropylene filter cloth, resulting in heavy crystals that required pumping with a diaphragm pump using polypropylene transfer lines through the top of the reactor while stirring. The mother liquor was recycled to complete the transfer. The reactor and filter cake were washed with two portions of the 10% 2-MeTHF:heptane wash solution (3.6 L each). The product cake was dried on a frit under a nitrogen stream at ambient temperature. The 2,3-difluoro-5-(1-methyl-1H-pyrazol-4-yl)pyridine was determined to be dry when the ¹H NMR assay was ≤0.05±0.05. 2.635 kg was isolated as an off white crystalline solid (85% yield).

A 60 L jacketed reactor was fitted with a reflux condenser. The condenser cooling was initiated at 0±5° C. The reactor was charged with 2612 g (1 equivalent) of 2,3-difluoro-5-(1-methyl-1H-pyrazol-4-yl)pyridine and placed under an atmosphere of nitrogen. 31.7 L (12.2 Vol) water was added to the reactor and the resulting slurry was nitrogen sparged for 1 h with agitation. 7221 mL (6 equivalents) of hydrazine (35 wt % in water) was added to the reactor under a nitrogen atmosphere. The reactor was heated to 100° C. for 2±2 h until reaction was complete by HPLC analysis. The reactor was cooled to 20° C. over 2±1 h at a rate of 40° C./h. The reactor contents were stirred for 10±9 hours until the desired supernatant assay was reached (<2 mg/mL PYRH in mother liquor). The reactor contents were filtered through an Aurora filter fitted with 25 μm polypropylene filter cloth. The collected filter cake was washed with 12.0 L (4.6 V) of water in three portions. The filter cake was dried on the Aurora filter for 4-24 h at 22±5° C., or until the product contained less than 0.5% water as determined by KF. The dry product was collected. 2.69 kg was isolated as a white crystalline solid (97% yield). The water content was determined to be 12 ppm by KF.

Thus, Example 13 shows the synthesis of PYRH according to the disclosure.

Particular aspects and embodiments are described in the following paragraphs.

In one aspect, the present disclosure provides a method comprising reacting (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ"):

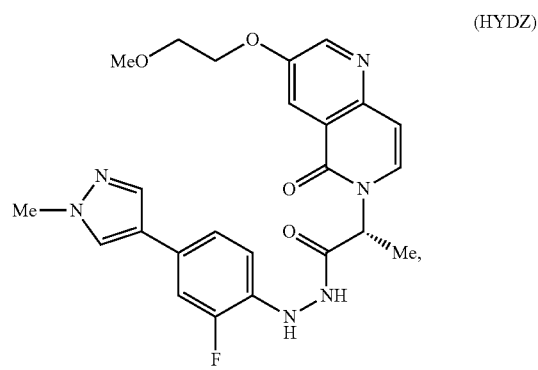 [SMILES: COCCOc1cnc2ccn([C@H](C)C(=O)NNc3ccc(-c4cnn(C)c4)cc3F)c(=O)c2c1]

(HYDZ)

under conditions sufficient to form (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

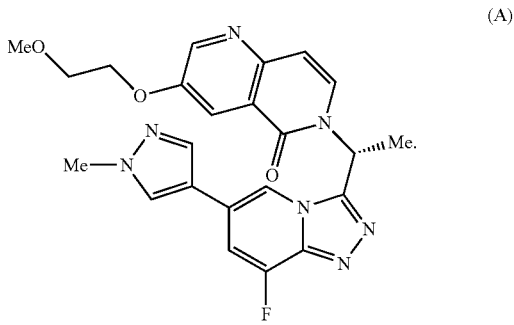 [SMILES: COCCOc1cnc2ccn([C@H](C)c3nnc4c(F)cc(-c5cnn(C)c5)cn34)c(=O)c2c1]

(A)

In one aspect, the reacting comprises contacting the HYDZ with a thiophosphetane compound. The thiophosphetane compound can be a 2,4-bis(aryl)-1,3-dithia-2,4-diphosphetane 2,4-disulfide compound. In a further aspect, the 2,4-bis(aryl)-1,3-dithia-2,4-diphosphetane 2,4-disulfide compound is:

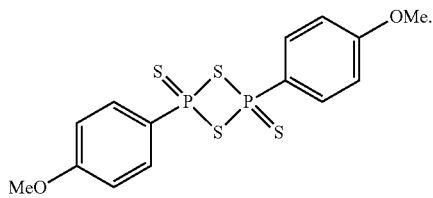 [SMILES: COc1ccc(P2(=S)SP(=S)(c3ccc(OC)cc3)S2)cc1]

In another aspect, the 2,4-bis(aryl)-1,3-diphosphetane 2,4-disulfide compound is:

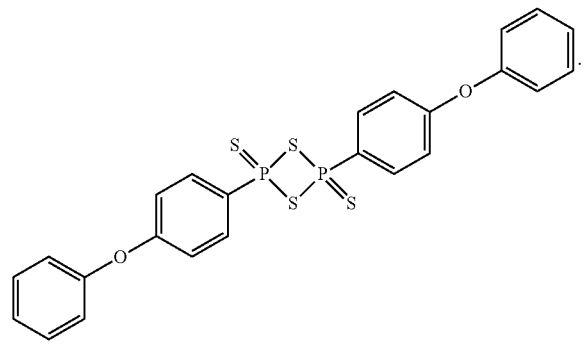 [SMILES: S=P1(c2ccc(Oc3ccccc3)cc2)SP(=S)(c2ccc(Oc3ccccc3)cc2)S1]

The present disclosure further provides that the thiophosphetane compound can be present in an amount of at least about 0.4 equivalents, or at least about 0.45 equivalents, or at least about 0.5 equivalents; or in a range of about 0.4 equivalents to about 0.65 equivalents, or about 0.45 equivalents to about 0.65 equivalents, or about 0.5 equivalents to about 0.55 equivalents, or about 0.52 equivalents.

In one aspect, the contacting occurs at a temperature in a range of 35° C. to 70° C., or 40° C. to 60° C., or 45° C. to 55° C. In another aspect, the contacting occurs by a process comprising adding the HYDZ to a slurry comprising the thiophosphetane compound. In a further aspect, the HYDZ is added to the slurry in portions. In another aspect, the slurry comprises acetonitrile. In still further aspect, the method can further comprise contacting Compound A with an acid under conditions sufficient to form a salt of Compound A. The acid can be selected from the group consisting of hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, maleic acid, and combinations thereof. In one aspect, the acid comprises hydrochloric acid. The present disclosure provides the yield of the salt of Compound A is at least about 80%, or at least about 90%, or at least about 95%, or at least about 99%. The purity of the salt of Compound A can be at least about 99%, or at least about 99.5%, or at least about 99.7%. Further, the optical purity of the salt of Compound A can be at least about 98%, or at least about 99%, or at least about 99.5%, or at least about 99.9% ee.

In another aspect, the methods of the present disclosure can further comprise contacting Compound A with a water-rich solvent having a pH of at least 7 under conditions sufficient to form the monohydrate form of Compound A. In one aspect, the solvent comprises water and acetonitrile, and wherein the water can be present in an amount of at least 80 wt. %. It is contemplated that the monohydrate form of Compound A has a purity of at least about 99.5%, or at least about 99.7%, or at least about 99.9%, or about 100%. In one aspect, the monohydrate form of Compound A has an optical purity of at least about 99.9% or about 100%.

The present disclosure further provides a method wherein the reacting comprises contacting the HYDZ with a phosphorus (V) dehydrating agent. In one aspect, the dehydrating agent comprises a compound having a structure:

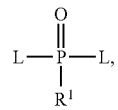

wherein each L independently is $C_{1-6}$alkyl, O—$C_{1-6}$alkyl, aryl, O-aryl, Br, Cl, or I; and $R^1$ is Cl, Br, or I. In a further aspect, each L can be selected from the group consisting of Me, Et, Pr, iPr, n-Bu, s-Bu, i-Bu, t-Bu, O-Me, O-Et, O—Pr, O-iPr, O-n-Bu, O-s-Bu, O-i-Bu, O-t-Bu, phenyl, O-phenyl, Br, and Cl. In still further aspect, each L is selected from the group consisting of Me, Et, t-Bu, O-Me, O-Et, O-t-Bu, phenyl, O-phenyl, Br, and Cl. In one aspect, $R^1$ can be Cl or Br. It is contemplated that the dehydrating agent may comprise diphenylphosphinyl chloride, $POCl_3$, or a combination thereof. In one aspect, the dehydrating agent is present in an amount of about 1.8 equivalents to about 3 equivalents. In a further aspect, the dehydrating agent is present in an amount of about 2.3 to about 2.5 equivalents. In one aspect of the present disclosure, the contacting occurs in the presence of a base. In a further aspect, the base is a pyridine. In one aspect, the base comprises 2,4-lutidine, 2,4,6-collidine, and a combination thereof. In one aspect of the present disclosure, the base is present in an amount of at least about 0.2 equivalents greater than the amount of the dehydrating agent. In another aspect, the base is present in an amount of about 2.5 to about 4.0 equivalents. In a further aspect, the base is present in an amount of about 2.5 to about 3.5 equivalents.

The present disclosure further provides a method wherein the contacting occurs in an amide, sulfolane, or nitrile solvent. In one aspect, the solvent comprises N-methyl-2-pyrrolidone ("NMP"), dimethylacetamide ("DMAc"), acetonitrile, propionitrile, and combinations thereof. In one aspect, the contacting occurs at a temperature in a range of 60° C. to 90° C. In another aspect, the temperature is in a range of 83° C. to 86° C. The methods of the present disclosure can further comprise contacting Compound A with an acid under conditions sufficient to form a salt of Compound A. The acid can be selected from the group consisting of hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, maleic acid, and combinations thereof. In one aspect, the acid comprises hydrochloric acid. In the method described above, the yield of the salt of Compound A can be at least about 85%, or at least about 90%, or at least about 95%, or at least about 99%. The purity of the salt of Compound A is at least about 88%, or at least about 90%, or at least about 95%. The optical purity of the salt of Compound A is at least about 99%, or at least about 99.5%, or at least about 99.8%, or at least about 99.9% ee.

The present disclosure further provides a method wherein the reacting comprises contacting the HYDZ with a phosphine:

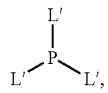

wherein each L' independently is an alkyl, aryl, or heteroaryl group; and an oxidant. In one aspect, each L' is a $C_{1-6}$alkyl group. In another aspect, each L' is a $C_{1-4}$alkyl group. In a further aspect, each L' is selected from the group consisting of Me, Et, Pr, iPr, n-Bu, s-Bu, i-Bu, and t-Bu. In one aspect the phosphine is trimethyl phosphine. In one aspect, each L' is an aryl group or a heteroaryl group. In another aspect, each L' is phenyl or pyridine. In a further aspect, the phosphine is triphenyl phosphine or diphenyl-2-pyridyl-phosphine. In one aspect, the phosphine is present in an amount in a range of about 1 equivalent to about 2 equivalents. In another aspect, the phosphine is present in an amount of about 1.1 equivalents, or about 1.2 equivalents, or about 1.3 equivalents, or about 1.4 equivalents, or about 1.5 equivalents, or about 1.6 equivalents, or about 1.7 equivalents, or about 1.8 equivalents, or about 1.9 equivalents. In one aspect, the oxidant is selected from the group consisting of benzoquinone, azodicarboxylate, aryl and/or heteroaryl disulfide, aryl and/or heteroaryl hypochlorothioite, and combinations thereof. In a further aspect, the benzoquinone comprises 2,3-dichloro-5,6-dicyanobenzoquinone ("DDQ"). In a further aspect, the azodicarboxylate comprises diethyl azodicarboxylate ("DEAD"), diisopropyl azodicarboxylate ("DIAD"), or di-(4-chlorobenzyl)azodicarboxylate. In a further aspect, the aryl and heteroaryl disulfide comprises benzothiazyl disulfide. In one aspect, the oxidant is present in an amount in a range of about 1 equivalent to about 2 equivalents. In another aspect, the oxidant is present in an amount of about 1.1 equivalents, or about 1.2 equivalents, or about 1.3 equivalents, or about 1.4 equivalents, or about 1.5 equivalents, or about 1.6 equivalents, or about 1.7 equivalents, or about 1.8 equivalents, or about 1.9 equivalents. In one aspect, the dehydrating further comprises an azide. In a further aspect, the azide is trimethylsilyl azide ("TMS azide"). In one aspect, the contacting occurs at a temperature in a range of 15° C. to 35° C., or 20° C. to 30° C., or 30° C. to 70° C., or 40° C. to 60° C. In one aspect, the contacting occurs in a solvent selected from a chlorinated solvent, an ether solvent, acetonitrile, and combinations thereof. In a further aspect, the ether solvent comprises tetrahydrofuran, diethyl ether, or a combination thereof. In one aspect, the reacting further comprising contacting Compound A with an acid under conditions sufficient to form a salt of Compound A. In a further aspect, the acid is selected from the group consisting of hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, maleic acid, and combinations thereof. In a further aspect, the acid comprises hydrochloric acid.

The present disclosure further comprises crystallizing Compound A in a solution comprising alcohol and water, under conditions sufficient to form a monohydrate form of Compound A:

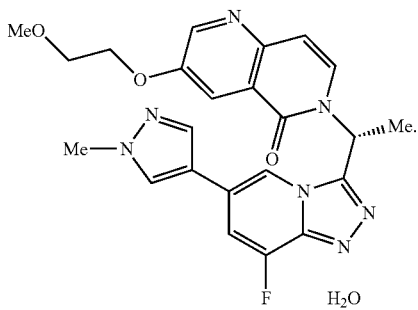

monohydrate

The alcohol includes methanol, ethanol, isopropanol, or combinations thereof. In one aspect, the alcohol comprises ethanol. In another aspect, the alcohol comprises isopropanol. The ratio of alcohol to water can be in a range of about 1:10 to about 10:1, or about 1:1, or about 1:2, or about 1:3, or about 1:4, or about 1:5, or about 1:6, or about 1:9, or about 1:8, or about 1:9, or about 1:10, or about 10:1, or about 9:1, or about 8:1, or about 7:1, or about 6:1, or about 5:1, or about 4:1, or about 3:1, or about 2:1. In one aspect, the ratio of alcohol to water is about 1:3, or about 1:4, or about 1:5, or about 1:6, or about 2:1. In a further aspect of the present disclosure, the yield of the monohydrate form of Compound A is at least about 95%, or at least about 97%, or at least about 99%. The purity of the monohydrate form of Compound A can be at least about 99%, or at least about 99.5%, or at least about 99.7, or at least about 99.9%. The optical purity of the monohydrate form of Compound A can be at least about 99.5%, or at least about 99.7%, or about 100% ee.

The methods of the present disclosure provide that the HYDZ can be formed by reacting (R)-2-(3-(2-methoxyethoxy)-5-oxo-1,6-naphthyridin-6(5H)-yl)propanoic acid ("NAPA"):

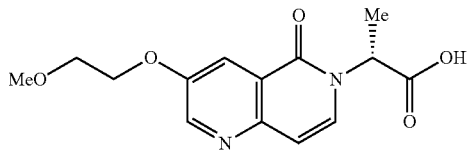

with 3-fluoro-2-hydrazinyl-5-(1-methyl-1H-pyrazl-4-yl)pyridine ("PYRH"):

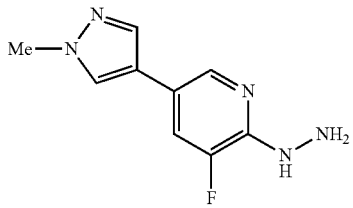

and a coupling reagent, and under conditions sufficient to form HYDZ:

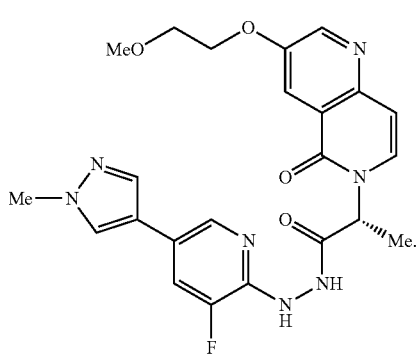

(HYDZ)

In one aspect, NAPA can be a zwitterion. In another aspect, NAPA can be a salt. The salt contemplated herein comprises HCl, HBr, a sulfonic acid, or diisopropylamine, or potassium cation. In one aspect, the salt comprises HCl. In a further aspect, the sulfonic acid salt may be selected from the group consisting of 2-naphthalenesulfonic acid, 1-naphthalenesulfonic acid, m-xylenesulfonic acid, p-toluene sulfonic acid, benzene sulfonic acid, 2-nitrobenzenesulfonic acid, 2,5-dichlorobenzene sulfonic acid, (−)-10-camphorsulfonic acid, (+)-camphor-10-sulfonic acid, p-chlorobenzene sulfonic acid, methanesulfonic acid, and combinations thereof. In still further aspect, the salt comprises 2-naphthalenesulfonic acid.

The present disclosure provides the coupling reagent may include a reagent selected from the group consisting of a carbodiimide reagent, a phosphonium reagent, a uronium reagent, an immonium reagent, an imidazolium reagent, an organophosphorus reagent, an acid chloride reagent, a chloroformate reagent, a pyridinium reagent, and combinations thereof. In one aspect, the carbodiimide reagent can be selected from the group consisting of N,N' dicyclohexylcarbodiimide ("DCC"), 1,3-diisopropylcarbodiimide ("DIC"), 1-ethyl-3-(3-dimethylaminopropyl)carbodiimide ("EDC"), isopropylcarbodiimide ("CIC"), and combinations thereof. In another aspect, the phosphonium reagent comprises (benzotriazol-1-yloxy)tris(dimethylamino)phosphonium hexafluorophosphate ("BOP") or benzotriazol-1-yl-oxytripyrrolidinophosphonium hexafluorophosphate ("PyBOP"). In a further aspect, the uronium reagent comprises 1-[Bis(dimethylamino)methylene]-1H-1,2,3-triazolo[4,5-b]pyridinium 3-oxid hexafluorophosphate ("HATU") or O-(Benzotriazol-1-yl)-N,N,N',N'-tetramethyluronium hexafluorophosphate ("HBTU"). In another aspect, the imidazolium reagent comprises 1,1'-carbonyldiimidazole ("CDI"). The acid chloride reagent can comprise pivaloyl chloride or 2, 4, 6-trimethylbenzoyl chloride. The chloroformate reagent comprises ethyl chloroformate or isobutyl chloroformate.

In the method described above, the reacting can be performed in the presence of a coupling additive. In one aspect, the coupling additive can be a benzotriazole, a dicarboximide, a succinimide, or a combination thereof. In one aspect, the coupling additive can be selected from the group consisting of N-hydroxysuccinimide ("HOSu"), N-hydroxy-5-norbornene-2,3-dicarboximide ("HONB"), 1-hydroxybenzotriazole ("HOBt"), 6-chloro-1-hydroxybenzotriazole ("Cl-HOBt"), 1-hydroxy-7-azabenzotriazole ("HOAt"), and combinations thereof. In a further aspect, the coupling additive comprises HOBt.

In one aspect, the reacting can occur in the presence of a base. In one aspect, the base comprises a tertiary amine. The tertiary amine can be selected from the group consisting of N,N-diisopropylethylamine ("DIEA"), triethylamine ("TEA"), N-methylmorpholine ("NMM"), Hünig base, and combinations thereof. In one aspect, the base can be present in an amount of at least about 1 equivalent. In a further aspect, the reacting can occur in an aprotic solvent. The aprotic solvent can be selected from the group consisting of acetonitrile, dichloromethane, tetrahydrofuran, dimethylacetamide ("DMAc"), and combinations thereof. In one aspect, the aprotic solvent can be DMAc. The yield of HYDZ can be at least about 75%, or at least about 85%, or at least about 90%, or at least about 95%. The purity of HYDZ can be at least about 95%, or at least about 97%, or at least about 99%, or at least about 99.5%, or about 100%. The optical purity of HYDZ is at least about 99%, or at least about 99.5%, or at least about 99.7%, or at least about 99.9% ee.

The present disclosure provides the methods wherein the NAPA is formed by admixing 3-(2-methoxyethoxy)-1,6-naphthyridin-5(6H)-one ("NAPH"):

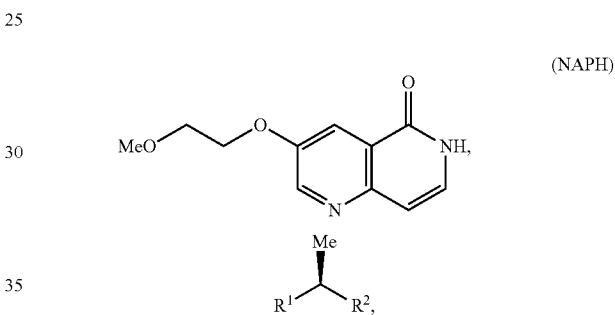

(NAPH)

and a base, under conditions sufficient to form NAPA:

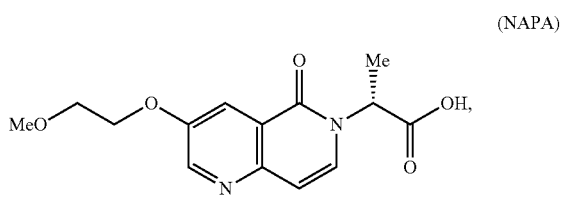 [SMILES: COCCOc1cnc2ccn([C@H](C)C(=O)O)c(=O)c2c1]

(NAPA)

wherein R$^1$ is Br, Cl, I, or OTf and

R$^2$ is COOH or C$_{1-3}$alkyl ester, and when R$^2$ is C$_{1-3}$alkyl ester, the method of forming the NAPA further comprises hydrolyzing the C$_{1-3}$alkyl ester to form an acid. In one aspect, R$^1$ can be Cl. In another aspect, R$^1$ can be Br. In a further aspect, R$^1$ can be I. In a further aspect, R$^1$ can be OTf. In one aspect of the present disclosure R$^2$ can be COOH. In one aspect,

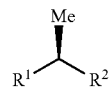

can be

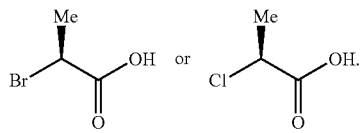

In one aspect, R² can be C₁₋₃alkyl ester. In one aspect, R² can be COOCH₃ or COOCH₂CH₃. In one aspect,

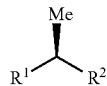

can be

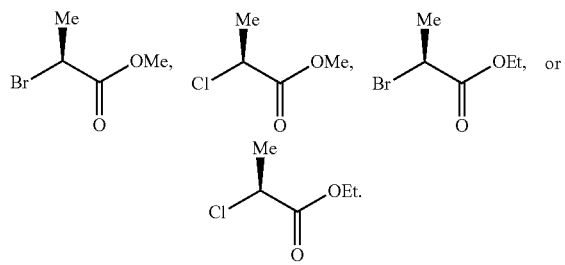

The base can comprise a strong inorganic base. In one aspect, the base can be selected from the group consisting of KOtBu, NaOtBu, LiOtBu, Mg(OtBu)₂, Al(OtBu)₃, NaO-SiMe₃, Cs₂CO₃, potassium bis(trimethylsilyl)amide ("KHMDS"), sodium bis(trimethylsilyl)amide ("NaHMDS"), lithium bis(trimethylsilyl)amide ("LiHMDS"), and combinations thereof. In one aspect, the base comprises Mg(OtBu)₂ and one or both of NaOtBu and KOtBu. In another aspect, the base comprises Mg(OtBu)₂ and one of NaOtBu and KOtBu. The ratio of Mg(OtBu)₂ to NaOtBu or KOtBu can be in a range of about 1.5:1 to about 2.5:1, or about 2:1. The admixing can occur at a temperature in a range of 20° C. to 80° C., or 25° C. to 60° C., or 25° C. to 45° C., or 25° C. to 35° C. In one aspect, the hydrolyzing occurs under acidic conditions. The yield of NAPA can be at least about 80%, or at least about 90%, or at least about 95%, or at least about 97%. The purity of NAPA can be at least about 95%, or at least about 97%, or at least about 99%, or at least about 99.5%, or about 100%. The optical purity of NAPA is at least about 90%, or at least about 95%, or at least about 97%, or at least about 99%, or at least about 99.5% ee.

The present disclosure provides the methods wherein the PYRH is formed by
(i) admixing

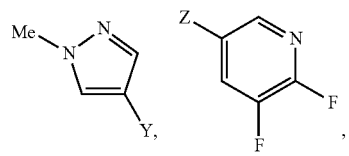

and a catalyst, under conditions sufficient to form an intermediate:
wherein:

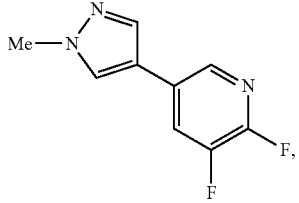 [SMILES: Cn1cc(-c2cnc(F)c(F)c2)cn1]

(a) Y is F, Cl, Br, I, or OTf, and Z comprises boronic acid, boronic ester, magnesium, zinc, zirconium, tin, or silicon; or
(b) Y comprises boronic acid, boronic ester, magnesium, zinc, zirconium, tin, or silicon, and Z is F, Cl, Br, I, or OTf; and (ii) admixing

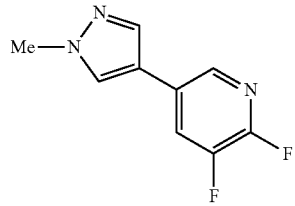 [SMILES: Cn1cc(-c2cnc(F)c(F)c2)cn1]

and H₂NNH₂, under conditions sufficient to form PYRH:

(PYRH)

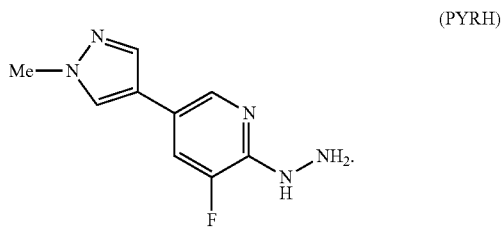 [SMILES: Cn1cc(-c2cnc(NN)c(F)c2)cn1]

In one aspect, the catalyst comprises palladium (0), palladium (II), nickel, copper, or iron. In a further aspect, the catalyst comprises palladium (0) or palladium (II). In another aspect, the catalyst comprises Pd₂(dba)₃, Pd(PPh₃), a Pd catalyst having at least one phoshpine ligand, PEPPSI-SIPr, or a palladacycle selected from the group consisting of a DavePhos, a XPhos, a SPhos, a JohnPhos, a RuPhos, a BrettPhos, a JackiePhos, a CPhos, and combinations thereof. In one aspect, the catalyst comprises an X-Phos palladacycle. The methods further provide that the admixing in step (i) can occur in the present of a base. In one aspect, the base is selected from the group consisting of K₃PO₄, CsF, Cs₂CO₃, and combinations thereof. In the method described above, Y can be Cl, Br, I, or OTf, and Z can comprise boron, magnesium, zinc, zirconium, tin, or silicon. In one aspect, Y can be Cl. In another aspect, Y can be Br. In a further aspect, Y can be I. In another aspect, Y can be OTf. Z can comprise boronic acid, boronic ester, or boronate. In one aspect, Z is a boronic acid. In another aspect, Z is a boronic ester selected from pinacolborane and catecholborane. In a further aspect, Z is a boronate selected from the group consisting of 9-borabicyclo[3.3.1]nonane ("9-BBN"), an N-methyliminodiacetic acid boronate ("MIDA boronate"), and 2-hydroxy-4,4,5,5-tetramethyl-2-(1-methyl-1H-pyrazol-4-yl)-1,3,2-dioxaborolan-2-uide:

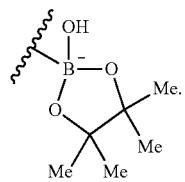 [SMILES: *[B-]1(O)OC(C)(C)C(C)(C)O1]

In one aspect, Z is

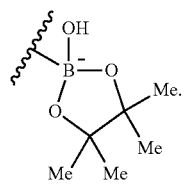

Z can comprise magnesium, zinc, zirconium, tin, or silicon. Y can comprise boron, magnesium, zinc, zirconium, tin, or silicon, and Z is Cl, Br, I, or OTf. In one aspect, Z may be Cl. In another aspect, Z may be Br. In another aspect, Z may be I. In a further aspect, Z is OTf. Y can comprise boronic acid, boronic ester, or boronate. In one aspect, Y is a boronic acid. In another aspect, Y is a boronic ester selected from pinacolborane and catecholborane. In a further aspect, Y is a boronate selected from the group consisting of 9-borabicyclo[3.3.1]nonane ("9-BBN"), an N-methyliminodiacetic acid boronate ("MIDA boronate"), and 2-hydroxy-4,4,5,5-tetramethyl-2-(1-methyl-1H-pyrazol-4-yl)-1,3,2-dioxaborolan-2-uide:

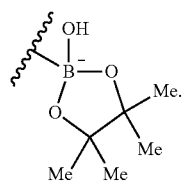 [SMILES: *[B-]1(O)OC(C)(C)C(C)(C)O1]

In one aspect, Y is

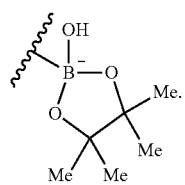

In one aspect, Y can comprise magnesium, zinc, zirconium, tin, or silicon.

The present disclosure discloses that the admixing step in (i) occurs in a solvent selected from the group consisting of dioxane, water, toluene, tetrahydrofuran, 2-methyltetrahydrofuran, n-heptane, and combinations thereof. In one aspect, the solvent comprises 2-methyltetrahydrofuran. In one aspect, the admixing in step (i) occurs in the presence of a phase transfer catalyst. The phase transfer catalyst can comprise, e.g., a quaternary ammonium salt. In another aspect, the phase transfer catalyst comprises tetrabutylammonium bromide ("TBAB"). In one aspect, the admixing in step (i) can occur in a solvent comprising alcohol and water.

The alcohol can be selected from the group consisting of 1-butanol, 2-butanol, and combinations thereof. In one aspect, the admixing in step (i) occurs at a temperature in a range of 60° C. to 80° C., or 65° C. to 75° C. The yield of the intermediate can be at least about 80%, or at least about 90%, or at least about 95%, or at least about 97%. The purity of the intermediate is at least about 97%, or at least about 98%, or at least about 99%. In one aspect, the hydrazine can be present in an amount of at least about 1 equivalent, or at least about 2 equivalents, or at least about 3 equivalents, or at least about 4 equivalents, or at least about 5 equivalents, or at least about 6 equivalents, or at least about 7 equivalents. In another aspect, the hydrazine can be present in an amount of at least about 3 equivalents, or at least about 4 equivalents, or at least about 5 equivalents, or at least about 6 equivalents.

In one aspect, the admixing in step (ii) can occur at a temperature of at least 70° C., or at least 80° C., or at least 90° C., or at least 100° C., or at least 110° C. It is provided that the admixing in step (ii) can occur in a solvent comprising water and alcohol. The alcohol can be selected from the group consisting of methanol, ethanol, propanol, isopropanol, n-butanol, 2-butanol, and combinations thereof. In one aspect, the solvent comprises water and methanol. The yield of PYRH is at least about 90%, or at least about 95%, or at least about 97%, or at least about 99%. In one aspect, the purity of PYRH can be at least about 97%, or at least about 99%, or at least about 99.5%, or about 100%.

The present disclosure provides methods wherein the NAPH is formed by
(i) admixing a methylnicotinate of Formula (I):

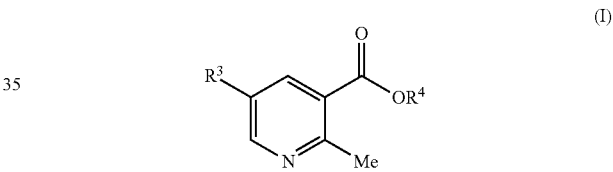

wherein $R^3$ is Cl, Br, or I, and $R^4$ is alkyl;
with 1,3,5-triazine, and a base, under conditions sufficient to form a naphthyridinone of Formula (II):

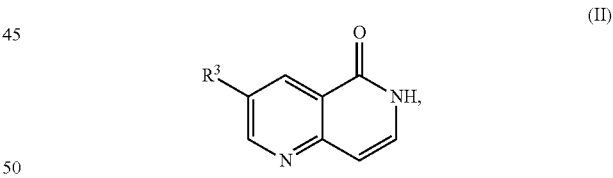

and
(ii) admixing the naphthyridinone of Formula (II) with methoxyethanol, a base, and a copper (I) catalyst, under conditions sufficient to form NAPH:

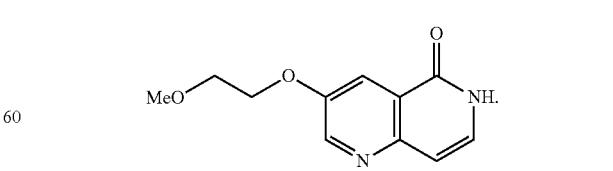

In one aspect, $R^3$ can be selected from the group consisting of Br, Cl, and I. In one aspect, $R^4$ can be a $C_{1-4}$ alkyl. For example, $R^4$ can be selected from the group consisting of Me, Et, n-Pr, and n-Bu. In a further aspect of the present disclosure, the copper (I) catalyst can be selected from the group consisting of CuBr, CuBr-DMS, Cu(OAc), Cu(OTf) and combinations thereof. In one aspect, the copper (I) catalyst further comprises a ligand. In one aspect, the ligand is selected from the group consisting of one or both of 1,10-phenanthroline and 3,4,7,8-tetramethyl-1,10-phenanthroline. In a further aspect of the present disclosure, the base in step (i) can be selected from the group consisting of $Cs_2CO_3$, KOtBu, $K_3PO_4$, $K_2CO_3$, and combinations thereof. In one aspect, the base is $Cs_2CO_3$ or KOtBu. In a further aspect of the present disclosure, the admixing in step (i) can occur in a polar aprotic solvent. In one aspect, the solvent can comprise dimethyl sulfoxide or dimethylacetamide. The present disclosure provides that the admixing in step (i) can occur at a temperature in a range of about 15° C. to about 100° C., or about 80° C. In one aspect, the base in step (ii) can be selected from the group consisting of KH, NaH, LiH, KOtBu, NaOtBu, LiOtBu, BuLi, HexLi, $Cs_2CO_3$, lithium bis(trimethylsilyl)amide ("LiHMDS"), sodium bis(trimethylsilyl)amide ("NaHMDS"), potassium bis(trimethylsilyl)amide ("KHMDS"), lithium diisopropylamide ("LDA"), lithium tetramethylpiperidide ("LiTMP"), LiOH, NaOH, KOH, CsOH, and combinations thereof. In one aspect, the base in step (ii) can be selected from the group consisting of $Cs_2CO_3$, LiOtBu, LiHMDS, KOtBu, and combinations thereof. In one aspect, the admixing in step (ii) can occur in an ether solvent having a boiling point above about 85° C. In one aspect, the solvent can be selected from the group consisting of neat 2-methoxyethanol, diglyme, dioxane, and combinations thereof. The admixing in step (ii) can occur at a temperature in a range of about 50° C. to about 130° C., about 80° C. to about 120° C., or about 114° C. The yield of NAPH can be at least about 56%, 75%, 85%, or 95%. NAPH has a purity of at least about 90%, 95%, or 97%.

The present disclosure provides the methods, wherein the NAPH is formed by:
(i) admixing protected N-(3-formyl-4-amino-2-alkoxy)pyridine:

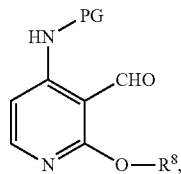

wherein PG is a protecting group and $R^8$ is alkyl, with 1-hydroxy-2-(2-methoxyethoxy)ethane-1-sulfonate:

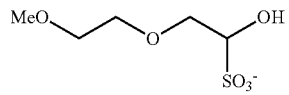

and base, under conditions sufficient to form a naphthyridine of Formula (III):

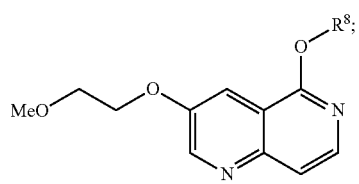

and
(ii) acidifying the naphthyridine of Formula (III), under conditions sufficient to form NAPH:

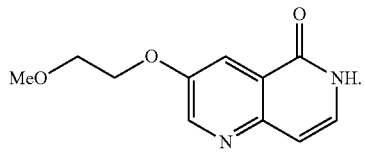

In one aspect, PG is selected from the group consisting of PivCl, PivBr, and Piv anhydride. In one aspect, $R^8$ is a $C_{1-4}$ alkyl. $R^8$ can be $CH_3$. In another aspect,

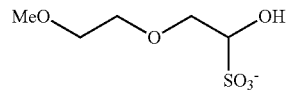

can be present in an amount of about 1 equivalent to about 5 equivalents, or about 1.2 equivalents. In a further aspect, the base is selected from the group consisting of NaOH, KOH, $K_3PO_4$, LiOH, CsOH, and RbOH, and a combination thereof. In one aspect, the admixing occurs in a water soluble solvent selected from the group consisting of methanol, ethanol, isopropanol, acetonitrile, tetrahydrofuran, dioxane, 2-methoxyethanol, t-BuOH, 2-BuOH, trifluoroethanol, water, and mixtures thereof. The admixing can occur at a temperature in a range of about 40° C. to 90° C., or about 60° C. In one aspect, the conditions sufficient to form NAPH in step (ii) comprise acidic conditions. The acidic conditions can comprise an acid selected from HCl, HBr, $H_2SO_4$, $CH_3SO_3H$, H3PO4, trifluoromethanesulfonic acid, trifluoroacetic acid, toslylic acid, and combinations thereof. In one aspect, the acid can be present in an amount in a range of about 1 equivalent to about 10 equivalents, or about 1.2 equivalents. The acidification can occur at a temperature in a range of 50° C. to 100° C., or about 65° C. The yield of NAPH can be at least about 80%, at least about 90%, or at least about 95%. The NAPH purity is at least about 80%, at least about 30%, or at least about 10%.

In one aspect, the protected N-(3-formyl-4-amino-2-alkoxy)pyridine is formed by admixing a protected N-(4-amino-2-alkoxy)pyridine:

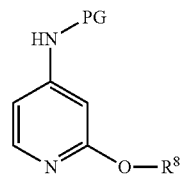

with a lithium reagent, under conditions sufficient to form the protected N-(3-formyl-4-amino-2-alkoxy)pyridine:

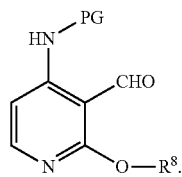

In one aspect, the lithium reagent can be selected from the group consisting of n-hexyl lithium, n-butyl lithium, s-butyl lithium, lithium bis(trimethylsilyl)amide ("LiHMDS"), lithium diisopropyl amide ("LDA"), Lithium tetramethylpiperidin (LiTMP), and combinations thereof. In one aspect, the lithium reagent comprises one or both of n-hexyl lithium and n-butyl lithium. The admixing can occur at a temperature in a range of about −50° C. to 25° C., or about −30° C. to −10° C. The yield of the protected N-(3-formyl-4-amino-2-alkoxy)pyridine can be at least about 80% or at least about 85% or at least about 90%. The purity of the protected N-(3-formyl-4-amino-2-alkoxy)pyridine can be at least about 95%, or at least about 60%, or at least about 30%.

In one aspect, the protected N-(4-amino-2-alkoxy)pyridine is formed by admixing 2-alkoxy-pyridin-4ylamine:

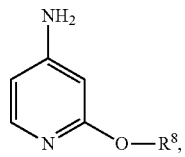

with base and a pivaloyl compound of Formula (IV):

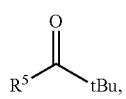

(IV)

under conditions sufficient to form protected N-(4-amino-2-alkoxy)pyridine, wherein $R^5$ is Cl, Br, or OC(O)alkyl. In one aspect, $R^5$ can be selected from the group consisting of Cl, Br, and OC(O)alkyl. In a further aspect, alkyl can be selected from the group consisting of Me, Et, Pr, iPr, n-Bu, sec-Bu, and tert-Bu. The admixing can occur at a temperature in a range of about −30° C. to 50° C., or about 0° C. The yield of the protected N-(4-amino-2-alkoxy)pyridine is at least about 85%, at least about 90%, or at least about 95%. In one aspect, the N-(4-amino-2-alkoxy)pyridine has a purity of at least about 90%, at least about 80%, or at least about 60%.

In one aspect of the present disclosure, the 1-hydroxy-2-(2-methoxyethoxy)ethane-1-sulfonate:

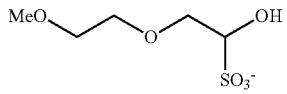

is formed by contacting 2-(2-methoxyethoxy)acetaldehyde:

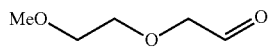

with $HSO_3^-$, $S_2O_5^{2-}$, or a combinations thereof, under conditions sufficient to form the 1-hydroxy-2-(2-methoxyethoxy)ethane-1-sulfonate. In one aspect, the $HSO_3^-$ and $S_2O_5^{2-}$ have a counterion selected from the group consisting of $Li^+$, $K^+$, $Na^+$, $Me_4N^+$, $Et_4N^+$, $Bu_4N^+$, and combinations thereof. In a further aspect, the 2-(2-methoxyethoxy)acetaldehyde is formed by oxidizing 2-(2-methoxyethoxy)-1-ethanol:

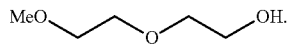

with an oxidizing agent. The oxidizing agent can be selected from the group consisting of oxalyl chloride, pyridinium chlorochromate ("PCC"), pyridinium dichromate ("PDC"), dimethyl sulfoxide ("DMSO") activated with a sulfur trioxide pyridine complex, and combinations thereof. The oxidizing can occur in the presence of a base, or example. The base can be selected from the group consisting of triethylamine, DIPEA, N-methylmophline, and combinations thereof. In one aspect, the base can comprise triethylamine. The can oxidizing occur in a solvent comprising methoxyethanol.

In one aspect, the 2-(2-methoxyethoxy)acetaldehyde is formed by:

(i) admixing

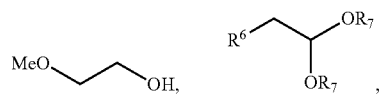

and a strong base to form

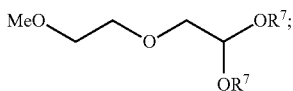

wherein $R^6$ is Cl, Br, I or cyclic diol protecting groups; and $R^7$ is $C_{1-4}$alkyl; and (ii) hydrolyzing

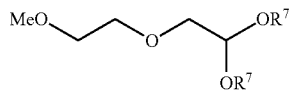

to form the 12-(2-methoxyethoxy)acetaldehyde:

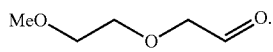

In one aspect of the present disclosure, $R^6$ can be selected from the group consisting of Cl, Br, I, ethylene glycol, and 1,3-propanediol. Further, each $R^7$, independently, can be selected from the group consisting of $CH_3$, $CH_2CH_3$, and $CH_2CH_2CH_3$. In one aspect, $R^7$ can be $CH_2CH_3$. In one aspect, the strong base can be present in an amount in a range of about 1 equivalent to about 1.5 equivalents. In one aspect, the strong base is present in an amount of about 1.2 equivalents. In one aspect, the strong base is selected from the group consisting of NaH, LiH, LiOt-Bu, BuLi, hexLi, NaOt-Bu, KOt-Bu, KH, LiOH, and combinations thereof. The admixing can occur in a temperature range of about 100° C. to about 120° C., or about 110° C. The hydrolyzing can occur in acidic conditions. The yield of the sulfonate can be at least about 50%, at least about 60%, at least about 70%, or at least about 80%. It is contemplated that the sulfonate has a purity of at least about 40%, at least about 50%, or at least about 60%.

The present disclosure provides a method comprising:

(i) admixing a methylnicotinate of Formula (I):

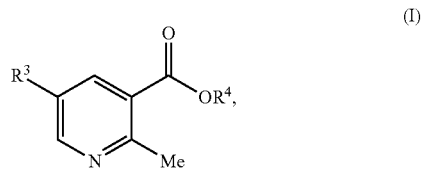

(I)

wherein $R^3$ is Cl, Br, or I, and $R^4$ is alkyl;

with 1,3,5-triazine, and a base, under conditions sufficient to form a naphthyridinone of Formula (II):

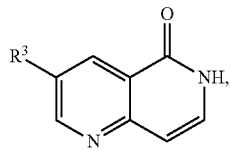

and (ii) admixing the naphthyridinone of Formula (II) with methoxyethanol, a base, and a copper (I) catalyst, under conditions sufficient to form 3-(2-methoxyethoxy)-1,6-naphthyridin-5(6H)-one ("NAPH"):

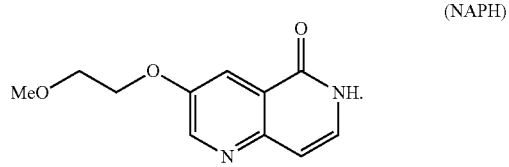 [SMILES: COCCOc1cnc2cc[nH]c(=O)c2c1]

The present disclosure provides a method comprising admixing protected N-(4-amino-2-alkoxy)pyridine:

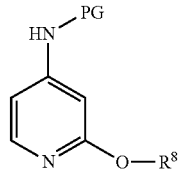

with a lithium reagent, under conditions sufficient to form protected N-(3-formyl-4-amino-2-alkoxy)pyridine:

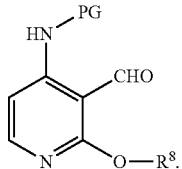

The present disclosure provides a method comprising admixing protected N-(3-formyl-4-amino-2-alkoxy)pyridine:

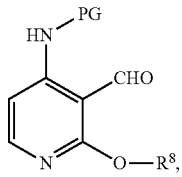

with 1-hydroxy-2-(2-methoxyethoxy)ethane-1-sulfonate:

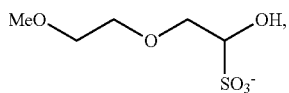

and base, under conditions sufficient to form a naphthyridine of Formula (III):

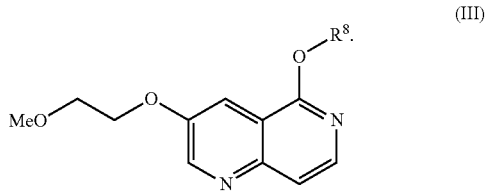

In one aspect, the method further comprises acidifying the naphthyridine of Formula (III), under conditions sufficient to form 3-(2-methoxyethoxy)-1,6-naphthyridin-5(6H)-one ("NAPH"):

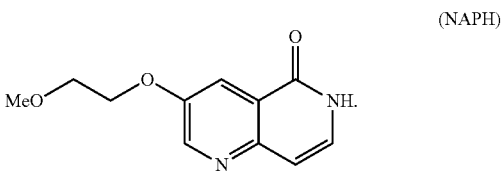 [SMILES: COCCOc1cnc2cc[nH]c(=O)c2c1]

In one aspect, the present disclosure provides a method comprising:

(i) admixing 4-amino-2-alkoxypyridine:

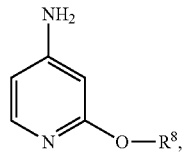

wherein $R^8$ is an alkyl group,
with a pivaloyl compound of Formula (IV):

wherein $R^5$ is Cl, Br, or OC(O)alkyl, and
base, under conditions sufficient to form N-(2-alkoxypyridin-4-yl)pivalamide:

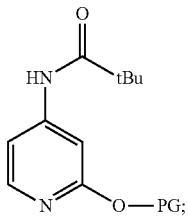

(ii) admixing N-(2-alkoxypyridin-4-yl)pivalamide with a lithium reagent, under conditions sufficient to form the protected N-(3-formyl-4-amino-2-alkoxy)pyridine:

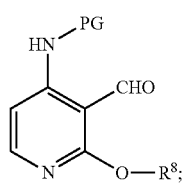

(iii) admixing the protected N-(3-formyl-4-amino-2-alkoxy) pyridine with 1-hydroxy-2-(2-methoxyethoxy)ethane-1-sulfonate:

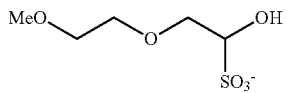

and base, under conditions sufficient to form a naphthyridine of Formula (III):

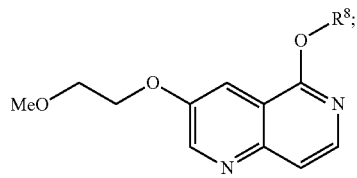

and
(iv) acidifying the naphthyridine of Formula (III), under conditions sufficient to form 3-(2-methoxyethoxy)-1,6-naphthyridin-5(6H)-one ("NAPH"):

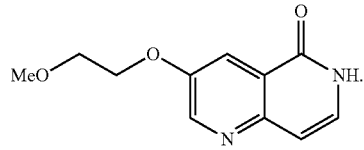

The present disclosure further provides a method comprising contacting 2-(2-methoxyethoxy)acetaldehyde:

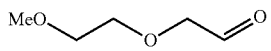

with $HSO_3^-$, $S_2O_5^{2-}$, or a combinations thereof, under conditions sufficient to form 1-hydroxy-2-(2-methoxyethoxy)ethane-1-sulfonate:

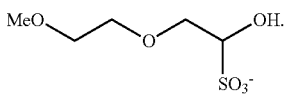

The present disclosure provides a method comprising crystallizing Compound A:

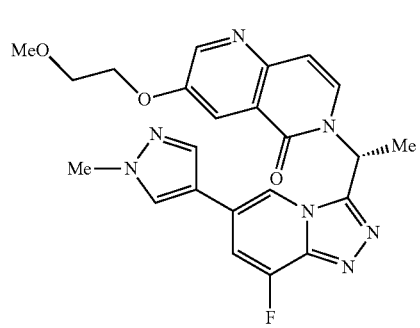

in an alcohol and water solution, under conditions sufficient to form a monohydrate form of Compound A:

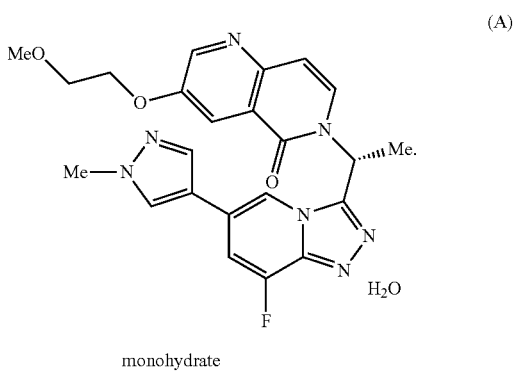

monohydrate

The present disclosure provides a method comprising:
(i) admixing 3-(2-methoxyethoxy)-1,6-naphthyridin-5(6H)-one ("NAPH"):

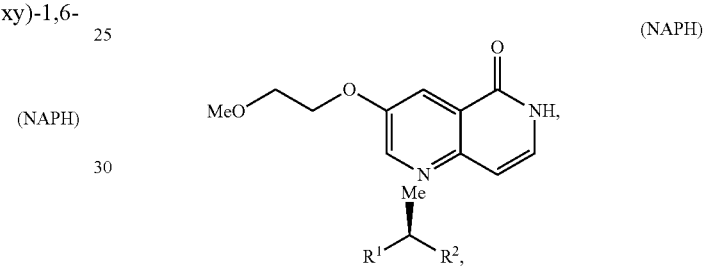

and a base, under conditions sufficient to form NAPA:

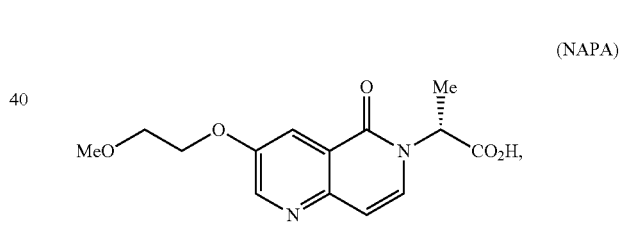

wherein $R^1$ is Br, Cl, I, or OTf, and
$R^2$ is COOH or $C_{1-3}$alkyl ester, and
when $R^2$ is $C_{1-3}$alkyl ester, the method of forming the NAPA further comprises hydrolyzing the $C_{1-3}$alkyl ester to form an acid;
(ii) admixing the NAPA with 3-fluoro-2-hydrazinyl-5-(1-methyl-1H-pyrazl-4-yl)pyridine ("PYRH"):

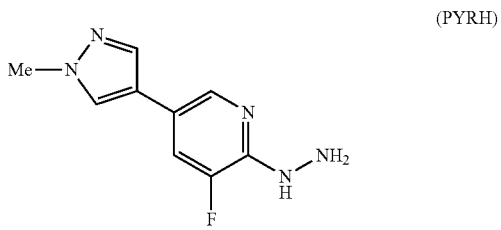 [SMILES: Cn1cc(-c2cnc(NN)c(F)c2)cn1]

and a coupling reagent, and under conditions sufficient to form (R)—N'-(3-fluoro-5-(1methyl-1H-pyrazol-4-yl)pyri din-2-yl)-2-(3-(2-methoxyethoxy)-5-oxo-1,6-naphthyridin-6(5H)yl)propanehydrazide ("HYDZ"):

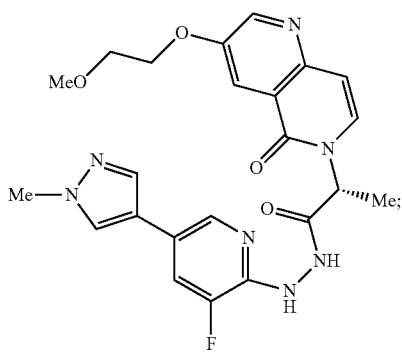

and (iii) reacting the HYDZ under conditions sufficient to form (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

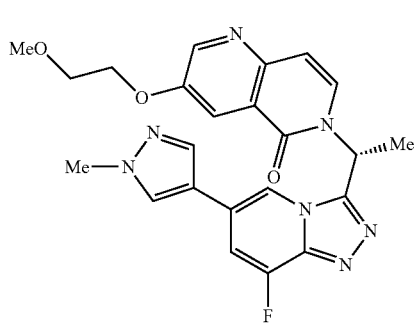

In one aspect, the reacting comprises contacting the HYDZ with a thiophosphetane compound. In another aspect, the reacting comprises contacting the HYDZ with a phosphorus (V) dehydrating agent.

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

We claim:

1. A method comprising;
    subjecting (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ"):

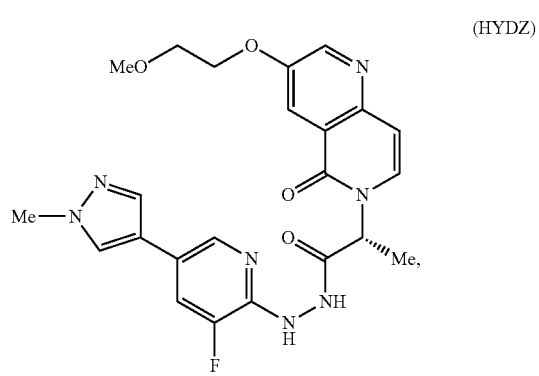

to a dehydration reaction with either a thiophosphetane compound or a phosphorus (V) dehydrating agent thereby forming (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

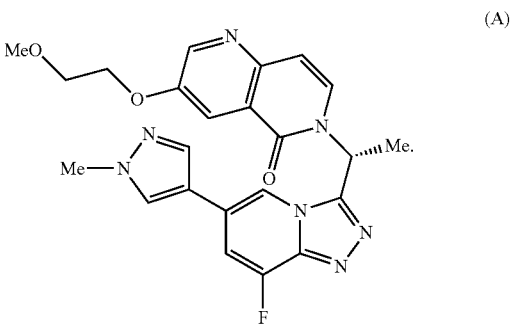 [SMILES: COCCOc1cnc2ccn([C@H](C)c3nnc4c(F)cc(-c5cnn(C)c5)cn34)c(=O)c2c1]

2. The method of claim 1, wherein the thiophosphetane compound comprises a 2,4-bis(aryl)-1,3-dithia-2,4-diphosphetane 2,4-disulfide compound.

3. The method of claim 2, wherein the 2,4-bis(aryl)-1,3-dithia-2,4-diphosphetane 2,4-disulfide compound is:

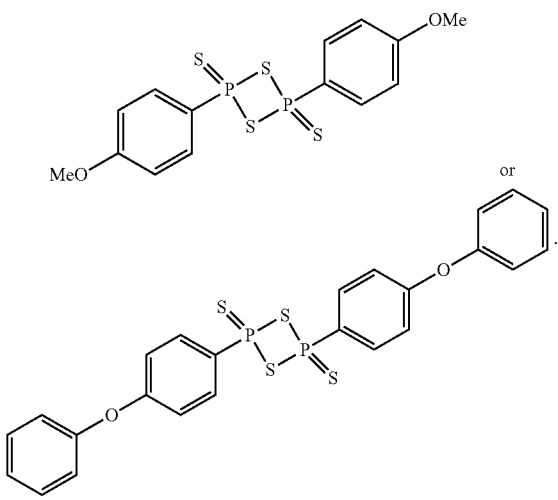

or

4. The method of claim 1 further comprising contacting Compound A with a water-rich solvent having a pH of at least 7 to form the monohydrate form of Compound A.

5. The method of claim 1, wherein the dehydrating agent comprises a compound having a structure:

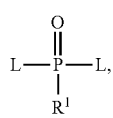

wherein each L independently is $C_{1-6}$ alkyl, O—$C_{1-6}$ alkyl, aryl, O-aryl, Br, Cl, or I; and $R^1$ is Cl, Br, or I.

6. The method of claim 5, wherein each L is selected from the group consisting of Me, Et, t-Bu, O-Me, O-Et, O-t-Bu, phenyl, O-phenyl, Br, and Cl.

7. The method of claim 1, further comprising contacting Compound A with an acid under conditions sufficient to form a salt of Compound A.

8. The method of claim 7, wherein the acid is selected from the group consisting of hydrochloric acid, phosphoric acid, camphorsulfonic acid, 2-naphthylsulfonic acid, methansulfonic acid, benzenesulfonic acid and derivatives thereof, succinic acid, tartaric acid, fumaric acid, maleic acid, and combinations thereof.

9. The method of claim 1 further comprising crystallizing Compound A in a solution comprising alcohol and water to form a monohydrate form of Compound A:

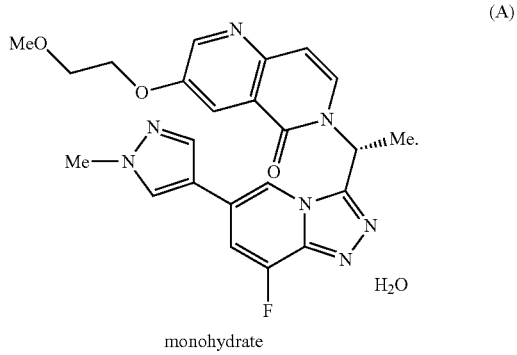

monohydrate

10. The method of claim 1, wherein the HYDZ is formed by reacting (R)-2-(3-(2-methoxyethoxy)-5-oxo-1,6-naphthyridin-6(5H)-yl)propanoic acid ("NAPA"):

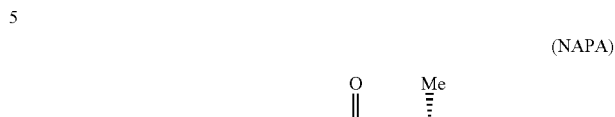

with 3-fluoro-2-hydrazinyl-5-(1-methyl-/H-pyrazl-4-yl) pyridine ("PYRH"):

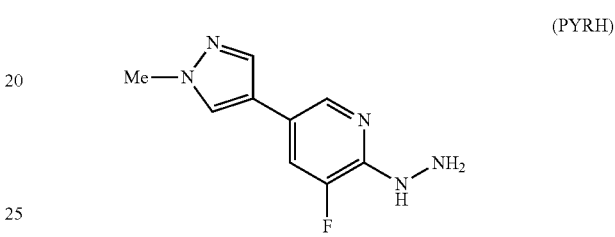

and a coupling reagent to form HYDZ:

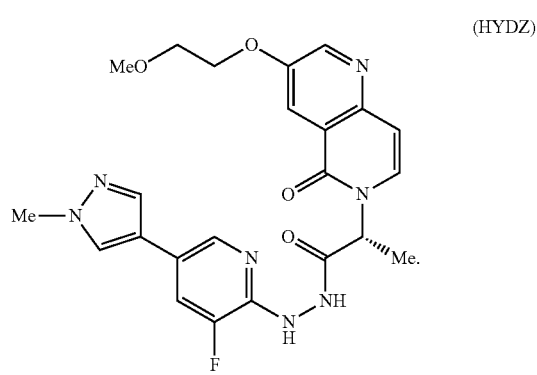 [SMILES: COCCOc1cnc2ccn([C@H](C)C(=O)NNc3ncc(-c4cnn(C)c4)cc3F)c(=O)c2c1]

11. The method of claim 10, wherein NAPA is a salt comprising HCl, HBr, sulfonic acid, diisopropylamine, or potassium.

12. The method of claim 11, wherein the sulfonic acid salt is selected from the group consisting of 2-naphthalenesulfonic acid, 1-naphthalenesulfonic acid, m-xylenesulfonic acid, p-toluene sulfonic acid, benzene sulfonic acid, 2-nitrobenzenesulfonic acid, 2,5-dichlorobenzene sulfonic acid, (−)-10-camphorsulfonic acid, (+)-camphor-10-sulfonic acid, p-chlorobenzene sulfonic acid, methanesulfonic acid, and combinations thereof.

13. The method of claim 10, wherein the coupling reagent comprises a reagent selected from the group consisting of a carbodiimide reagent, a phosphonium reagent, a uronium reagent, an immonium reagent, an imidazolium reagent, an organophosphorus reagent, an acid chloride reagent, a chloroformate reagent, a pyridinium reagent, and combinations thereof.

14. The method of claim 10, wherein the reacting occurs in the presence of a tertiary amine base selected from the group consisting of N,N-diisopropylethylamine ("DIEA"), triethylamine ("TEA"), N-methylmorpholine ("NMM"), and combinations thereof.

15. The method of claim 10, wherein the NAPA is formed by admixing 3-(2-methoxyethoxy)-1,6-naphthyridin-5(6H)-one ("NAPH"):

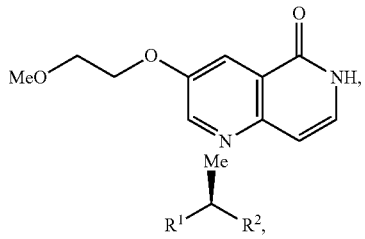
(NAPH)

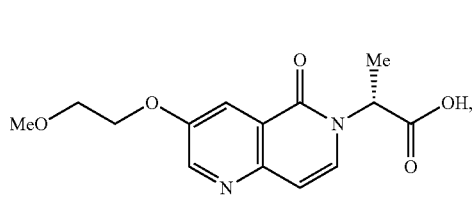

and a base to form NAPA:

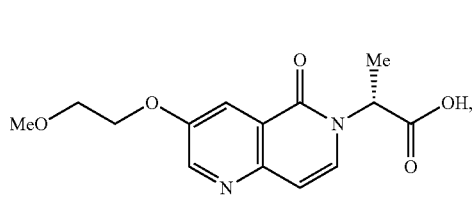
(NAPA)

wherein $R^1$ is Br, Cl, I, or OTf and
$R^2$ is COOH or $C_{1-3}$ alkyl ester, and
when $R^2$ is $C_{1-3}$ alkyl ester, the method of forming the NAPA further comprises hydrolyzing the $C_{1-3}$ alkyl ester to form an acid.

16. The method of claim 15, wherein $R^2$ is COOH.

17. The method of claim 15, wherein the base is selected from the group consisting of KOtBu, NaOtBu, LiOtBu, Mg(OtBu)$_2$, Al(OtBu)$_3$, NaOSiMe$_3$, Cs$_2$CO$_3$, potassium bis(trimethylsilyl)amide ("KHMDS"), sodium bis(trimethylsilyl)amide ("NaHMDS"), lithium bis(trimethylsilyl)amide ("LiHMDS"), and combinations thereof.

18. The method of claim 10, wherein the PYRH is formed by
(i) admixing

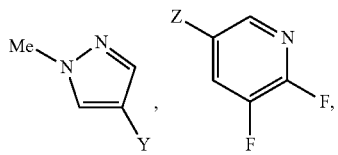

and a catalyst to form an intermediate:

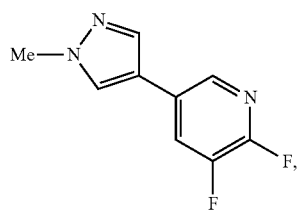 [SMILES: Cn1cc(-c2cnc(F)c(F)c2)cn1]

wherein:
(a) Y is F, Cl, Br, I, or OTf, and Z comprises boronic acid, boronic ester, magnesium, zinc, zirconium, tin, or silicon; or
(b) Y comprises boronic acid, boronic ester, magnesium, zinc, zirconium, tin, or silicon, and Z is F, Cl, Br, I, or OTf; and (ii) admixing

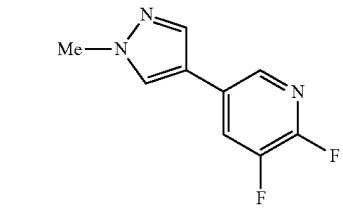 [SMILES: Cn1cc(-c2cnc(F)c(F)c2)cn1]

and H$_2$NNH$_2$, under conditions sufficient to form PYRH:

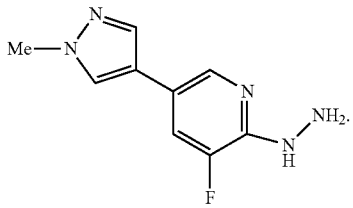
(PYRH)

19. The method of claim 18, wherein the catalyst comprises palladium (0), palladium (II), nickel, copper, iron, or combinations thereof.

20. The method of claim 18, wherein the admixing in step (i) occurs in the presence of a base.

21. The method of claim 18, wherein Y is Cl, Br, I, or OTf, and Z comprises boron, magnesium, zinc, zirconium, tin, or silicon.

22. The method of claim 21, wherein Z comprises boronic acid, boronic ester, or boronate.

23. The method of claim 18, wherein Y comprises boron, magnesium, zinc, zirconium, tin, or silicon, and Z is Cl, Br, I, or OTf.

24. The method of claim 23, wherein Y comprises boronic acid, boronic ester, or boronate.

25. The method of claim 18, wherein the admixing in step (i) occurs in the presence of a phase transfer catalyst.

26. The method of claim 15, wherein the NAPH is formed by
(i) admixing a methylnicotinate of Formula (I):

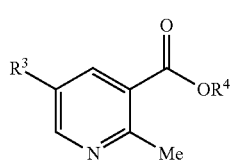
(I)

wherein $R^3$ is Cl, Br, or I, and $R^4$ is alkyl;
with 1,3,5-triazine, and a base to form a naphthyridinone of Formula (II):

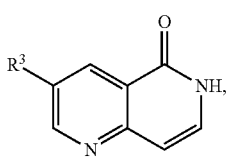
(II)

and
(ii) admixing the naphthyridinone of Formula (II) with methoxyethanol, a base, and a copper (I) catalyst, under conditions sufficient to form NAPH:

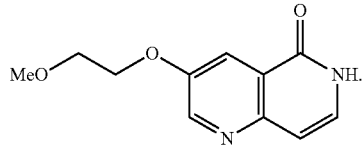 [SMILES: COCCOc1cnc2cc[nH]c(=O)c2c1]

27. The method of claim 26, wherein the copper (I) catalyst is selected from the group consisting of CuBr, CuBr-DMS, Cu(OAc), Cu(OTf) and combinations thereof.

28. The method of claim 26, wherein the base in step (i) is selected from the group consisting of $Cs_2CO_3$, KOtBu, $K_3PO_4$, $K_2CO_3$, and combinations thereof.

29. The method of claim 15, wherein the NAPH is formed by:
(i) admixing protected N-(3-formyl-4-amino-2-alkoxy) pyridine:

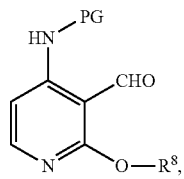

wherein PG is a protecting group and $R^8$ is alkyl, with 1-hydroxy-2-(2-methoxyethoxy)ethane-1-sulfonate:

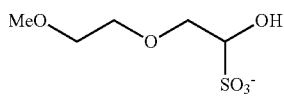

and base, under conditions sufficient to form a naphthyridine of Formula (III):

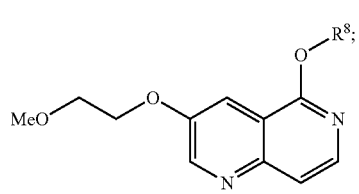

(III)

and
(ii) acidifying the naphthyridine of Formula (III) to form NAPH:

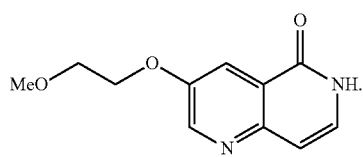 [SMILES: COCCOc1cnc2cc[nH]c(=O)c2c1]

30. A method comprising:
(i) admixing a methylnicotinate of Formula (I):

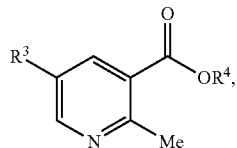

(I)

wherein $R^3$ is Cl, Br, or I, and $R^4$ is alkyl;
with 1,3,5-triazine, and a base to form a naphthyridinone of Formula (II):

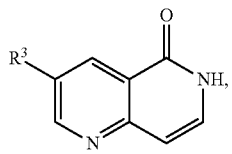

and
(ii) admixing the naphthyridinone of Formula (II) with methoxyethanol, a base, and a copper (I) catalyst, under conditions sufficient to form 3-(2-methoxyethoxy)-1,6-naphthyridin-5(6H)-one ("NAPH"):

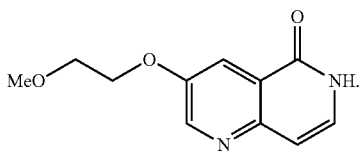

(NAPH)

31. A method comprising:
(i) admixing 4-amino-2-alkoxypyridine:

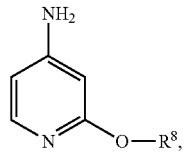

wherein $R^8$ is an alkyl group,
with a pivaloyl compound of Formula (IV):

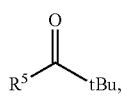

(IV)

wherein $R^5$ is Cl, Br, or OC(O)alkyl, and
base to form N-(2-alkoxypyridin-4-yl)pivalamide:

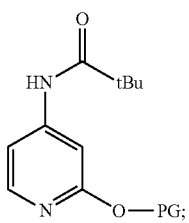

(ii) admixing N-(2-alkoxypyridin-4-yl)pivalamide with a lithium reagent to form the protected N-(3-formyl-4-amino-2-alkoxy)pyridine:

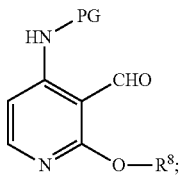

(iii) admixing the protected N-(3-formyl-4-amino-2-alkoxy)pyridine with 1-hydroxy-2-(2-methoxyethoxy)ethane-1-sulfonate:

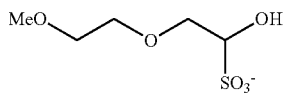

and base to form a naphthyridine of Formula (III):

(III)

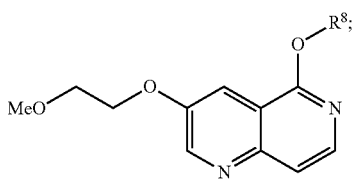

and (iv) acidifying the naphthyridine of Formula (III), under conditions sufficient to form 3-(2-methoxyethoxy)-1,6-naphthyridin-5(6H)-one ("NAPH"):

(NAPH)

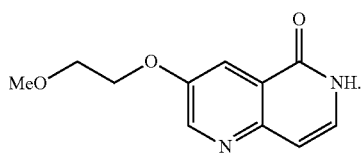

32. A method comprising:
(i) admixing 3-(2-methoxyethoxy)-1,6-naphthyridin-5(6H)-one ("NAPH"):

(NAPH)

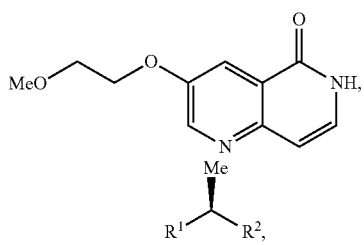

and a base to form NAPA:

(NAPA)

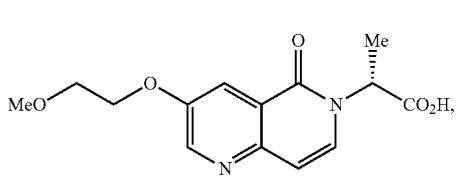

wherein $R^1$ is Br, Cl, I, or OTf, and $R^2$ is COOH or $C_{1-3}$alkyl ester, and when $R^2$ is $C_{1-3}$alkyl ester, the method of forming the NAPA further comprises hydrolyzing the $C_{1-3}$alkyl ester to form an acid;

(ii) admixing the NAPA with 3-fluoro-2-hydrazinyl-5-(1-methyl-/H-pyrazl-4-yl)pyridine ("PYRH"):

(PYRH)

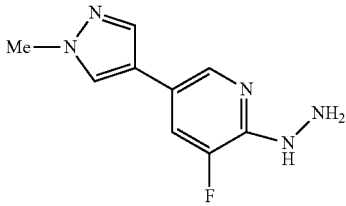

and a coupling reagent to form (R)—N'-(3-fluoro-5-(1methyl-1H-pyrazol-4-yl)pyridin-2-yl)-2-(3-(2-methoxyethoxy)-5-oxo-1,6-naphthyridin-6(5H)yl)propanehydrazide ("HYDZ"):

(HYDZ)

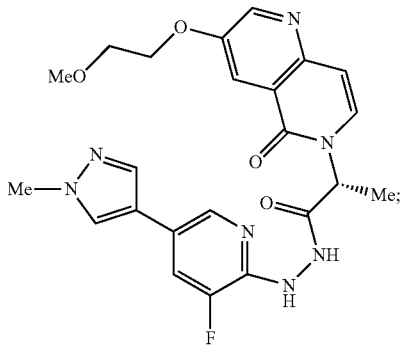

and (iii) subjecting the HYDZ to a dehydration reaction with either a thiophosphetane compound or a phosphorus (V) dehydrating agent thereby forming (R)-6-(1-(8-fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one ("A"):

(A)

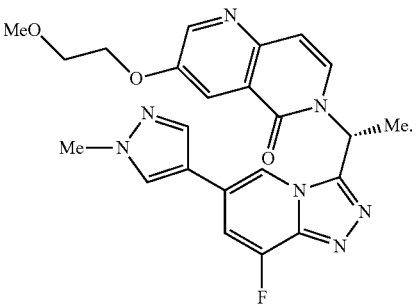

* * * * *